United States Patent [19]
Corenman et al.

[11] Patent Number: 4,907,166
[45] Date of Patent: Mar. 6, 1990

[54] MULTICHANNEL GAS ANALYZER AND METHOD OF USE

[75] Inventors: James E. Corenman, Oakland; Daniel S. Goldberger, San Francisco; Edward M. Richards, Pleasanton; Emil P. Rojas, Los Gatos; James R. Braig, Hayward; David A. Gallup, Union City, all of Calif.

[73] Assignee: Nellcor, Inc., Hayward, Calif.

[21] Appl. No.: 101,931

[22] Filed: Sep. 25, 1987

Related U.S. Application Data

[63] Continuation-in-part of Ser. No. 922,043, Oct. 12, 1986, Pat. No. 4,817,013.

[51] Int. Cl.$^4$ ............................................. G06F 15/42
[52] U.S. Cl. ...................................... 364/497; 128/719; 364/413.03
[58] Field of Search ............... 250/338, 343, 345, 344; 356/51, 437; 364/413.02, 496, 497, 498, 499, 413.03; 128/719; 422/83

[56] References Cited

U.S. PATENT DOCUMENTS

| | | | |
|---|---|---|---|
| 2,806,144 | 9/1957 | Berger et al. | 250/343 |
| 3,696,247 | 10/1972 | McIntosh et al. | 250/343 |
| 3,790,797 | 2/1974 | Sternberg et al. | 250/345 |
| 3,832,548 | 8/1974 | Wallack | 250/343 |
| 3,860,344 | 1/1975 | Garfunkel | 356/51 |
| 3,887,473 | 6/1975 | Sternberg et al. | 250/345 |
| 3,895,630 | 7/1975 | Bachman | 128/719 |
| 3,904,880 | 9/1975 | Benz et al. | 250/343 |
| 3,932,754 | 1/1976 | Riedl et al. | 250/343 |
| 3,957,372 | 5/1976 | Jowett et al. | 356/51 |
| 4,008,394 | 2/1977 | Risgin et al. | 245/345 |
| 4,011,859 | 3/1977 | Frankenberger | 128/719 |
| 4,013,260 | 3/1977 | McClatchie et al. | 250/343 |
| 4,069,420 | 1/1978 | Ross | 250/343 |
| 4,084,906 | 4/1978 | Bibbero | 250/343 |
| 4,153,837 | 5/1979 | Ross | 250/343 |
| 4,177,381 | 12/1979 | McClatchie et al. | 250/343 |
| 4,266,131 | 5/1981 | Ahjopalo et al. | 250/345 |
| 4,288,513 | 10/1980 | Elder et al. | 250/343 |
| 4,320,297 | 3/1982 | Cederstrand et al. | 250/343 |
| 4,336,453 | 6/1982 | Imaki et al. | 250/344 |
| 4,346,296 | 8/1982 | Passaro et al. | 250/343 |
| 4,355,233 | 10/1982 | Warnke et al. | 250/343 |
| 4,370,553 | 1/1983 | Waycaster et al. | 250/343 |
| 4,398,091 | 8/1983 | Passaro | 250/343 |
| 4,423,739 | 1/1984 | Passaro et al. | 128/719 |
| 4,509,359 | 4/1985 | Gedeon et al. | 128/719 |
| 4,578,762 | 3/1986 | Wong | 364/497 |
| 4,632,807 | 12/1986 | Marsoner | 422/83 |
| 4,692,621 | 9/1987 | Passaro et al. | 250/343 |

OTHER PUBLICATIONS

Cavitron Corp. Hospital Price List Entitled, "CO$_2$ Patient Monitors and N$_2$O Trace Gas Analyzers"; Oct. 16, 1985.

Cavitron Corp. Brochure Entitled, "End Tidal CO$_2$ Monitor: PM-20R/NR".

(List continued on next page.)

Primary Examiner—Parshotam S. Lall
Assistant Examiner—Kevin S. Teska
Attorney, Agent, or Firm—Wayne M. Kennard

[57] ABSTRACT

An improved gas analyzer system (FIG. 1) and method of use for detecting and displaying the partial pressures of certain constituent gases in a respiratory gas stream, the system comprising an optical bench (111) through which a respiratory gas flows and in which measurements of the gas are taken; analog input circuits (122) for receiving signals output from the optical bench (111) through which a respiratory gas flows and in which measurements of the gas are taken; analog processing circuits (124) for processing signals output from the analog input circuits (122); display processing circuits (128) for processing the signals output from the analog processing circuits (124) and other system circuitry; pixel logic circuits/analog outputs (130) for processing signals output from the display processing circuitry (128) and providing analog output ports; a five button panel (148), an alarm/knob board (144), and a speaker driver (152) for operator interface and activation of audible and visual alarms; a CRT driver for driving a CRT; and a power supply (158) for powering the system.

56 Claims, 31 Drawing Sheets

OTHER PUBLICATIONS

Engstrom AB Brochure Entitled, "Great Ideas Grow: Just Look at Engstrom Erica"; Oct. 16, 1985.

Allegheny International Medical Technology Brochure Entitled, "SARACAP: $CO_2$, $O_2$ and $N_2O$ Respiratory Monitor", 1985.

Andros Analyzers, Inc. Brochure Entitled, "Andros 400 Series End Tidal $CO_2$ Analyzer", 11/17/82.

Bergman et al., "The Collision Broadening Effect of Nitrous Oxide Upon Infrared Analysis of Carbon Dioxide During Anaesthesia", Anaesthesiology, Jan.–Feb. 1958, vol. 19, No. 1, pp. 19—26.

Cavitron Corp. Brochure Entitled, "Cavitron Introduces Patient Monitors for Respiratory Gas Analysis".

"Infrared Gas Analysis", *Applications of Infrared Detectors*, Mullard Ltd., Mullard House, Torrington Place, London WC1E 7HD, Ch. 10 (1971), pp. 129-142.

Perkin-Elmer Brochure Entitled, "ADVANTAGE: Confidence from Every Standpoint".

Puritan-Bennett Corp. Operating Manual Entitled, "AAM222 Operating Manual".

Puritan-Bennett Corp. Brochure Entitled, "Puritan-Bennett 222 Anaesthetic Agent Monitor".

Puritan-Bennett Corp. Brochure Entitled, "You Can Depend On It!: Puritan-Bennett $CO_2$ Monitor".

Solomon, "A Reliable, Accurate $CO_2$ Analyzer for Medical Use", Hewlett-Packard Journal, Sep. 1981, pp. 3-21.

Tecfair et al., "A Microcomputer-Controlled Infrared Analyzer for Multi-component Analysis", American Laboratory, Nov. 1976, pp. 91-100.

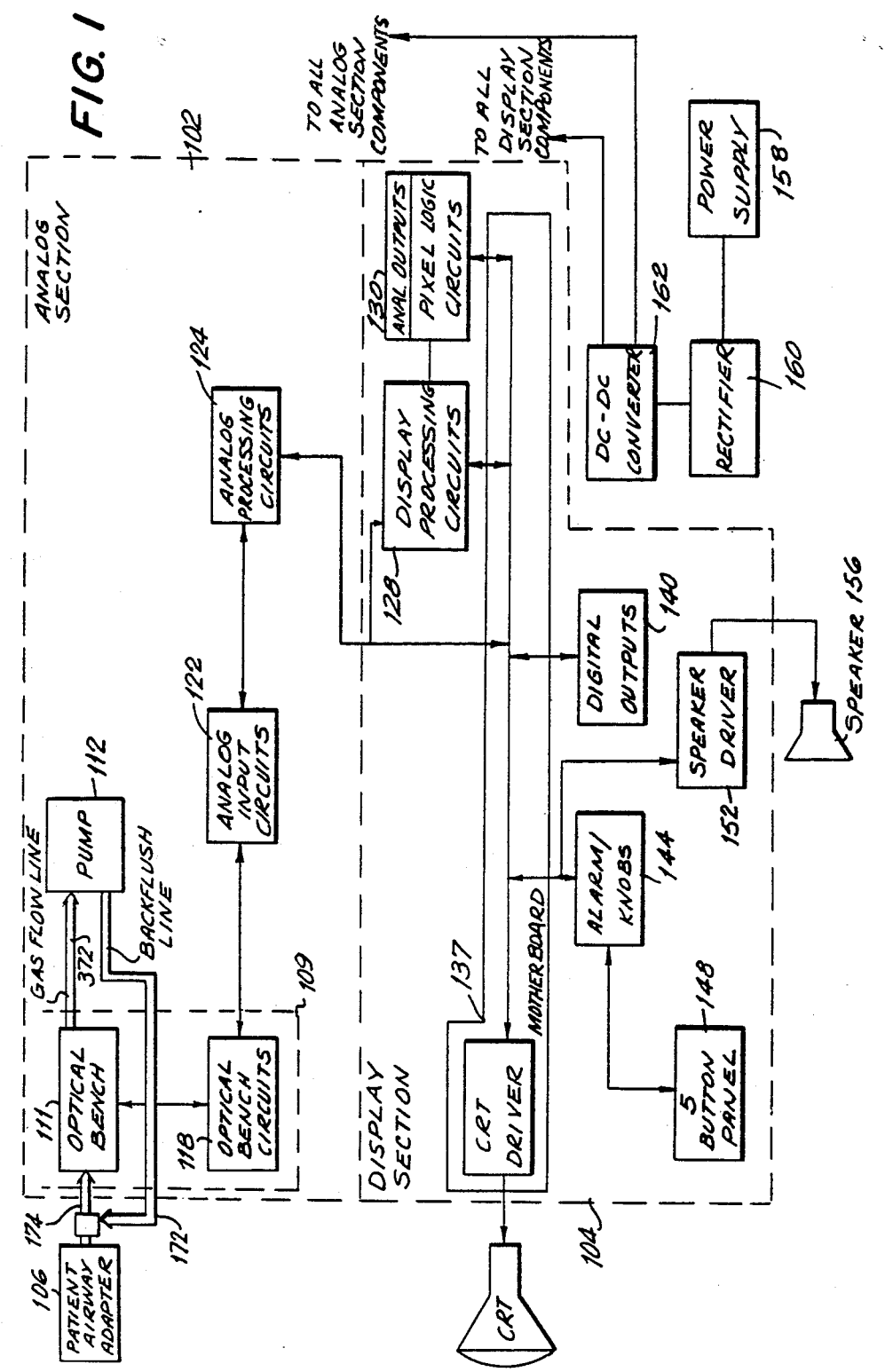

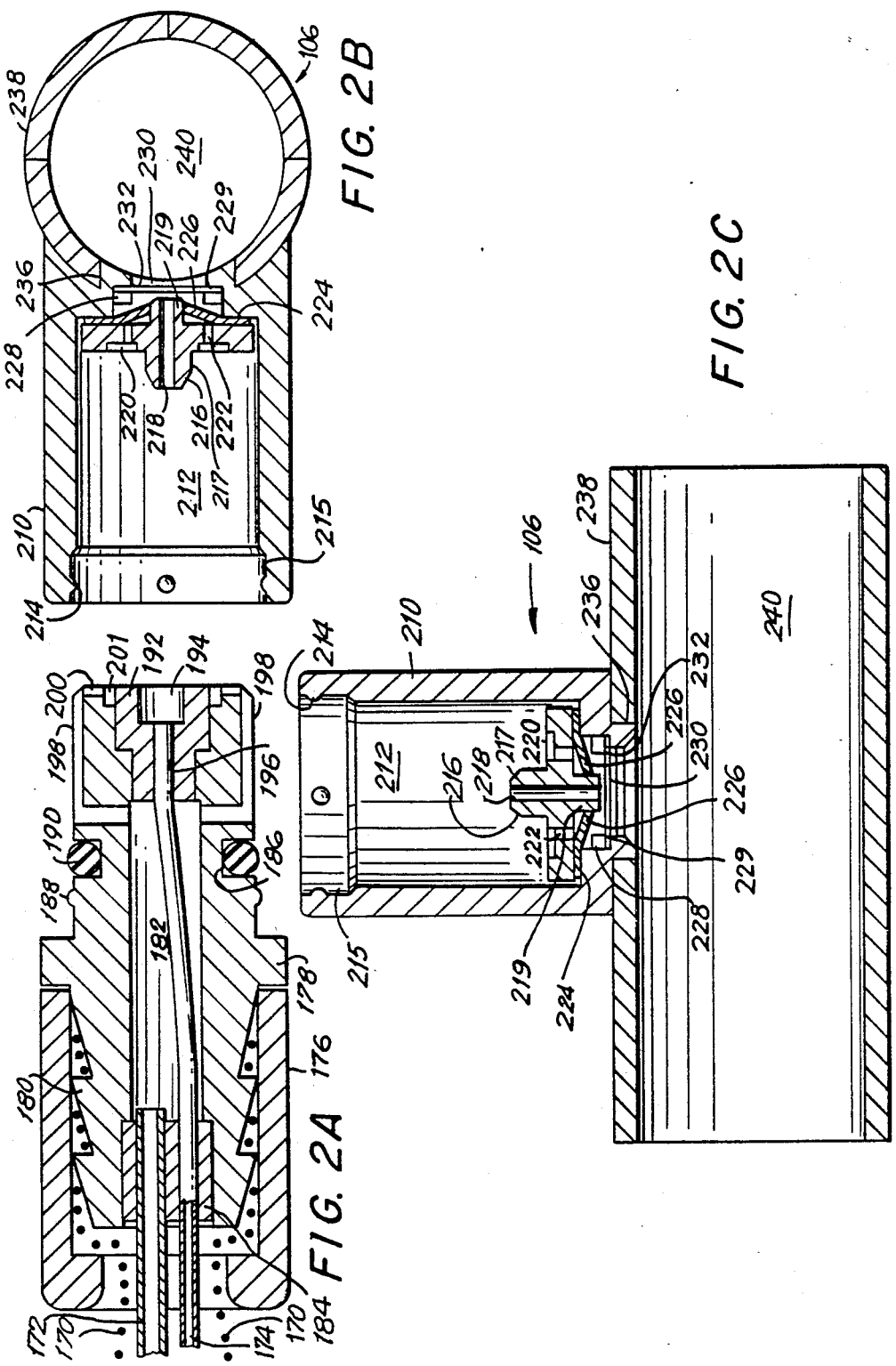

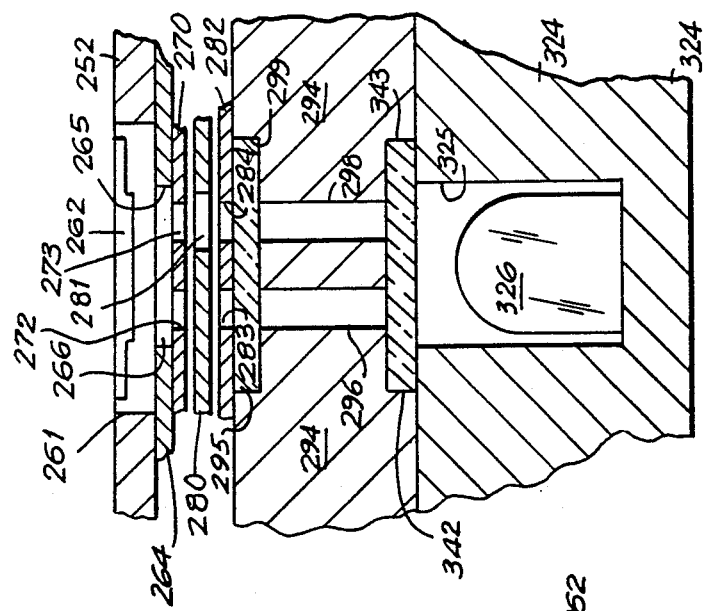
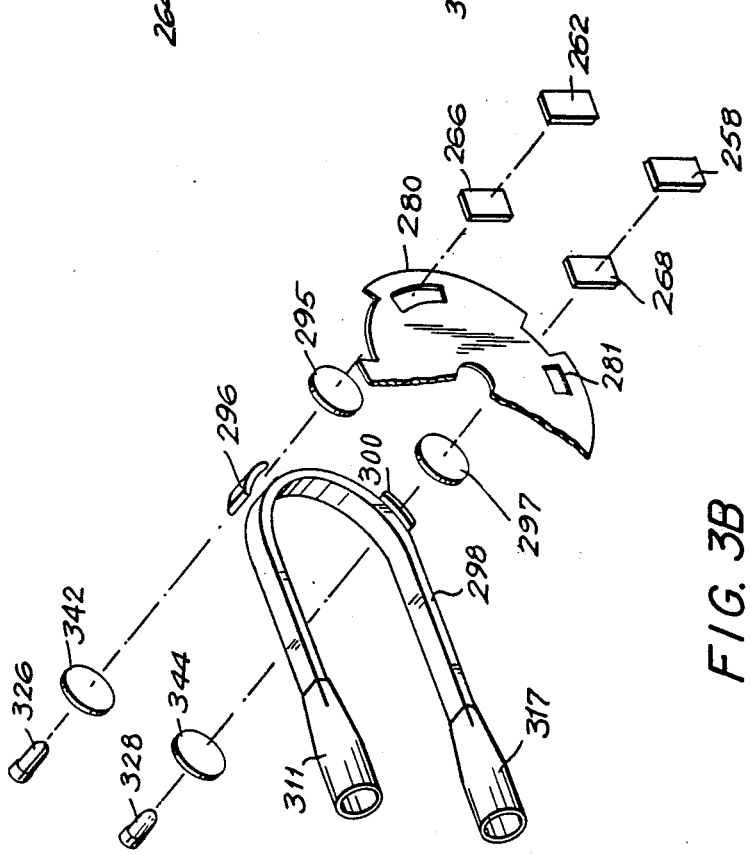
FIG. 3C
FIG. 3B

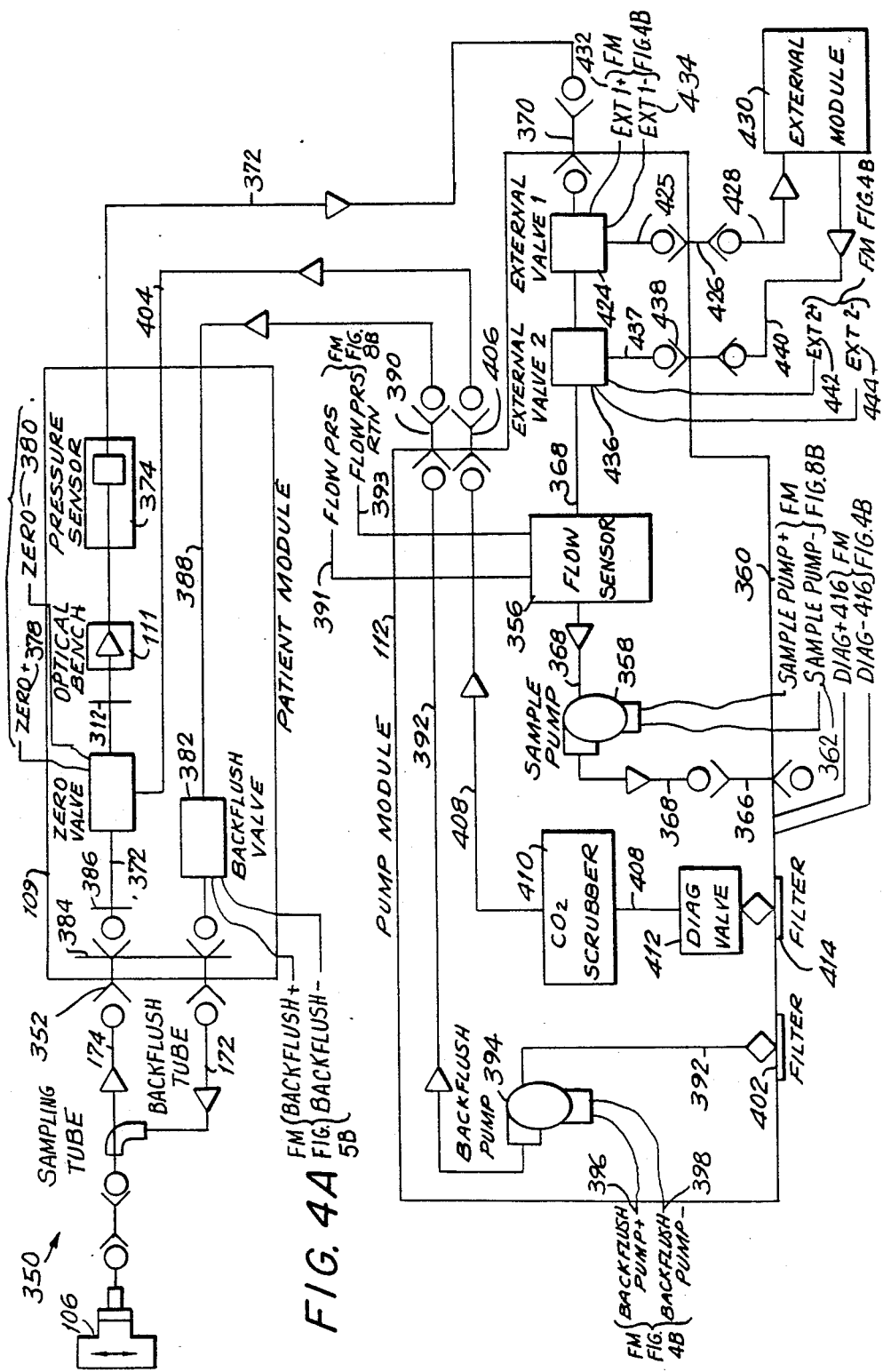

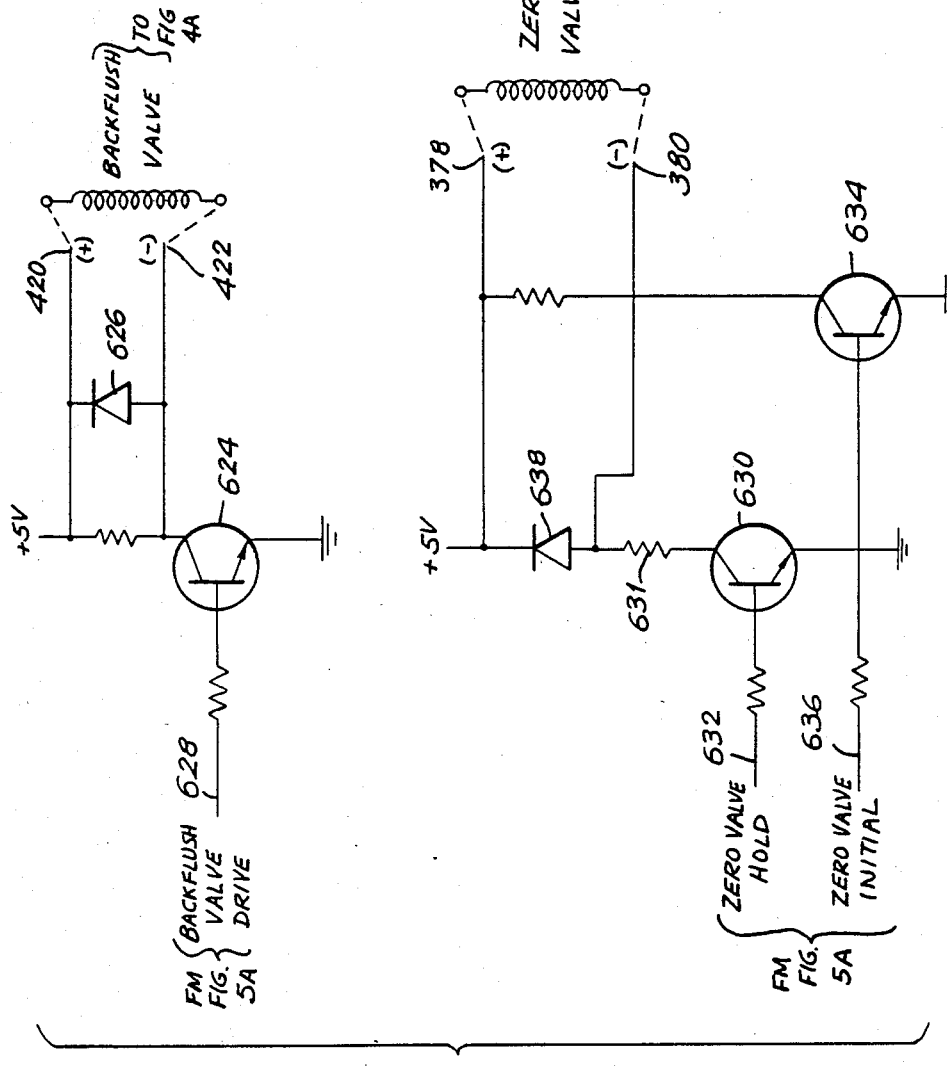

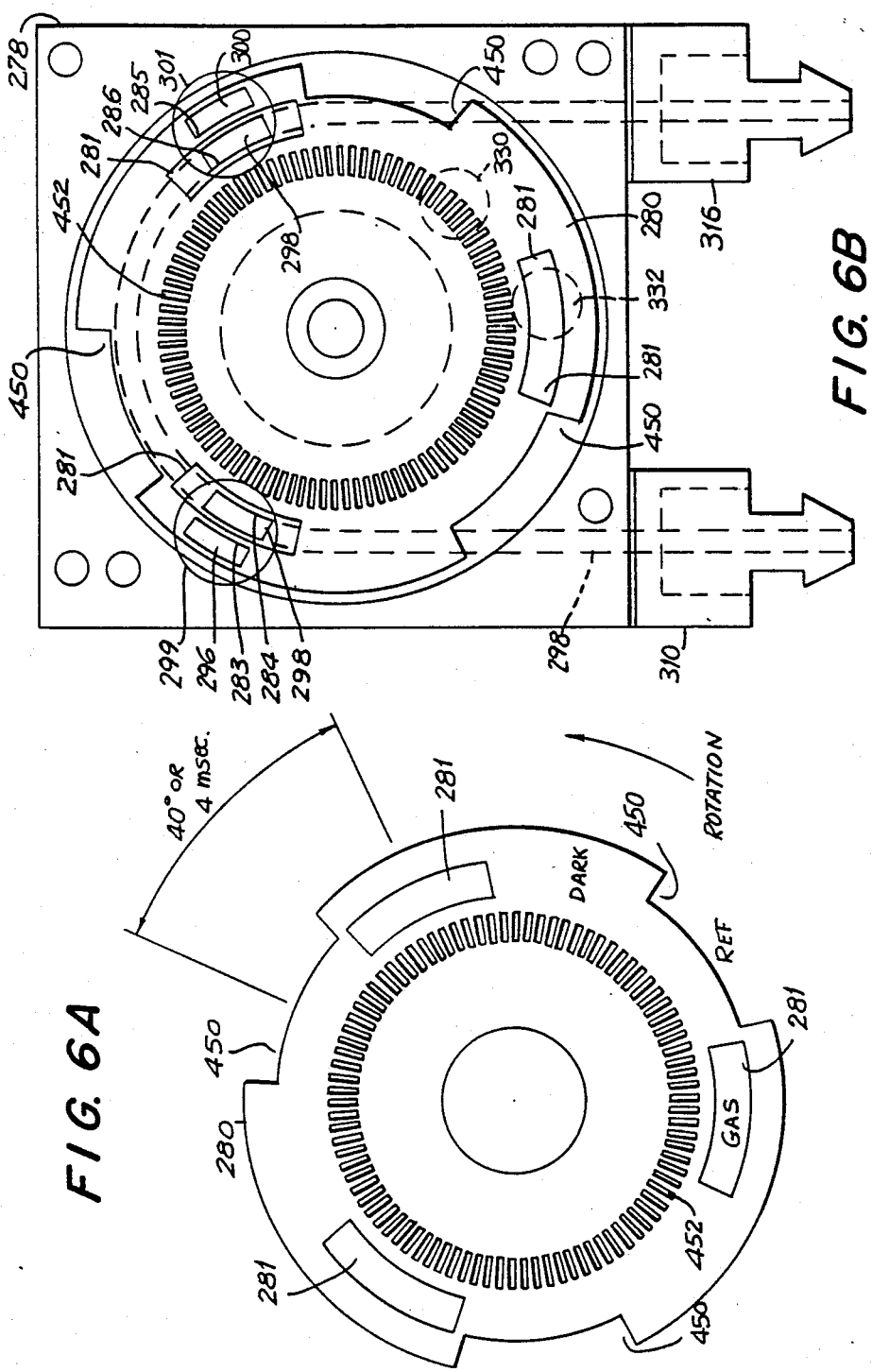

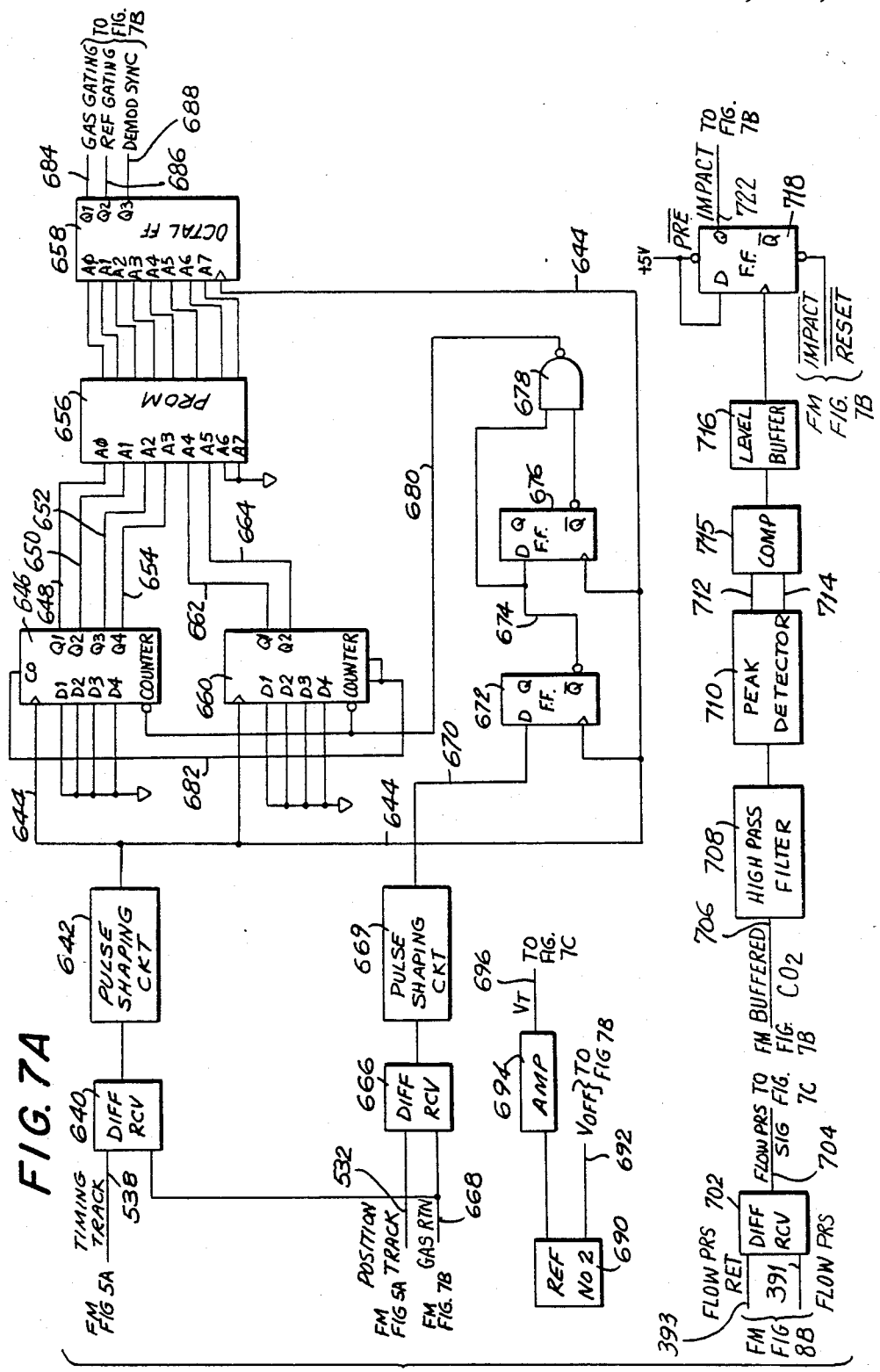

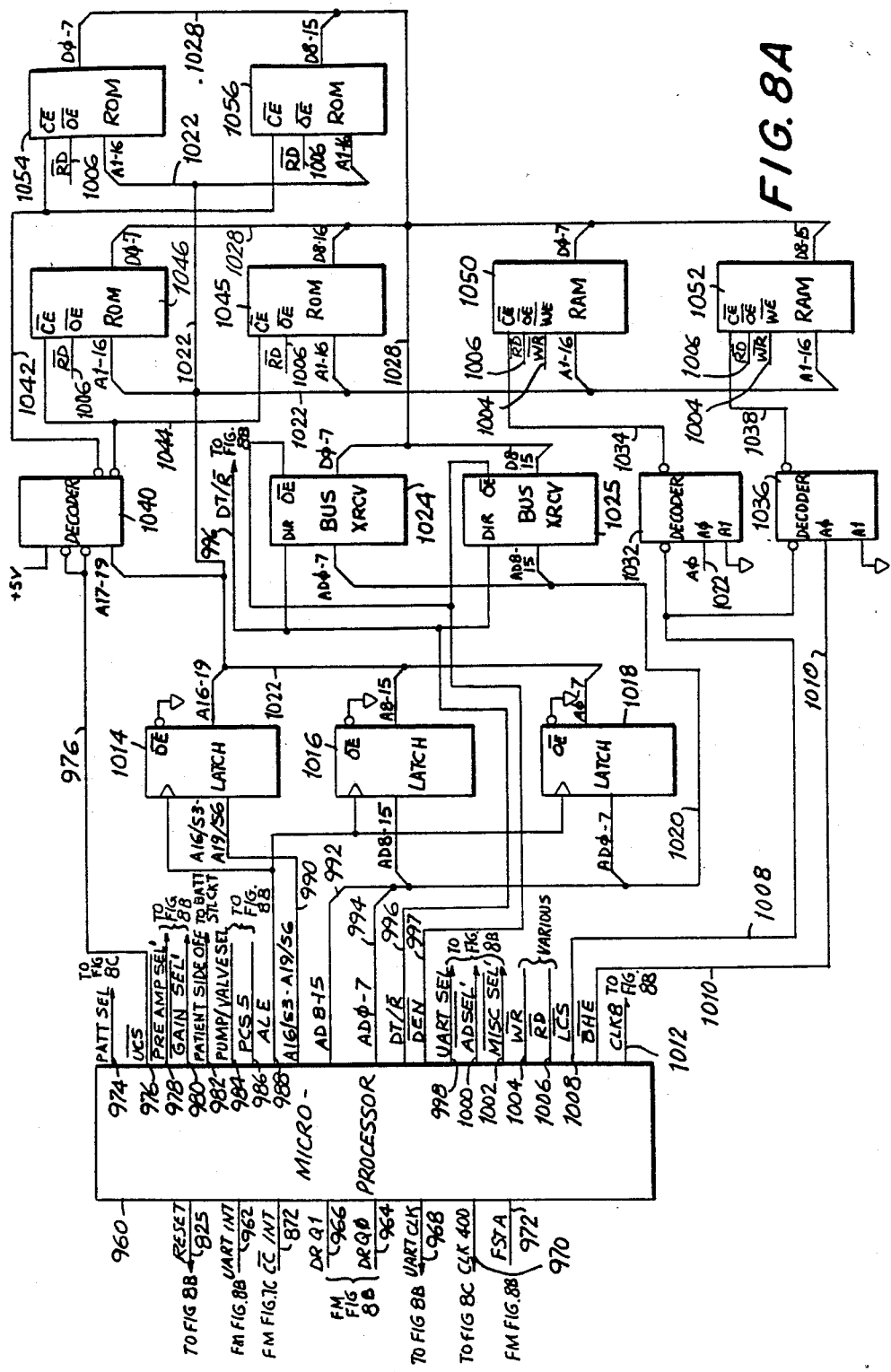

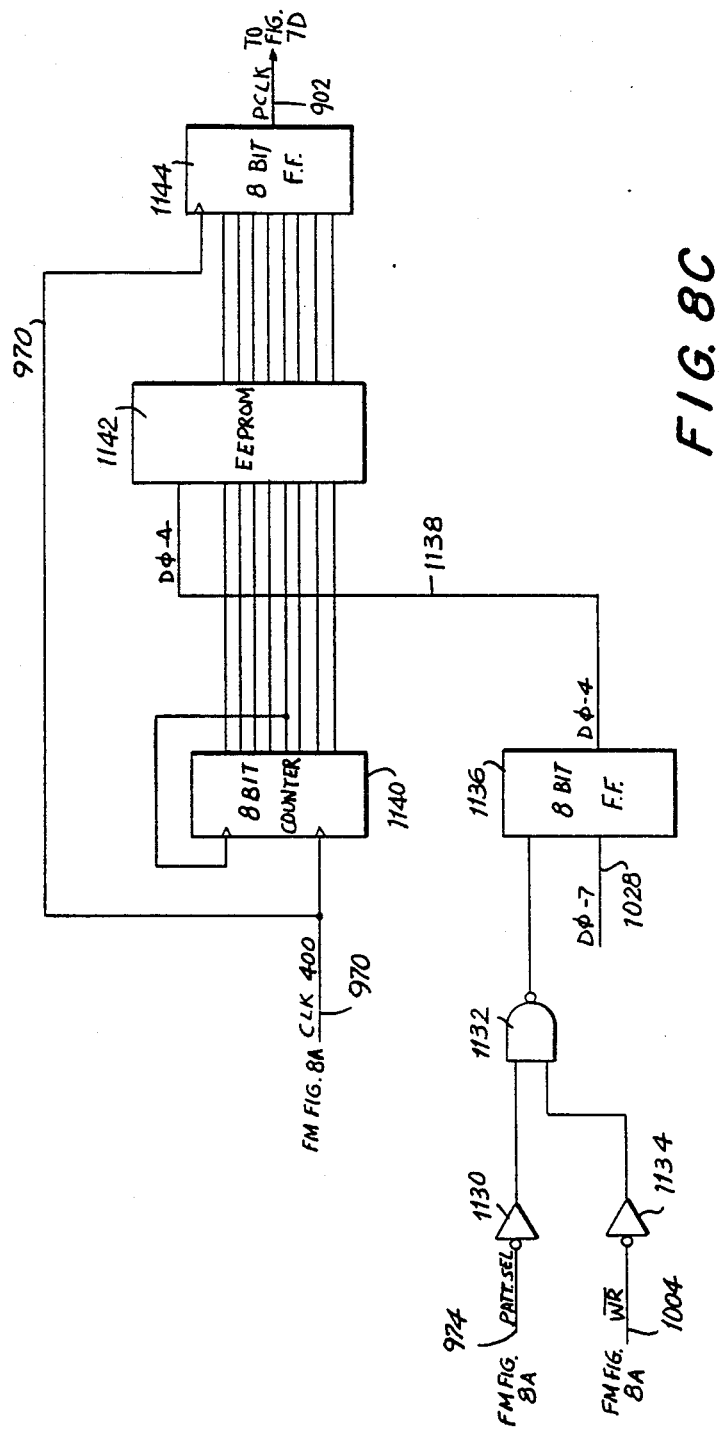

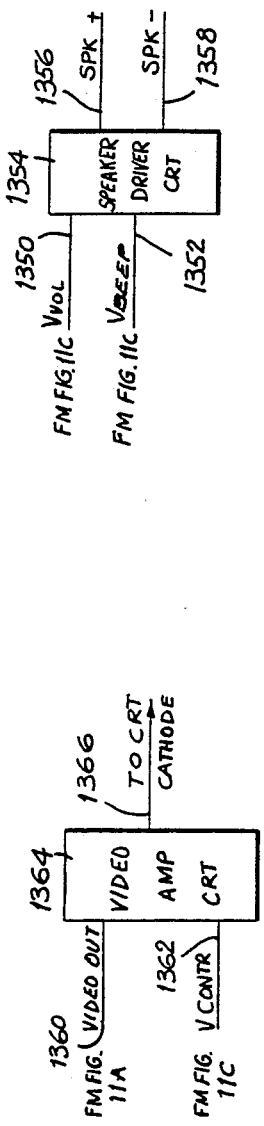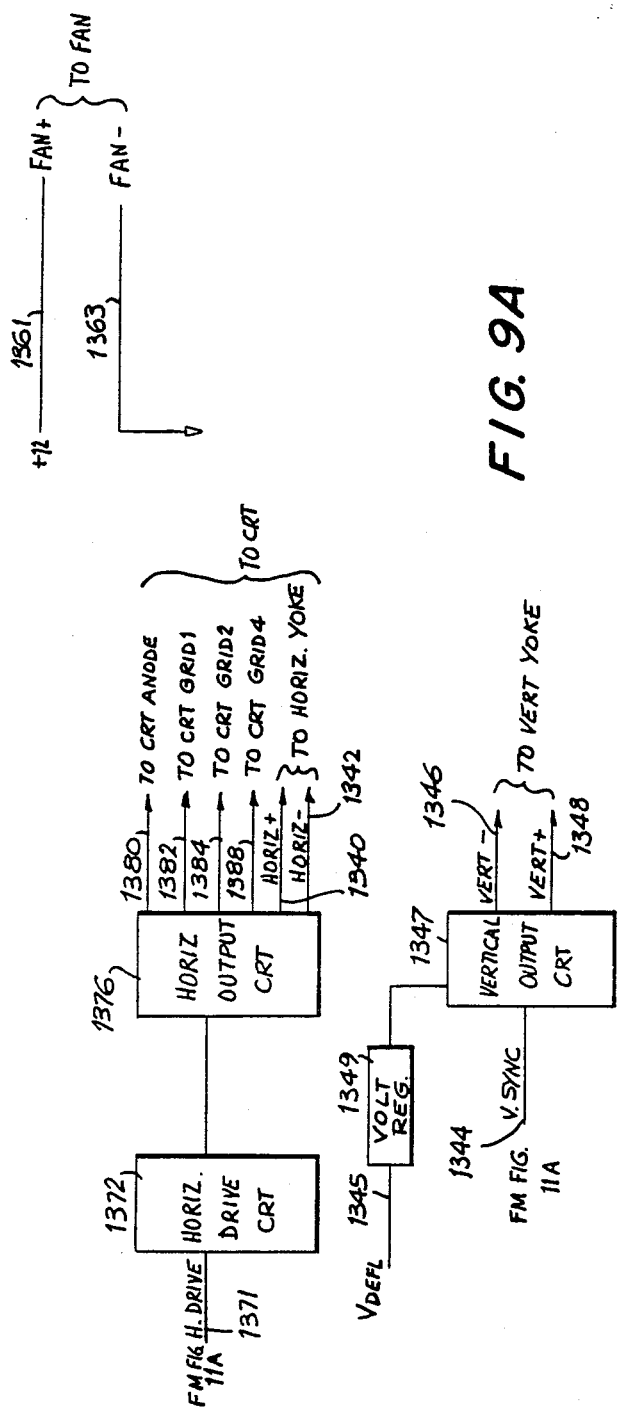
FIG. 9A

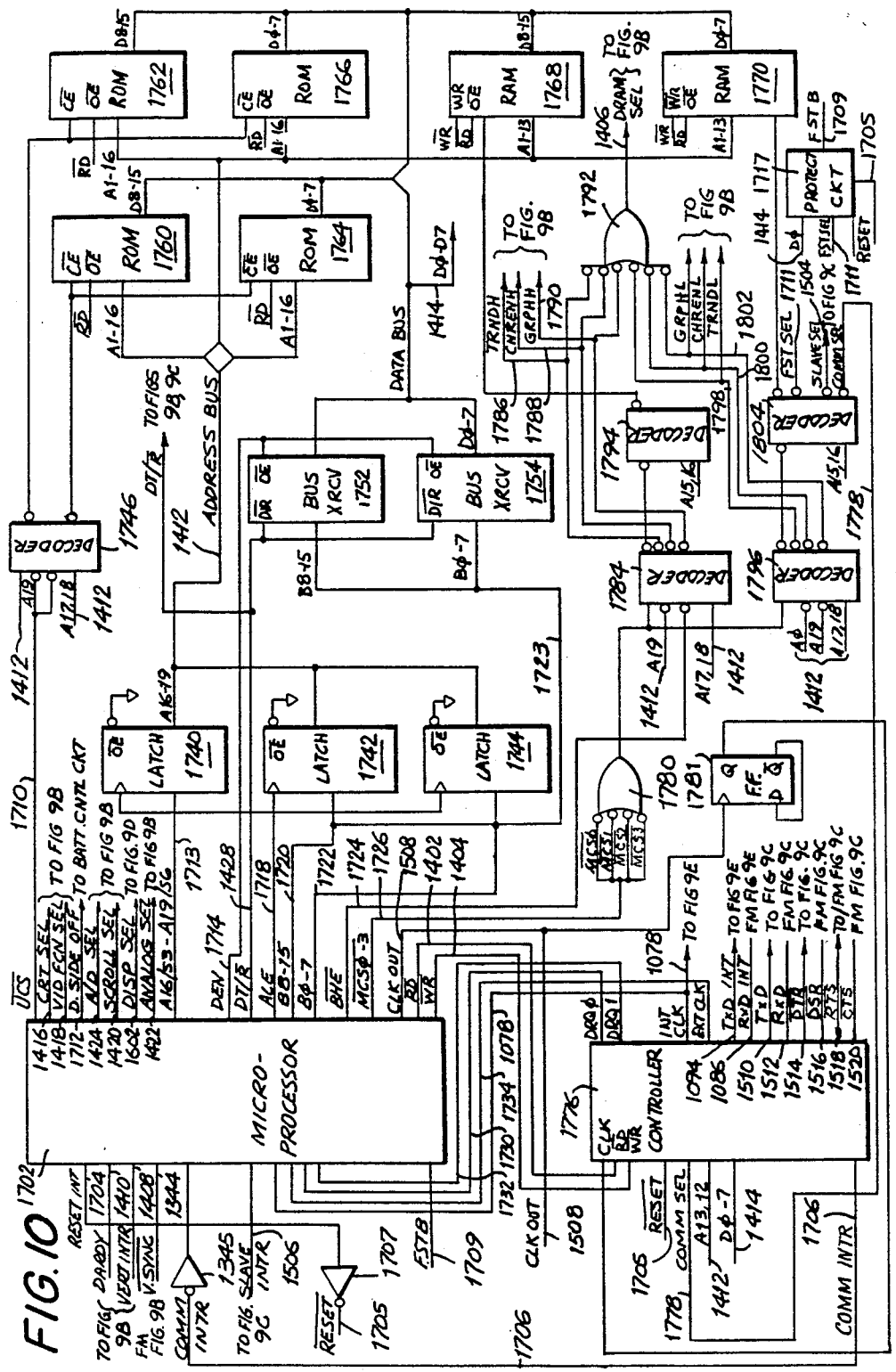

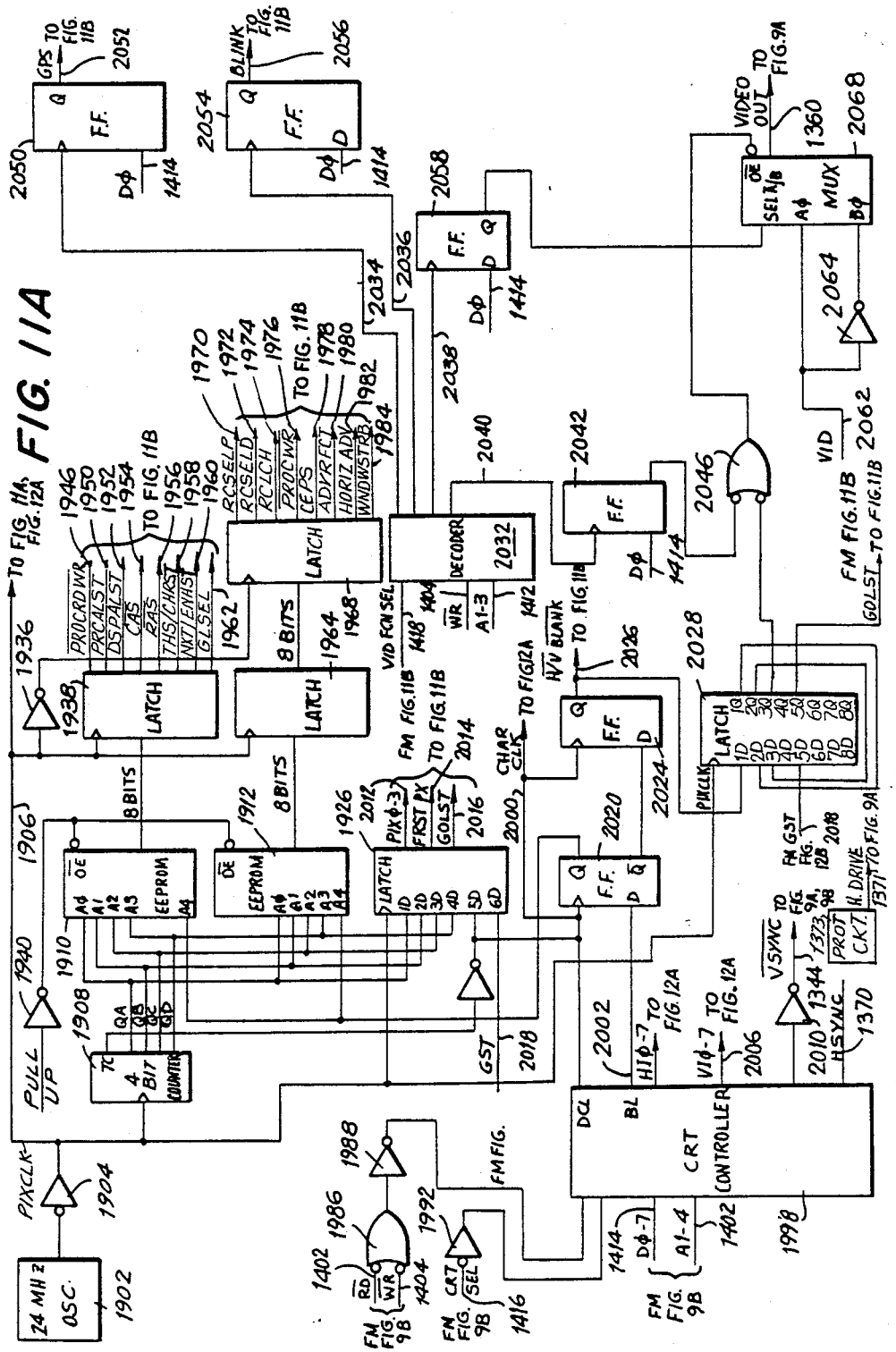

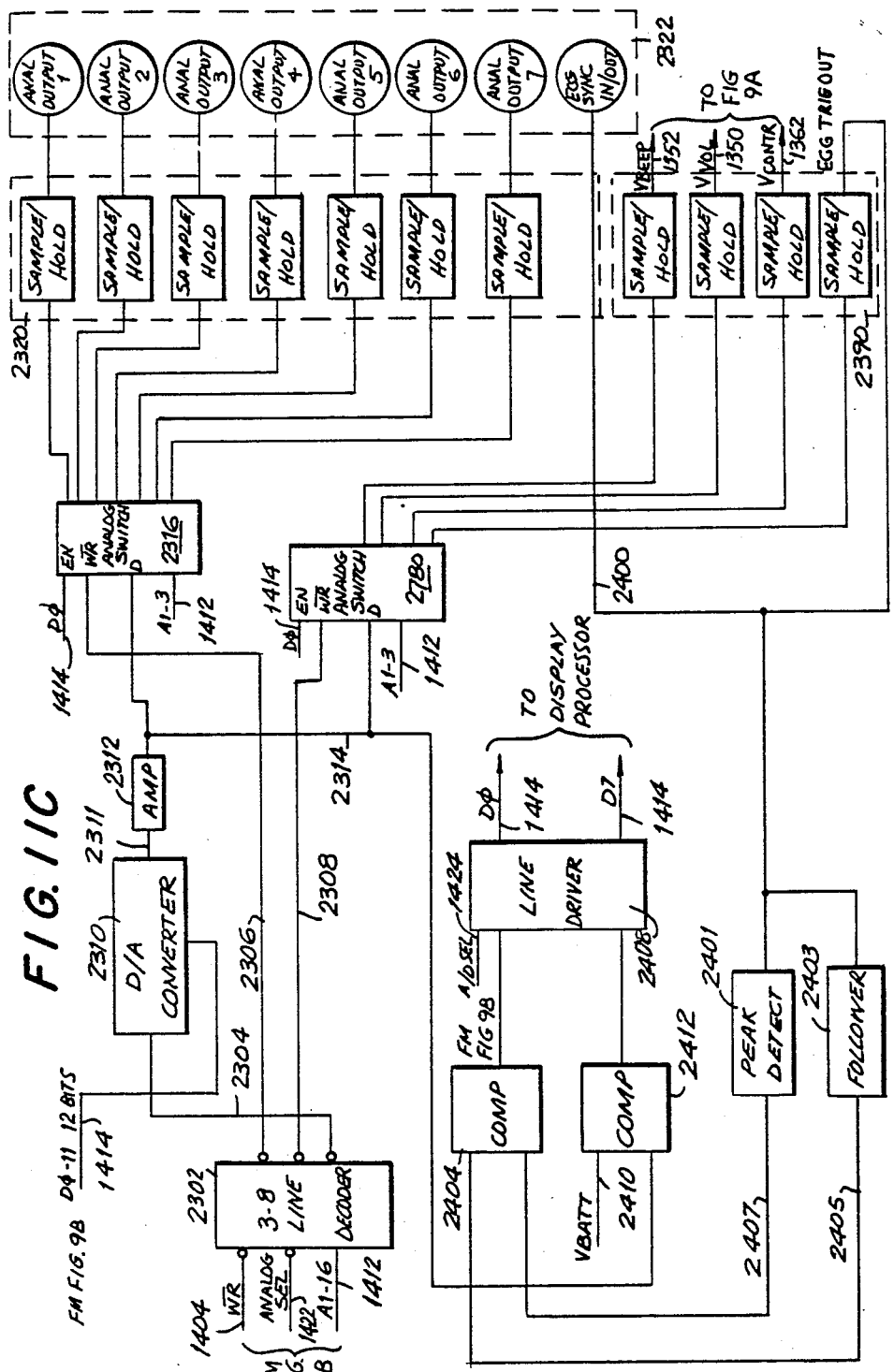

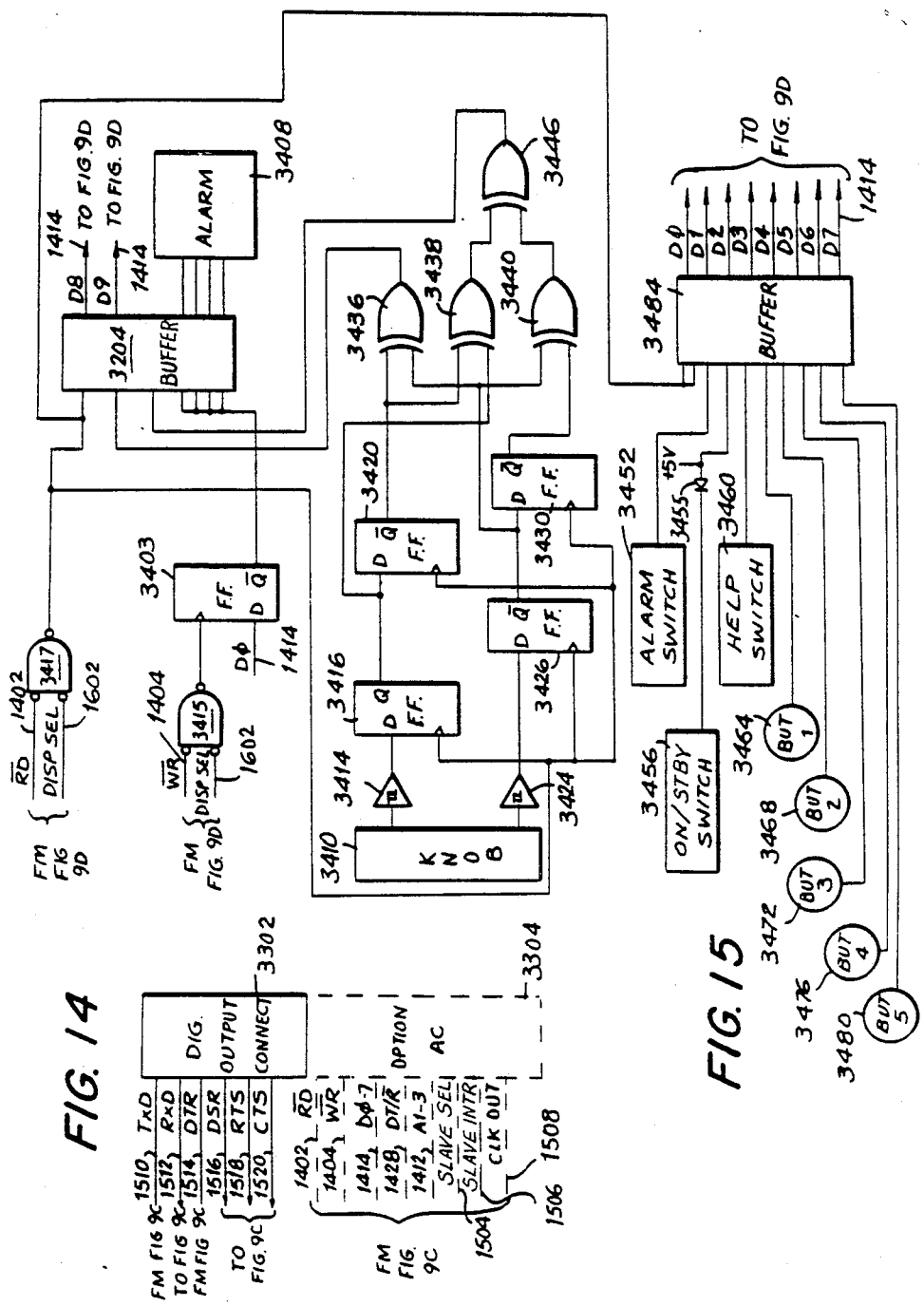

MULTICHANNEL GAS ANALYZER AND METHOD OF USE

This is a continuation-in-part patent application of Ser. No. 922,043, filed Oct. 10, 1987, now U.S. Pat. No. 4,817,013.

TECHNICAL FIELD

The present invention relates to systems for measuring the partial pressures of constituent gases in a gas stream. More specifically, the invention relates to improved multichannel gas analyzer systems used to measure the partial pressures of constituent gases in respiratory gas streams and display representative gas information on a CRT display.

BACKGROUND

During surgery, anesthetized patients are usually intubated. Measurement of respiratory gases is desirable when a patient is mechanically intubated through an endo-tracheal tube. An analysis of the inhaled and exhaled gas mixture provides information about the patient's ventilation.

Carbon dioxide ($CO_2$), nitrous oxide ($N_2O$) and the anesthetic agent are the constituent gases of most interest in measuring respiratory gas streams.

It is well known that $CO_2$ in the bloodstream equilibrates rapidly with $CO_2$ in the lungs. Hence, the partial pressure of the $CO_2$ in the lungs approaches the amount in the blood during each breath. Accordingly, the $CO_2$ content at breath's end, termed end-tidal $CO_2$, is a good indication of the blood $CO_2$ level.

Abnormally high end-tidal $CO_2$ values indicate that an insufficient amount of $CO_2$ is being transported away from the bloodstream through the lungs, i.e., inadequate ventilation. Conversely, abnormally low end-tidal $CO_2$ values indicate poor blood flow to the tissues, inadequate $CO_2$ transport through the lungs, or excessive ventilation.

Mass spectrometers are used for measuring the partial pressure of respiratory gases, for example, in operating room suites in which one spectrometer is shared by many rooms. Mass spectrometers have the advantage of measuring a multiplicity of gases; however, the disadvantages are their cost, maintenance and calibration requirements, slow response time, and noncontinuous measurement.

Gas analyzers using non-dispersive infrared spectrophotometry are also used for partial pressure gas measurement. While these analyzers are less expensive than mass spectrometers and continuously measure partial gas pressure, their disadvantages are poor response time and difficulty in calibration.

Prior art non-dispersive infrared gas analyzers include features for making $CO_2$ and $N_2O$ cross channel detection, temperature, and collision broadening corrections to their partial gas pressure measurements. Some of these corrections are made automatically by the analyzers while others are made manually by the operator.

Non-dispersive infrared gas analyzers generally have two configurations. The first, and most common, is the sampling or side-stream type. This type diverts a portion of the patient's respiratory gas flow through a sample tube to the infrared analyzer.

The second type mounts on the patient's airway and uses a portion of the airway as the sample chamber. This type is frequently occluded by the mucus and moisture in the patient's airway and its bulk on the airway can affect the patient's breathing.

Both infrared gas analyzer configurations have small absorption levels by the constituent gases which lead to small signals and stability problems.

Increasing the analyzer's sample chamber size improves the small signal and stability problems; however, it also increases the response time. Increasing the gas flow rate through the analyzer improves the response time, but occlusions are more frequent and the patient's normal ventilation volume is impaired.

In this regard, neonates require sample flow rates equal to or less than 50 cc/minute. However, neonates also require the analyzer's response time to be compatible with breath rates well in excess of 60 breaths per minute. These conditions equate to a response time of less than 100 milliseconds.

Another disadvantage of infrared gas analyzers is that they require frequent calibration for proper operation. Factors affecting calibration of the optical bench portion of a gas analyzer include manufacturing tolerances relating to the sample cell dimensions (particularly thickness); the brightness of the infrared sources and sensitivity of the photodetectors; temperature; barometric pressure; and the accumulation of dirt or moisture in the optical bench gas pathways.

Changes in the optics and electronic circuitry over time require recalibration of infrared gas analyzers. Careful construction of the optics and electronic circuitry minimizes the number of calibration adjustments needed and the period between recalibration. Hence, interchangeability of the optical bench of an analyzer has not heretofore been practical because of the need for recalibration when the optical bench is connected to the analyzer.

Calibration of infrared gas analyzers is accomplished by various electronic circuit adjustments to correct for variations in sample chamber geometry as well as variations and drift of various sensing components.

Calibration usually requires taking the analyzer out of service and passing standard gases through it, in the presence of which the various adjustments are made. Another calibration method is to make a "zero gas" reading for the optical bench and adjust the analyzer's amplifier so that the analyzer's output actually reads zero. A still further method uses a reference cell filled with a non-absorbing gas or a reference filter having a wavelength at which no absorption takes place to stabilize the zero setting of the analyzer.

Prior art non-dispersive infrared gas analyzers also include some automatic calibration features. However, further operator controlled calibration procedures are required before the analyzers are ready for use.

The present invention overcomes these and other problems of prior infrared gas analyzers as will be set forth in the remainder of the specification.

SUMMARY OF THE INVENTION

The present invention is an improved nondispersive infrared gas analyzer system for removing a respiratory gas stream from a patient, analyzing the gas stream, and displaying information about detected gases of interest.

The system includes a patient airway adapter which is used to remove a respiratory gas stream from the patient. The airway adapter has valving which allows for backflushing of the airway adapter inlet filter without reversing the flow through the sample gas tube used for drawing a respiratory gas stream through the system.

The patient module of the system includes an optical bench with associated circuitry. This circuitry generates signals representative of the partial pressures of $CO_2$ and $N_2O$ present in a respiratory gas stream transiting a gas pathway, the reference optical path, the temperature within the optical bench, and the pressure within the gas pathway.

The system pump module to a large extent controls system pneumatics. The module has means to draw a respiratory gas stream through the optical bench gas pathway for measurement of $CO_2$ and $N_2O$. The module also has means for measuring the flow rate of the gas stream through the optical bench gas pathway. The pump module backflush pump provides an air stream to the patient airway adapter for clearing its filter should it become occluded, for example, with mucus. The backflush air steam is supplied to the airway adapter for filter cleaning without the possibility of backflushing any virus or bacteria, for example, contained in gas pathway or the sample tube back into the patient. Two valves in the pump module redirect the respiratory gas stream through an external device for measurement of other constituents of interest in the gas stream when configured to do so. The module's diagnostic valve together with other valves, the sample pump, and the flow sensor are used to test the fluid-tight integrity of the gas pathway.

With respect to system pneumatics, the patient module includes a zero valve, which when properly configured is used with the pump module to supply scrubbed room air to the optical bench to make zero gas readings. A backflush valve in the patient module controls the flow of the backflush air stream to the patient airway adapter.

Analog input circuitry is electrically connected to the patient module including the optical bench. This circuitry receives the signals output from the optical bench and other patient module circuits. Analog input circuitry processes these signals and among other things converts them from analog to digital signals. The analog input circuitry then outputs the digital signals to the analog processing circuitry.

Analog processing circuitry, which includes a microprocessor, performs calculating functions. The results are output signals indicative of the partial pressure of $CO_2$ and $N_2O$ corrected for temperature, pressure in the gas pathway, collision broadening, cross-correction, and characterization. These signals along with those for the measured values of flow rate, pressure, and temperature are output to the display section of the system.

Display section circuitry, according to its programming, processes the signals output from the analog processing circuitry. The signals output from display section circuitry drive a CRT for display of graphics and characters representative of the partial pressures of the gases of interest and other measured values from the patient module.

The optical bench has two optical detection channel assemblies for measuring $CO_2$ and $N_2O$ in the respiratory gas stream and the reference optical path associated with the $CO_2$ and $N_2O$ detection channel assemblies. The bench continuously measures these gases at a rate which allows separate analysis of the inspired and expired gas mixtures. The optical bench circuitry preliminarily processes the signals output from the gas detectors and other detectors such as a pressure measurement sensor and a temperature measurement sensor.

The two optical detection channel assemblies and the connected detection circuitry are incorporated in the optical bench which is part of the small patient module. The patient module connects to a larger apparatus constituting the remainder gas analyzer system.

A double lumen tube, preferably one yard long or less, connects the patient module to a sidestream type patient airway adapter. The double lumen tube comprises a sample tube and backflush tube. A filter in the airway adapter blocks liquids, such as water or mucus, present in the patient's airway from entering the sample tube and, accordingly, the optical bench. The walls of the sample tube absorb water vapor condensing on them and evaporate it into the atmosphere which constitutes one-way water vapor transmission from within the sample tube. An optical bench entrance filter provides redundant protection of the optical bench gas pathway.

A flow shaper at the entrance of the optical bench gas pathway reshapes the sample tube gas flow cross-section from round to rectangular. In the optical bench gas pathway, the gas stream passes through the $CO_2$ and $N_2O$ detection channel assemblies in succession as it transits the gas pathway.

After leaving the optical bench gas pathway, the gas stream enters an absolute-type pressure transducer. The gas stream then leaves the absolute-type pressure transducer and enters the pump module. In this module the gas stream passes through the flow sensor and the sample pump. After leaving the pump module, the gas stream enters a scavenging tube and is exhausted from the system.

The $CO_2$ and $N_2O$ detection channel assemblies are configured to measure the amount of $CO_2$ and $N_2O$ in the respiratory gas stream, respectively, and measure the reference optical path associated with each assembly. The optical paths of the $CO_2$ and $N_2O$ detection channel assemblies each contain the gas pathway and contain respectively the $CO_2$ reference cell and the $N_2O$ reference cell. The reference cells can be filled, for example, with room air.

The detection channel assemblies include sapphire windows that replace opposing wall sections of the reference cell and the gas pathway in the assembly's optical path. An infrared light source is disposed behind one of the windows and a source aperture is disposed adjacent the opposing window. A detector aperture is disposed spaced away from the source aperture. Both apertures have openings that align with the optical path through the reference cell and gas pathway. The two apertures shield the optical paths from ingress of background infrared light.

A chopper wheel, common to the two detector channel assemblies, rotates in a plane between the source and detector apertures. The chopper wheel chops the infrared light passing through the openings in the source aperture aligned with the reference cell and gas pathway at a predetermined frequency. The chopped light passes through openings in the detector aperture aligned with the reference cell and gas pathway to the remaining portions of the assembly.

Adjacent an opposite side of the detector aperture is a narrow-band infrared filter. The filter is aligned to receive light that has passed through either the reference cell or the gas pathway.

A lead selenide detector is disposed on the other side of the infrared filter. The detector is aligned to receive light that has passed through either the reference cell or the gas pathway.

The chopper wheel together with the detection channel circuitry generate waveform patterns to control the timing and position of certain events during a timing cycle. These waveform patterns are used, among other things, for the synchronous detection and demodulation of the $CO_2$ and $N_2O$ gas and $CO_2$ and $N_2O$ reference signals output from the respective detectors representative of the partial pressures of these gases.

The optical bench circuitry includes an electrically erasable programmable read-only memory (EEPROM) which stores characterization information for the specific optical bench. The characterization information corrects optical bench measurements for system component performance that deviates from ideal theoretical performance. The characterization information obviates the need for calibration of the optical bench. Characterization information includes coefficients for temperature, collision broadening, cross-correction, span factor, offset for a system component, and pressure. Span factor is for translating the output voltage of the a component into desired parameter, such as pressure. Offset is to correct an instrument's readings to zero. Characterization information is used by the analog processing circuitry and the display circuitry in carrying out signal processing functions.

The analog input circuitry and the analog processor circuitry process the analog signals generated by the optical bench circuitry. The processed signals, now digital, are transmitted to the display section. The display section processes the signals for display on a CRT.

The main circuits of the display section are the display processor circuitry and pixel circuitry. The display processor circuitry bi-directionally communicates with the analog processor circuitry and controls the pixel circuitry. This control results in driving the CRT to display both the fixed characters and scrolled information, e.g., a capnogram.

Preferably, the CRT displays numerical and graphical data. The numerical data normally displayed are the inspired and expired values for $CO_2$ and $N_2O$, and respiration rate. The graphical data normally displayed can be the $CO_2$ waveform. This waveform is an indication of the patient's respiratory cycle. Superimposed, for example, on the $CO_2$ waveform are the transition points between inspiration and expiration, and between expiration and inspiration. These points are marked with an "I" and an "E", respectively. The "I" and "E" markings provide the physician with the locations of selected transition points in both normal and abnormal capnograms.

An object of the present invention is to provide an apparatus and method for improved measurement of the partial pressure of respiratory gases.

Another object of the present invention is to provide an improved apparatus and method for measurement of the partial pressures of gases of interest in a patient's respiratory gas stream with a rapid response time of less than 100 milliseconds and a sample flow rate less than or equal to 50 cc/min.

A further object of the present invention is to provide an apparatus capable of self characterization without calibration.

An even further object of the present invention is to provide an improved apparatus in which the optical bench portion of a gas analyzer can be interchanged without the need to recalibrate the system before use.

Another object of the present invention is to provide a system for displaying the partial pressures of gases of interest in a patient's respiratory gas stream, scrolling waveforms across the display screen and marking inspired and expired transition points of a patient's breathing cycle.

Yet another object of the present invention is to provide on apparatus with the "instant on" feature that permits measurement of the partial pressures of gases of interest in a patient's respiratory gas stream immediately after the apparatus is turned on.

Another object of the present invention is to provide an optical bench in which the temperature of the optical bench is not controlled.

A still further object of the invention is to provide an improved apparatus which has an patient airway adapter and backflush system which insures that a patient will not be contaminated by virus or bacteria, for example, existing in the optical bench when a backflush is performed to clear occlusions of the airway adapter filter due to mucus or other material.

These and other objects of the invention will be described more fully in the remaining portions of the specification.

BRIEF DESCRIPTION OF THE DRAWINGS

FIG. 1 is a block diagram of the multichannel gas analyzer system of the present invention.

FIG. 2A is a cross-sectional view of the connector for connecting a double lumen tube to the patient airway adapter of the multichannel gas analyzer system of the present invention.

FIGS. 2B and 2C are two different cross-sectional views of the patient airway adapter of the multichannel gas analyzer system of the present invention.

FIG. 3B shows the optical detection channel assemblies with their components shown in an exploded view.

FIG. 3C shows the $CO_2/N_2O$ detection channel assembly of the optical bench of the multichannel gas analyzer system of the present invention.

FIG. 4A is a block diagram of the pneumatics of the multichannel gas analyzer system of the present invention.

FIG. 5B shows schematic diagrams of drive circuits in the optical bench for various components associated with control of the pneumatics.

FIG. 6A is a top view of the chopper wheel of the optical bench of the multichannel gas analyzer system of the present invention.

FIG. 6B is a top view of the chopper wheel of FIG. 6A associated with selected portions in the optical bench of the multichannel gas analyzer system of the present invention.

FIG. 7A-7D comprise a schematic diagram of the analog input circuitry of the multichannel gas analyzer system of the present invention.

FIGS. 8A-8C comprise a schematic diagram of the analog processing circuitry of the multichannel gas analyzer system of the present invention.

FIGS. 9A-9E comprise a schematic diagram of the circuitry on the motherboard of the multichannel gas analyzer system of the present invention.

FIG. 10 is a schematic diagram of the display processor circuitry of the multichannel gas analyzer system of the present invention.

FIGS. 11A-11C comprise a schematic diagram of the pixel circuitry of the multichannel gas analyzer system of the present invention.

FIG. 14 is a schematic diagram of the digital output section of the display section of the multichannel gas analyzer system of the present invention.

FIG. 15 is a schematic diagram of the system controls and alarms for the multichannel gas analyzer system of the present invention.

DETAILED DESCRIPTION OF THE PREFERRED EMBODIMENTS

Figure 3A:
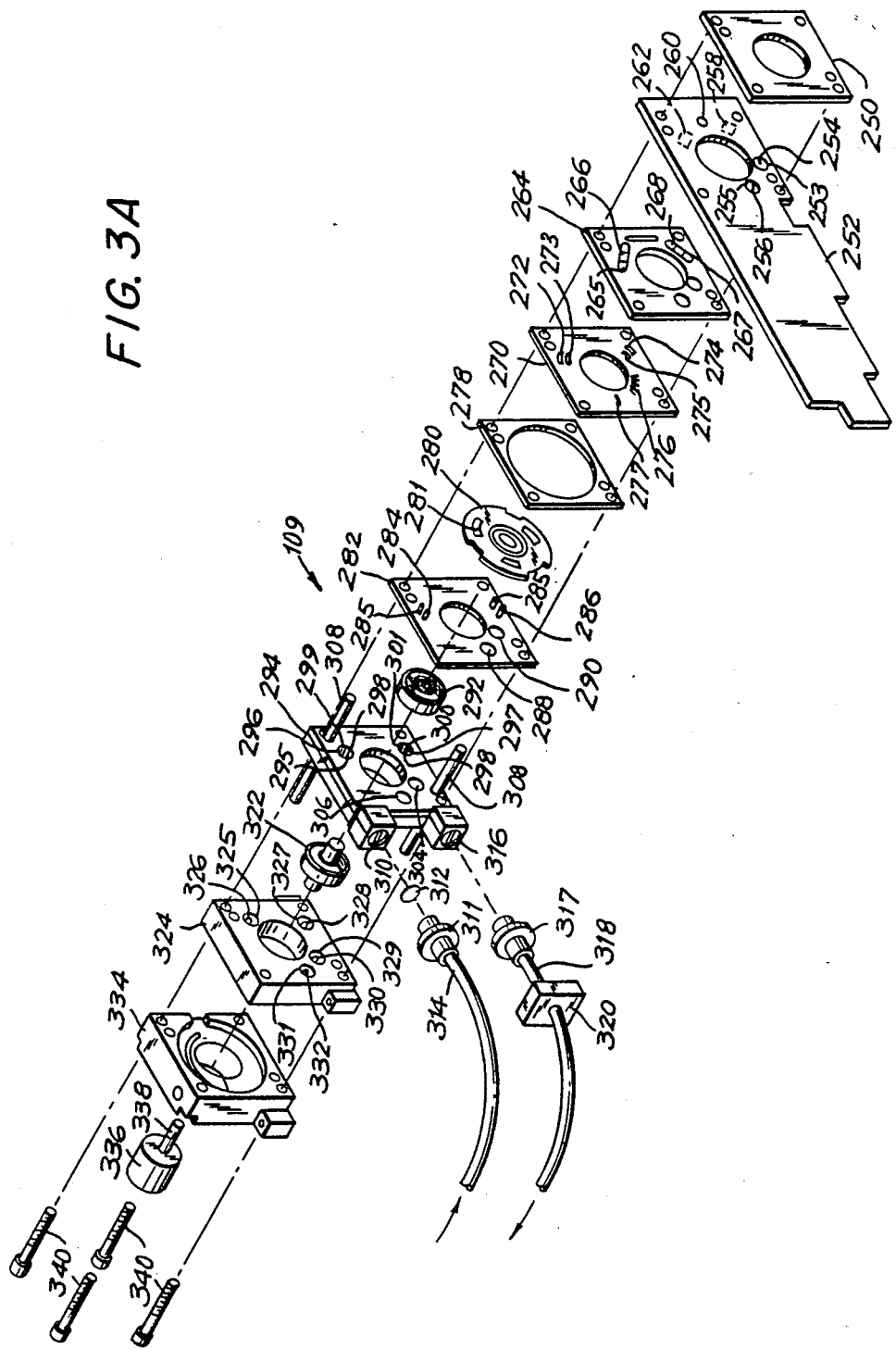
FIG. 3A is an exploded view of the optical bench of the multichannel gas analyzer system of the present invention.

The present invention is an improved multichannel gas analyzer system for measuring the partial pressures of gases of interest in a respiratory gas stream. The analyzer system also displays numerical and graphical information about detected gases.

The figures refer to electronic components, or circuitry which may consist of a group of components, that carry out known specific functions. Those components or circuit elements that are well known by those skilled in the art will be referred to generally by their common names or functions and are not explained in detail.

Analog section 102 and patient airway adapter 106 are described generally and in detail in discussing FIGS. 2A through 8C. Display section 104 is described generally and in detail in discussing FIGS. 9A through 15.

FIG. 1 is a schematic diagram of the multichannel gas analyzer system of the present invention. The system comprises patient airway adapter 106, analog section 102, and display section 104. Analog section 102 detects and measures certain constituent gases in a respiratory gas stream. This section also detects and measures other physical properties which affect the determination of the partial pressures of constituent gases, e.g., $CO_2$ and $N_2O$. The measured values for $CO_2$, $N_2O$, and the other physical properties are combined to calculate the "real" partial pressure of $CO_2$ and $N_2O$. The "real" partial pressures of these gases are corrected for barometric pressure, optical bench pressure, temperature, collision broadening, cross-correction, and characterization of the detection circuitry and other detection components.

The calculated values for the partial pressures of $CO_2$ and $N_2O$ are output from analog section 102 in digital form to display section 104. Analog section 102 also transmits measured values for flow rate, pressure, and temperature to the display section.

Display section 104 processes the analog section signals. The $CO_2$ and $N_2O$ signals are processed for display on the CRT as numeric characters. The display section also processes at least the $CO_2$ signals for graphic display, for example, as a scrolling capnogram. The display section processes the pressure, flow rate, and temperature signals for display or as historical data.

The display section has system controls for operator interface. These controls select system operation and choice of screen displays. The display section also has both digital and analog output ports for communicating with peripheral equipment. The display section includes visual and audible alarms to indicate alarm conditions or improper system operation.

The analog processor circuitry can receive input signals from another optical bench for processing for display on the CRT. The other optical bench is dedicated to measurement of the partial pressures of other gases of interest in the respiratory gas stream.

Analog section 102 comprises patient module 109 which includes optical bench 111 (whose electronics include optical bench circuitry 118); pump module 112; analog input circuitry 122; and analog processing circuitry 124.

Display section 104 comprises display processing circuitry 128; pixel logic circuitry 130 (which include analog outputs); digital outputs 140; speaker driver 152; alarm and knobs 144; 5-button panel 148; and display motherboard 137 (which includes a CRT driver). The powering system includes power supply 158, rectifier 160, and DC-DC converter 162.

Patient airway adapter 106 and tubes 172 and 174 (which form a double lumen tube that connects adapter 106 and patient module 109) are not part of analog section 102. The airway adapter can be detachably fixed to tubes 172 and 174. The adapter and tubes, besides being used in-part as a gas pathway from the patient to the patient module, provides a novel means for backflushing the adapter without risk of contaminating a patient with virus or bacteria that may exist in the optical bench gas pathway or sample tube 174.

Measurement accuracy increases the closer to the patient gas detection is made. For this reason, the length of the double lumen is preferably one yard or less.

Referring to FIGS. 2A, 2B, and 2C, the double lumen tube, its associated connector, and patient airway adapter 106 will be described. The double lumen tube containing sample tube 174 and backflush tube 172 connects airway adapter 106 and patient module 109. The series of dots at 170 represent the outer cover which encases gas sample tube 172 and backflush tube 174.

The walls of the sample tube, preferably constructed of Nafion, absorb and then evaporate condensed water vapor in the tube. Nafion is commercially available from E. I. duPont de Nemours and Company, Wilmington, Del. Nafion is a trademark of E. I. duPont and Company, Wilmington, Del.

Connector body 178 has gripping members 180 which along with locking cap 176 secure outer cover 170 of the double lumen tube to connector body 178. Connector body 178 has annular bead 188 which assists in locking the connector body within airway adapter 106. 0-ring 190 is disposed in annular groove 186. 0-ring 190 is used to provide a fluid-tight seal between connector body 178 and airway adapter section 210.

Connector body 178 has central bore 182. Plug 184 is disposed in one end of the connector body and receives tubes 172 and 174. Plug 184 has separate openings for receiving backflush tube 172 and sample tube 174 therethrough.

The other end of central bore 182 has insert 192 disposed therein. Insert 192 has centrally disposed orifice 196 which connects to a larger diameter end opening 194. The end of sample tube 174 is disposed in orifice 196 so that it is in fluid communication with end opening 194.

Backflush tube 172 passes through plug 184 and is in fluid communication with central bore 182. Channels 198 and 200 are for fluid communication between central bore 182 and annular channel 201 in the end of connector body 178. Channel 201 is concentric with end opening 194. Accordingly, backflush tube 172 is in fluid communication with the end of the connector body.

FIGS. 2B and 2C show two different cross-sectional views of airway adapter 106. Accordingly, the following description applies to both figures.

Connector body 178 mates with section 210 of airway adapter 106. Section 210 has central cavity 212 which has disposed within it valve body 216 and valve member 226. Valve body 216 and valve member 226 are disposed on annular ledge 224 within cavity 212. Valve member 226 is disposed between valve body 216 and annular ledge 224.

Valve body 216 has centrally aligned nipple 217 on the side facing cavity 212 and centrally aligned nipple 219 on the opposite side. Orifice 218 extends through the center of the centrally aligned nipples. Concentric with nipple 217 is annular channel 220. Orifices 222 extend from the bottom annular channel 220 through the remaining thickness of valve body 216.

Valve member 226 has an opening in the center through which nipple 219 extends. In the valve's closed position, the edge of the opening in valve member 226 rests against the sides of nipple 219 and in cross-section forms an acute angles with the side of that nipple. This is necessary for proper operation of the valve.

Annular ledge 228 is fixed to the walls of opening 230 at the end nearest the valve. Hydrophobic filter 232 is disposed across opening 230 on the side of ledge 228 closest airway adapter section 238. Hydrophobic filter 232 can be fixed to annular ledge 228. However, in the preferred embodiment, annular ledge is not included and the filter is fixed to ledge 229. When annular ledge 228 is included, it seals the filter in place and prevents valve member 226 from contacting filter 232 when it is open and portions thereof move toward the filter.

Second section 238 of airway adapter 106 has opening 236 into which first section 210 is fixed. Section 238 has passage 240 through which respiratory gas to be sampled flows. Section 238 is usually disposed in the patient's airway.

When connector body 178 is inserted into cavity 212, annular bead 214 at the end of the cavity moves over annular bead 188 on connector body 178. Accordingly, annular bead 188 rests in annular depression 215. This locks the connector body within the airway adapter. 0-ring 190 rests against the interior wall of section 210 to seal against fluid leaks. End opening 194 of connector body 178 fits over nipple 217 of valve body 216. This places sample tube 174 in fluid communication with the respiratory gas flow in passage 240 through orifice 218 and filter 232.

When connector body 178 is locked in section 210, annular channel 201 in the end of connector body 178 is in fluid communication with annular channel 220 in valve body 216. Since orifices 222 are in fluid communication with passage 240 through valve member 226 and filter 232, backflush tube 172 is in uni-directional fluid communication with passage 240 of section 238.

In normal sampling operations, sample pump 358 (FIG. 4A) in the pump module draws the gas sample through filter 232, orifice 218, and sample tube 174. Valve member 226 prevents the sample gas from entering backflush tube 172.

When filter 232 becomes occluded with mucus or other material requiring a backflush to clear it, zero valve 376 (FIG. 4A) has its flow configuration changed so that the flow through sample tube 174 is cut off. Backflush pump 394 is activated and pumps filtered room air at a desired rate into backflush line 172 toward airway adapter 106. The filtered room air passes from backflush tube 172 through central bore 182, channels 198 and 200, and into annular channel 201 in the end of connector body 178. From the connector body, the backflush air enters annular channel 220 in valve body 216 and passes through orifices 222 in valve body 216. When the pressure of filtered room is great enough, valve member 226 lifts from its seat against the sides of nipple 219 allowing the filtered room air to clear filter 232 of the obstruction. Hence, the airway adapter can be backflushed without the possibility of backflushing any contamination that exists in the sample tube or the optical bench gas pathway into the patient when backflushing filter 232. Preferably, filter 232 is constructed of expanded PTFE with a 1 micron pore size.

The airway adapter has been described as involving the joining two separate sections, specifically, sections 210 and 238. However, it is understood that the airway adapter can be of unitary construction.

FIGS. 3A–3C show optical bench 111. Referring to FIG. 3A, an exploded elevation view of the optical bench is shown. Each of the boards, blocks, or plates has a centrally disposed opening to accommodate the chopper wheel and its associated driving assembly; therefore, those openings will not be discussed separately.

End plate 250 forms the first end of the optical bench and is also a heat sink to dissipate heat generated in the optical bench.

Detector board 252 is disposed inward of end plate 250. The detector board has silicon photodiodes 254 and 256 fixed in openings 253 and 255, respectively, and lead selenide detectors 258 and 262, and thermistor 260 mounted on the board.

Photodiodes 254 and 256 detect the amount of infrared light illuminating them from LEDs in their respective optical paths. Detectors 258 and 262 detect the amount of infrared light illuminating them from infrared light sources in their respective optical paths. Thermistor 260 senses the optical bench temperature through resistance changes and conventional circuitry converts the resistance changes to a voltage. Preferably, the photodetectors are model OP9$\emptyset\emptyset$ commercially available from TRW Optron, Carrollton, Tex.; the lead selenide detectors are commercially available from OPTO Electronics, Inc., Santa Rosa, Calif.; and, preferably, the thermistor is model B43PB103K commercially available from Thermometrics, Metuchen, N.J.

Filter block 264 is disposed inward of detector board 252. The filter block has $CO_2$ optical filter 266 fixed in opening 265 and $N_2O$ optical filter 268 fixed in opening 267. The $CO_2$ filter and $N_2O$ filters are commercially available from Optical Coating Laboratories, Inc., Petaluma, Calif.

Detector aperture 270 is disposed inward of the filter block. The detector aperture has openings 272 and 273, and openings 274 and 275 for shielding against background light ingressing the $CO_2$ and $N_2O$ optical paths, respectively. Opening 272 is associated with the $CO_2$ reference optical path and opening 273 is associated with the $CO_2$ gas optical path. Opening 274 is associated with the $N_2O$ reference optical path and opening 275 is associated with the $N_2O$ gas optical path.

The series of closely spaced openings indicated generally at 276 are for shielding the timing track optical path against ingress of background light. The single opening 277 is for shielding the position track optical path against the ingress of background light.

Spacer 278 serves the conventional purpose of a spacer. It spaces apart detector aperture 270 and source aperture 282 so that chopper wheel 280 can rotate in a plane between the two apertures.

The chopper wheel assembly comprises chopper wheel 280, bearing 292, jack shaft and bearing 322, and motor 336 with flexible coupling shaft 338. Preferably, the motor is model 2312-910-21141-010 commercially from Maxon Precision Motors, Palo Alto, Calif.

The chopper wheel will be discussed fully when describing FIGS. 5A, 6A, 6B, and 6C.

Source aperture 282, like detector aperture 270, shields the $CO_2$ and $N_2O$ optical paths against ingress of background light. Openings 283 and 284 are the openings for the $CO_2$ reference optical path and the $CO_2$ gas optical path, respectively. Openings 285 and 286 are for the $N_2O$ reference optical path and the $N_2O$ gas optical path, respectively. Opening 290 is associated with the timing track optical path; and opening 288 is associated with the position track optical path.

Block 294 contains respiratory gas pathway 298 and the reference gas cells. Block 294 has also gas inlet 310 and outlet 316. Preferably, gas pathway 298 is rectangular in cross-section. The gas pathway will be discussed in detail when describing FIG. 3B.

Block 294 has opening 306 associated with the position track optical path and opening 304 associated with the timing track optical path. Block 294 has also alignment members 308 for proper alignment of the various component boards, blocks, and plates of the optical bench.

Block 294 has opening 299 into which sapphire window 295 is fixed. Although not shown here, sapphire window 342 is fixed in an opening on the other side of block 294. These sapphire windows form opposing walls of $CO_2$ reference cell 296 and gas pathway 298.

In like manner, block 294 has opening 301 into which sapphire window 297 is fixed. Although not shown here, sapphire window 344 is fixed in an opening on the other side of block 294. These sapphire windows form opposing walls of $N_2O$ reference cell 300 and gas pathway 298.

Associated with block 294 are inlet flow shaper 311, entrance line 314, and in-line filter 312, exhaust fitting 317, and exhaust line 318. Filter 312 is disposed at gas inlet 310. Flow shaper 311 and filter 312 reshape the incoming gas stream cross-section from round to rectangular. Exhaust fitting 317 is adapted to fit gas outlet 316. Preferably the entrance and exhaust lines are constructed of ethyl vinyl alcohol copolymers.

Pressure transducer 320 is disposed on exhaust line 318 for measuring the pressure in the gas pathway. The measured pressure value is used for correction of the detected gas signals.

Lamp block 324 has opening 325 in which IR source 326 is fixed, opening 327 in which IR source 328 is fixed, and openings 329 and 331 in which LEDs 330 and 332 are fixed, respectively. IR source 326 is associated with the $CO_2$ reference and sample gas optical path and IR source 328 is associated with the $N_2O$ reference and sample gas optical path. LED 330 is associated with the timing track optical path and LED 332 is associated with the position track optical path. Preferably the IR sources are model 4115-2, commercially available from Gilway Company, Woburn, Mass., and the LEDs are model SFH-487 commercially available from Siemens Components, Inc., Cupertino, Calif.

Motor block 334 is used to mount motor 336. Motor block 334 also serves as the second end of the optical bench. Bolts 340 are used to connect the various components, boards, blocks, and plates of the optical bench.

FIG. 3B shows half racetrack-shaped gas pathway 298 that is used for passing a respiratory gas stream through the optical bench. This figure shows in-part the elements of the $CO_2$ and $N_2O$ optical paths. These are IR sources 326 and 328, sapphire windows 342 and 295 associated with the $CO_2$ reference and $CO_2$ gas optical paths and sapphire windows 344 and 297 associated with the $N_2O$ reference and $N_2O$ gas optical paths, $CO_2$ reference cell 296 and $N_2O$ reference cell 300, a portion of chopper wheel 280, $CO_2$ optical filter 266 and $N_2O$ optical filter 268, and $CO_2$ detector 262 and $N_2O$ detector 258. These elements when combined form a majority of the $CO_2$ and $N_2O$ detection assemblies.

Optical filter 266 has a center frequency of 4.265 microns and a bandwidth of 2.0%. This coincides with the absorption band of $CO_2$. Optical filter 268 has a center wavelength of 4.50 microns with a bandwidth of 2.5%. This coincides with absorption band of $N_2O$.

Detectors 258 and 262 are lead selenide infrared detectors. Preferably, the detectors have a 3 mm. square active area.

Referring to FIG. 3A, the respiratory gas stream enters the optical bench at gas inlet 310 (FIG. 3A) from flow shaper 311 and passes through in-line filter 312. The entering gas flow has a circular cross-sectional shape. Flow shaper 311 and in-line filter 312 reshape the gas flow to the rectangular cross-sectional shape of gas pathway 298 without turbulence. Flow shaper 311 has an inlet with a circular cross-sectional shape and outlet with a rectangular cross-sectional shape that matches gas pathway 298. The center portion of the flow shaper makes a smooth transition from the circular to the rectangular cross-sectional shape. A longitudinal cross-section of the flow shaper reveals that the interior walls are either straight or curved. There is a pressure drop across in-line filter 312. This pressure drop assists in turbulence free reshaping of the cross-sectional shape of the gas stream. However, other configurations for the inlet to accomplish flow shaping without a filter may be used.

In-line filter 312 is preferably constructed of expanded PTFE with a 1 micron pore size. The filter prevents foreign material from entering the gas pathway.

The half racetrack-shaped of gas pathway 298 accommodates the use of chopper wheel 280 for signal chopping. If other chopping methods are used, gas pathway 298 may have other shapes.

FIG. 3C depicts the $CO_2$ and $N_2O$ detection channel assemblies in the optical bench. The reference numbers in FIG. 3C are for the $CO_2$ detection channel assembly. The $CO_2$ and $N_2O$ detection channel assemblies are substantially identical. Hence, in the description of FIG. 3C, the $N_2O$ detection assembly component reference numbers follow in parentheses those for the $CO_2$ detection assembly where appropriate.

IR source 326 (328) is fixed within opening 325 (327) of lamp block 324. Disposed adjacent to the lamp block is block 294. Block 294 has opening 299 (301) into which sapphire window 295 (297) is fixed and opening 343 (not shown for $N_2O$) into which sapphire window 342 (344) is fixed. The sapphire windows form part of the walls of $CO_2$ reference cell 296 (300) and sample gas pathway 298.

Disposed adjacent to block 294 is source aperture 282. Source aperture 282 has opening 283 (285) aligned with the $CO_2$ reference optical path and opening 284 (286) aligned with the $CO_2$ gas optical path.

Spaced away from the source aperture is detector aperture 270. The detector aperture has opening 272 (274) aligned with the $CO_2$ reference optical path and opening 273 (275) aligned with the $CO_2$ gas optical path.

Disposed between source aperture 282 and detector aperture 270 is chopper wheel 280. Chopper wheel rotates in a plane between the source and detector apertures. Opening 281 in chopper wheel 280 is shown aligned with the $CO_2$ gas optical path. Chopper wheel 280 also has openings that align with the $CO_2$ reference optical path which will be described subsequently.

Filter block 264 is disposed adjacent an opposite side of detector aperture 270. Optical filter 266 (268) is fixed within opening 265 (267) of the filter block. Optical filter 266 (268) is in the $CO_2$ reference optical path and the $CO_2$ gas optical path.

Detector board 252 is disposed adjacent filter block 264. $CO_2$ detector 262 (258) is fixed to the detector board. Detector 262 (258) is in the $CO_2$ reference optical path and the $CO_2$ gas optical path.

Preferably, the optical path lengths of gas pathway 298, $CO_2$ reference cell 296, and $N_2O$ reference cell 300, as part of the $CO_2$ and $N_2O$ gas optical paths and the $CO_2$ and $N_2O$ reference optical paths, respectively, are 0.1 inches.

FIG. 4A shows the pneumatic system which includes pump module 112 and certain components and interconnected tubing in the patient module 109. The pneumatic system's purpose is to draw a respiratory gas stream through the gas pathway at the preferred rate of 50 cc/min., backflush the system with filtered room air at a flow rate of approximately 300 cc/min., draw scrubbed room air at a 50 cc/min. flow rate through the gas pathway for making zero gas measurements, and provide means for determining whether or not the gas pathway is fluid-tight.

The main components of pump module 112 includes flow sensor 356, sample pump 358, external valve 1, 424, external valve 2, 436, backflush pump 394, $CO_2$ scrubber 410, and diagnostic valve 412. The main components of the pneumatic system in patient module 109 are pressure sensor 374, zero valve 376, and backflush valve 382.

In normal operation, sample pump 358 is used to draw the respiratory gas stream through the patient module so that optical bench 111 can make measurements of the partial pressures of $CO_2$ and $N_2O$ in the respiratory gas stream. SAMPLE PUMP+ line 360 and SAMPLE PUMP− line 362 are the power lines for sample pump 358. The voltage across these lines controls the speed of this pump. Preferably, the pump will run at a speed sufficient to maintain a 50 cc/min. respiratory gas flow rate through the gas pathway comprising sample tube 174, patient module sample gas pathway 372, optical bench gas pathway 298 (FIG. 3), and pump module sample gas pathway 368. When this is the case, sample pump 358 is activated and a respiratory gas stream is drawn through airway adapter 106 and into sample tube 174. The gas then passes through filter 384 in connector 352 and through filter 386 across the inlet of the patient module sample gas pathway.

The respiratory gas stream proceeds through zero valve 376, which is configured for receiving the flow from sample tube 174. As it moves along the patient module sample gas pathway, it passes through optical inlet filter 312 and enters the optical bench gas pathway 298 (FIG. 3) where measurements of the partial pressures of the gases of interest are made.

The respiratory gas stream leaves the optical bench and passes through pressure sensor 374. Pressure sensor 374 measures the pressure of the gas stream in the optical bench. The respiratory gas then flows through the remainder of patient module sample gas pathway 372 and enters pump module 112 through connector 370.

Once inside the pump module, the gas stream enters pump module sample gas pathway 368. First the gas stream passes through external valve 1, 424, and external valve 2, 436, configured for flow along pump module gas pathway 368 without redirection. After this, it passes through flow sensor 356 and sample pump 358. After leaving sample pump 358, the gas stream passes through connector 366 and enters a tube which carries the gas stream to a scavenging system.

When it is desired to make a zero gas reading, the direction of fluid flow through the zero valve is changed. During the time when zero gas readings are being made, barometric pressure readings are also made. The barometric pressure value is stored for use later in calculating the partial pressures on the gases of interest. Barometric pressure measurements are made with pressure sensor 374.

ZERO+ line 378 and ZERO− line 380 power zero valve 376. The voltage across these lines determines whether the zero value is configured to provide scrubbed room air from patient module zero gas pathway 404 or the respiratory gas stream from sample tube 174. Accordingly, the proper voltage is placed across ZERO+line 378 and ZERO−line 380 to cause zero valve to close off gas flow from sample tube 174 and open to the air flow in patient module zero gas pathway 404. Preferably, sample pump is powered to draw 50 cc/min. of scrubbed room air through the pneumatic system.

When zero valve 376 is so aligned, sample pump 358 is properly activated and draws the scrubbed room air through the patient and pump modules' sample gas pathways. During this time, zero gas readings are made. The purpose of making zero gas readings is to clear the analyzer electronics so subsequent gas readings will be accurate.

When zero gas readings are being made, room air is draw through filter 414 and two-way diagnostic valve 412. The use of diagnostic valve 412 will be described subsequently. After diagnostic valve 412, the room air enters $CO_2$ scrubber 410. The $CO_2$ scrubber prevents, for example, exhaled $CO_2$ from a system operator from entering the pneumatic system during zero gas readings.

Following the $CO_2$ scrubbing, the room air enters pump module zero gas pathway 408, goes through connector 406 and enters patient module zero gas pathway 404. After passing through zero valve 376, the scrubbed room air enters optical bench 111 where zero gas readings are made. Following this, the scrubbed room air goes through the remaining portions of the sample gas pathway in the patient and pump modules and enters the scavenging system.

During, or subsequent to, zero gas readings, or when it is determined that the patient adapter filter is clogged, a backflush is performed. To accomplish a backflush, first, zero valve 376 is configured to close off the sample gas flow from sample tube 174, and second, backflush valve 382 must be opened. BACKFLUSH+ line 420 and BACKFLUSH− line 422 are the power lines for backflush valve 382. Accordingly, the appropriate voltage is applied across the power lines to open it.

Now, backflush pump 394 must be activated. The backflush pump 394 is activated by the voltage across BACKFLUSH PUMP+line 396 and BACKFLUSH PUMP−line 398. Once backflush pump 394 is properly powered, room air is drawn through filter 402 and enters pump module backflush pathway 392. The room air next passes through pump 394. After passing through the backflush pump, the room air goes through remainder of pump module backflush pathway 392 and connector 390, and enters patient module backflush pathway 388. Once the room air has passed through backflush valve 382, it then enters the backflush tube 172 enroute airway adapter 106. The filtered room air enters airway adapter 106 and clears the filter.

Two-way diagnostic valve 412 together with the zero valve, sample pump and pressure sensor is used to determine if the pneumatic system tubing or components are fluid-tight. When it is desired to check the fluid-tight integrity, two-way diagnostic valve 412 is configured to close off room air from entering the system. Two-way diagnostic valve 412 is powered by the voltage across DIAG+ line 416 and DIAG− line 418. After properly powering the valve, the system is set-up as if zero gas readings were to be made. The sample pump is activated to draw a vacuum in the sample and zero gas pathways of the patient and pump modules. Once a predetermined pressure is reached, the sample pump is deactivated. The pressure readings are monitored to see if there is a pressure change over time which would indicate that there are leaks in the system.

The partial pressures of other gases of interest in the respiratory gas stream are also measured. This is accomplished by external module 430. The pneumatic system of the present invention is such that the respiratory gas stream and the zero gas stream can be routed through external module 430.

External valve 1, 424, and external valve 2, 436, are disposed along pump module sample gas pathway 368 between connector 370 and flow sensor 356. Both valves are two-way valves.

EXT 1+ line 432 and EXT 1− line 434 are the power lines for external valve 1. EXT 2+ line 442 and EXT 2− line 444 are the power lines for the external valve 2. The voltages across these pairs determine whether the sample respiratory gas stream or zero gas stream are directed through pump module sample gas pathway 368 without redirection through external module 430.

When it is desired to route the respiratory gas stream or zero gas stream through external module 430, the proper voltage is placed across EXT 1+ line 432 and EXT 1− line 434, and placed across EXT 2+, line 442 and EXT 2− line 444 to configure external valve 1 and external valve 2 for this purpose. When these valves have this configuration, external value 1 closes off the direction of gas flow through pump module gas pathway 368 toward external valve 2, and opens toward external-in gas pathway 425; and external valve 2 closes off pump module gas pathway 368 in the direction of external valve 1 and opens toward external-out gas pathway 437.

Once external valve 1 and external valve 2 are powered to the above configuration, the respiratory gas stream or zero gas stream passes through external valve 1 and enters external-in gas pathway 425 in the pump module. The gas stream then passes through connector 426 and enters external module-in gas pathway 428. The gas stream upon leaving this gas pathway enters the external module 430's internal gas pathway. Measurements of the partial pressures of other gases of interest are made as the gas stream transits the external module's internal gas pathway.

When the gas stream exits the external module, it enters external module-out gas pathway 440. The gas stream then passes through connector 438 and enters external-out gas pathway 437 in pump module 112. The gas stream then enters external valve 2 where it is routed to pump module sample gas pathway 368.

Flow sensor 356 measures the flow rate of the sample respiratory gas stream or zero gas stream that passes through patient module 109. Flow sensor 556 is a differential pressure transducer. This transducer is commercially available from IC Sensors, Inc., Sunnyvale, Calif. For a 50 cc/min. flow rate, the restriction in pump module gas pathway 368 that precedes flow sensor 356 produces a pressure drop of approximately 0.5 psi. The reference side of the pressure transducer connects to one side of the restriction and the measurement side connects the other. A change in the flow rate causes a change in the pressure drop which is measured by the transducer. Such changes generate representative voltages which are output as the FLOW PRS signal on line 391. The FLOW PRS RTN signal on line 393 is tied to ground.

Within flow sensor 356, prior to output therefrom, the detected voltage is input to a fixed gain differential amplifier circuit. This amplifier circuit includes a potentiometer which is set to correct for span factor. The amplified and span factor corrected voltage representation of flow rate is output on line 391 as the FLOW PRS signal. The FLOW PRS signal and the FLOW PRS RTN signal (ground) are input to the analog processing circuits 124 for further processing as will be described.

Figure 4B:
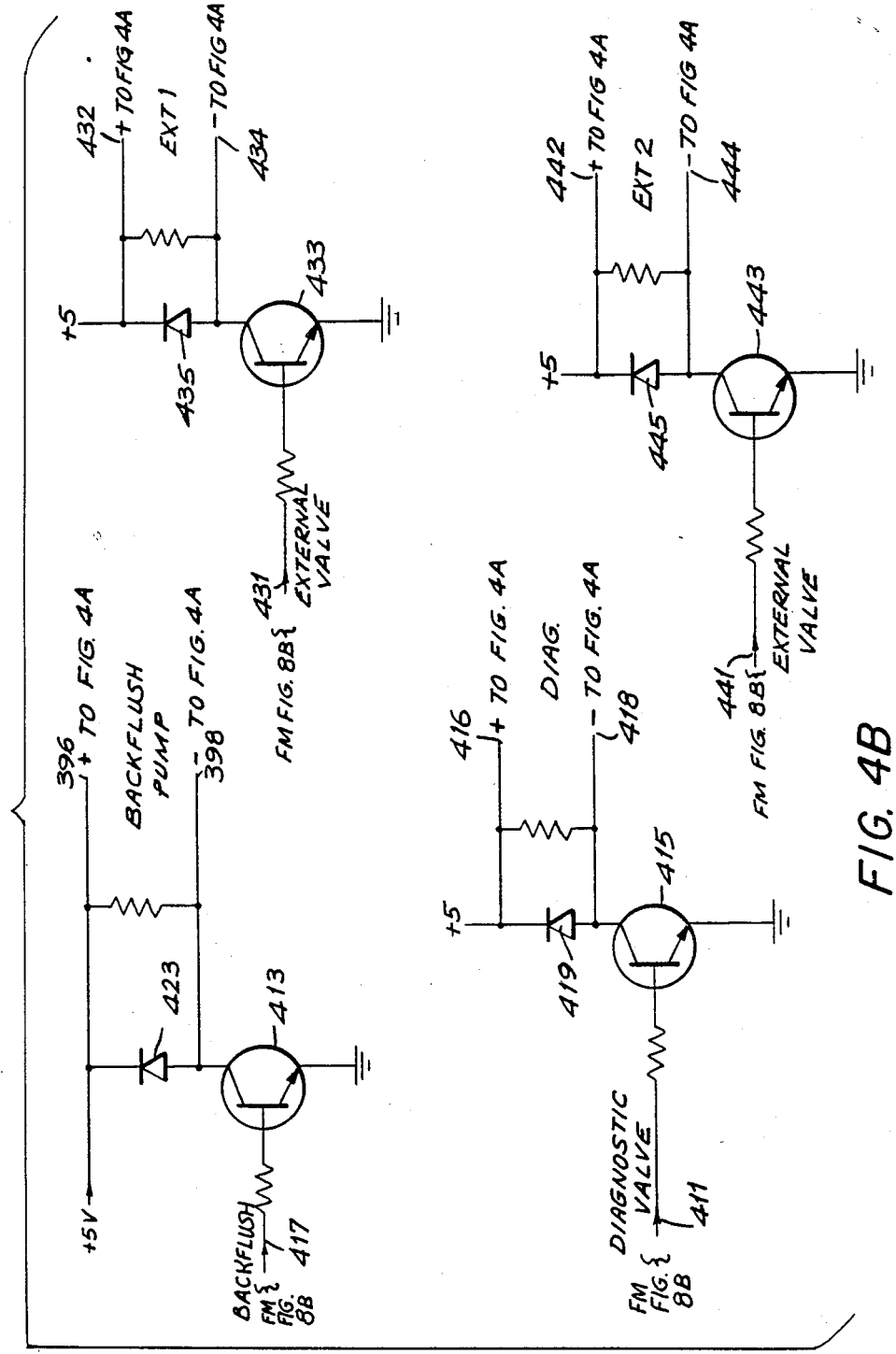
FIG. 4B shows schematic diagrams of drive circuits for various components associated with control of the pneumatics.

FIG. 4B shows the powering circuits for backflush pump 394, diagnostic valve 412, external valve 1, 424, and external valve 2, 436. The circuit for powering sample pump 358 is in the analog processing circuitry and will be discussed subsequently.

The circuits for powering the backflush pump, the diagnostic valve, the external valve 1, and the external valve 2 are subtantially the same. Therefore, the generation of the powering voltages for the backflush pump will be described and the signal names and reference numbers for the other three will follow in parentheses in the following order: the diagnostic valve, the external valve 1, and external valve 2.

The BACKFLUSH (DIAGNOSTIC, EXTERNAL VALVE 1, and EXTERNAL VALVE 2) signal on line 417 (411, 431, 441) is input to the base of transistor 413 (415, 433, 443). The BACKFLUSH (DIAGNOSTIC, EXTERNAL VALVE 1, and EXTERNAL VALVE 2) signal voltage determines whether the BACKFLUSH PUMP− (DIAG−, EXT 1−, and EXT 2−) signal is grounded to establish a voltage difference between the BACKFLUSH PUMP+− (DIAG+, EXT 1+, and EXT 2+) and the BACKFLUSH PUMP−(DIAG−EXT 1−, and EXT 2−) signals. Diode 423 (419, 435, 445) protects the transistor when it is turned off.

Figure 5A:
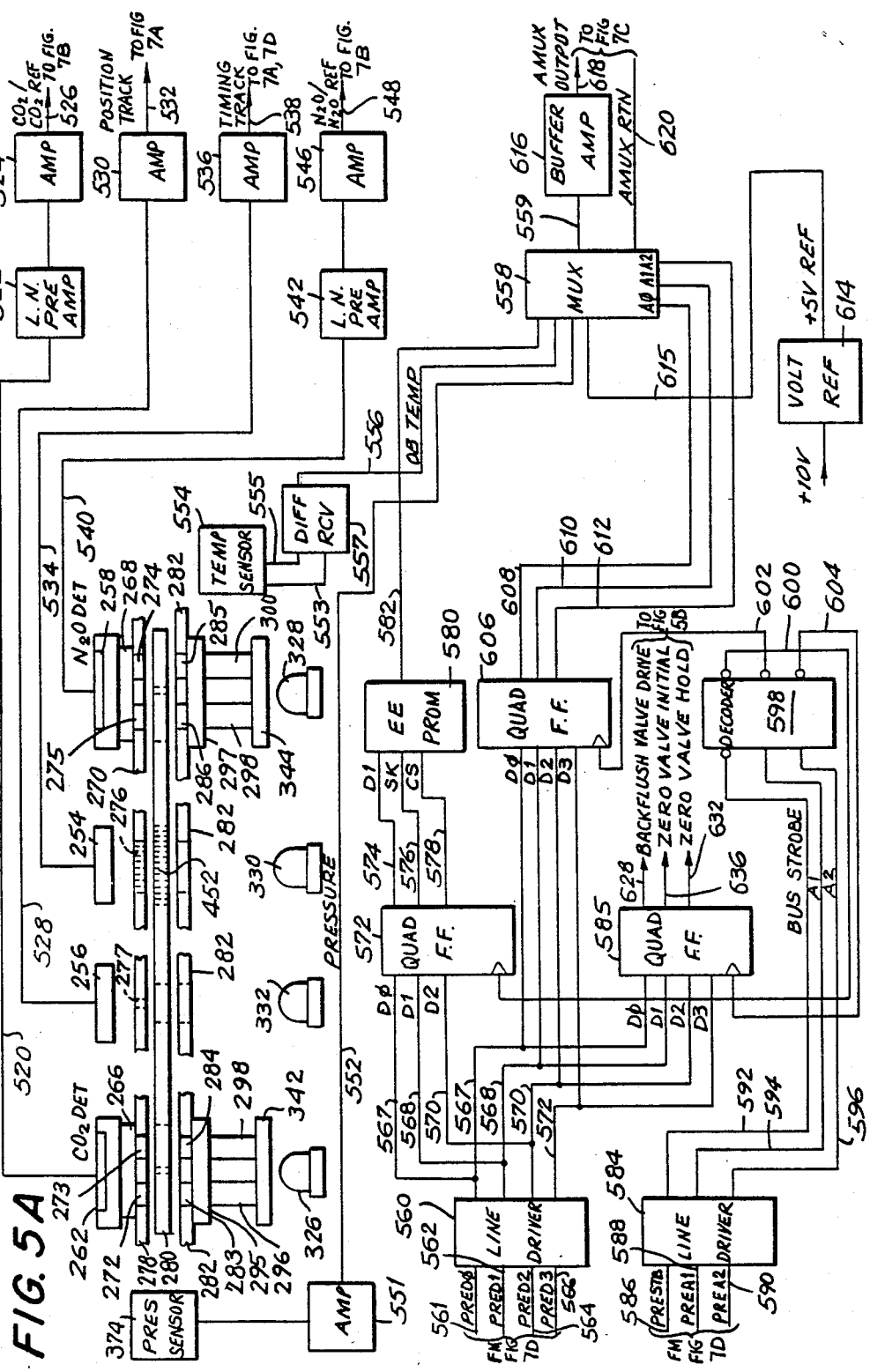
FIG. 5A is a schematic diagram of the optical bench circuitry of the multichannel gas analyzer system of the present invention.

FIG. 5A is a schematic diagram of the circuitry and selected components of optical bench 109. FIG. 5A shows cross-section views of sample gas pathway 298, $CO_2$ reference cell 296, and $N_2O$ reference cell 300. It is understood that the sample gas flow enters gas pathway 298 at the $CO_2$ detection channel assembly and exits at the $N_2O$ detection channel assembly. Accordingly, the gas stream first travels past the $CO_2$ detection channel assembly comprising infrared light source 326, sapphire windows 342 and 295, source aperture 282, detector aperture 270, optical filter 266 and lead selenide detector 262. Next it passes the $N_2O$ detection channel assembly comprising infrared light source 328, sapphire windows 344 and 297, source aperture 282, detector aperature 270, optical filter 268, and lead selenide detector detector 258. Chopper wheel 280, common to both detection channel assemblies, has openings for simultaneous detection of the $CO_2$ and $N_2O$ gas signals, simultaneous detection of the $CO_2$ and $N_2O$ reference optical path signals and simultaneous detection of a dark period for the $CO_2$ and $N_2O$ channels.

Broad band optical energy from each infrared source is passed through the gas stream. The optical filters only pass a narrow infrared band associated with the absorption characteristics of the specific gas of interest when the chopper wheel has its openings aligned with the gas optical path and reference optical path of each detection channel assembly. The energy streams exiting the respective filters issue on the associated detector. A representative three-step waveform output from a detection channel assembly is shown at 466 in FIG. 6C. The dark signal is shown at 468, the reference signal is shown at 470, and the gas signal is shown at 472. The amplitude of the gas and reference signals are indicative of the amount of energy within the filter's band transmitted through the gas stream in the gas pathway and the reference cell.

The output signal from $CO_2$ detector 262 on line 520 is input to low noise preamp 522. The output of low noise preamp 522 is input to amplifier 524. The output of amplifier 524 is the $CO_2/CO_2$ REF signal on line 526 which is input to the analog input circuitry.

The output signal from $N_2O$ detector 258 on line 540 is input to low noise preamp 542. The output of low noise preamp 542 is input to amplifier 546. The output of amplifier 546 is the $N_2O/N_2O$ REF signal on line 548 which is input to the analog input circuitry.

Also generated are the POSITION TRACK and TIMING TRACK signals which are used for determining the occurrence of certain events during a timing cycle and providing the basic timing cycle based on one revolution of chopper wheel 280.

The position track optical path comprises LED 332, source aperture 282, detector aperture 270, and photodiode 256. The timing track optical path comprises LED 330, source aperture 282, detector aperture 270, and photodiode 254. The position track path is chopped by the gas signal openings in chopper wheel 280. The timing track optical path is chopped by the 90 timing track openings in chopper wheel 280.

The chopped infrared energy from LEDs 332 and 330 issue on position track photodiode 256 and timing track photodiode 254, respectively. The output of position track photodiode 256 on line 528 is input to amplifier 530. The output of amplifier 530 is the POSITION TRACK signal on line 532. The output of timing track photodiode 254 on line 534 is input to amplifier 536. The output of amplifier 536 is the TIMING TRACK signal on line 538. A representative POSITION TRACK signal is shown at 460 in FIG. 6C and a representative TIMING TRACK signal is shown at 464 in FIG. 6C. The POSITION TRACK and TIMING TRACK signals are input to the analog input circuitry for the generation of the GAS GATING, REF GATING, and DEMOD SYNC signals for demodulating and processing of the $CO_2/CO_2$ REF and $N_2O/N_2O$ REF signals.

Referring to FIGS. 6A and 6B, a top view of chopper wheel 280 is shown. In FIG. 6A the top of the chopper wheel is shown alone and in FIG. 6B it is shown in relation to certain other components of the optical bench.

From the center of chopper wheel 280 outward, the first chopping means is timing track 452. Timing track 452 is in the optical path comprising of LED 330, source aperture 282, detector aperture 270 and photodiode 254. As stated, the output of the timing track optical path is shown at 464 of FIG. 6C. The series of opening representing the timing track total 90, thereby giving a timing track cycle count of 90.

The next chopping means are on the gas channel openings at 281. There are three gas channel openings, each of which subtends 40° and they are spaced 120° apart. The openings are situated such that there is simultaneous detection of the partial pressures for $CO_2$ and $N_2O$ as shown in FIG. 6B.

Radially outward from the gas channel chopping means, the chopper wheel has three openings at 450 for chopping the $CO_2$ and $N_2O$ reference optical paths. Each reference channel opening subtends 40° and they are spaced 120° apart. The openings are situated such that there is simultaneous detection of the $CO_2$ and $N_2O$ reference optical paths.

In the rotation of the chopper wheel 280, there is a 40° portion that precedes each reference opening and follows each gas channel opening. During this period, referred to as the "dark" period, a signal is detected whereby no infrared light issues on the $CO_2$ or $N_2O$ detector. This is the base line signal from which the gas channel and reference channel signals are measured. This signal is removed from the gas channel and reference channel signals during signal processing resulting in the detected signals which are due only to the partial pressures of $CO_2$ and $N_2O$ in respiratory gas stream and the $CO_2$ and $N_2O$ reference optical paths.

Each timing cycle, or single rotation, of chopper wheel 280 has three detection subcycles comprising dark detection period, reference detection period, and gas detection period. A representative repeating three-stepped waveform pattern is shown at 466 in FIG. 6C.

The position track optical path comprises LED 332, source aperature 282, detector aperture 270 with single slit 277 and photodiode 256. The gas channel openings are used to chop the position track optical path. The resultant signal is the square wave signal shown at 460 in FIG. 6C. The POSITION TRACK signal, as will be described, is used to mark gas channel detection events.

Figure 6C:
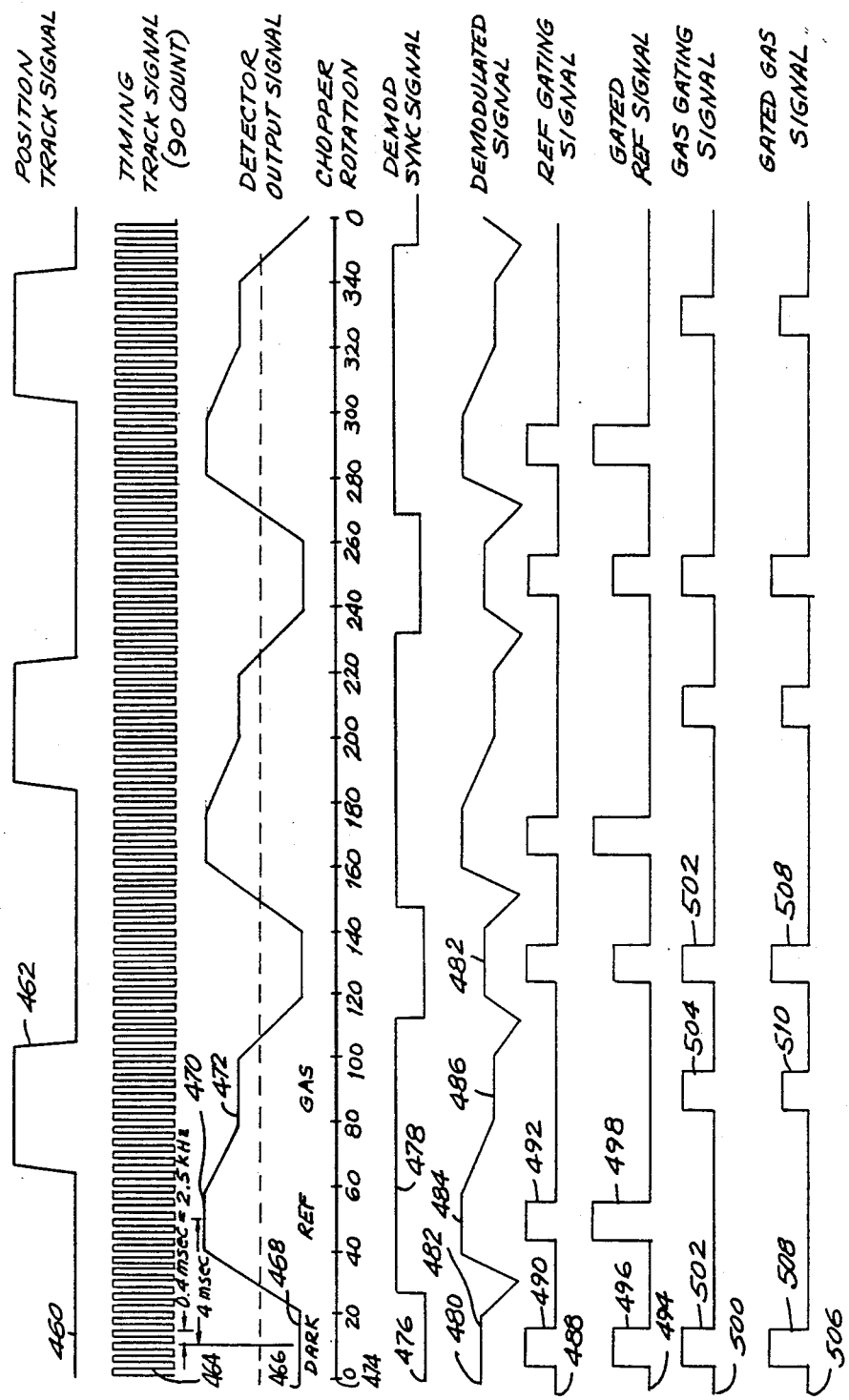
FIG. 6C are waveforms associated with gas and reference optical path detection, and demodulation.

The TIMING TRACK and POSITION TRACK signals in conjunction with PROM 656 (FIG. 7A) are used to generate the GAS GATING, REF GATING and DEMOD SYNC signal waveforms shown in FIG. 6C at 500, 488, and 476, respectively. These signals will be used to obtain useful information with respect to the detected $CO_2$ partial pressure and the $N_2O$ partial pressure, and the reference optical path signal associated with each.

At this point, the only signals discussed which are ready for output from the optical bench are the detected $CO_2/CO_2$ REF signal, $N_2O/N_2O$ REF signal, the TIMING TRACK signal, and the POSITION TRACK signal. The remainder of the signals output from the optical bench circuitry are the signals output from multiplexer 558 and the powering voltages for the backflush valve and the zero valve. The multiplexer and its associated signals will be discussed then the generation of the powering voltages will be discussed.

The first input to multiplexer 558 is the output of EEPROM 580. EEPROM 580 stores coefficients relating to characterization of the optical bench.

The characterization coefficients do not adjust or change the operation of any component of the optical bench or the apparatus as a whole. These coefficients correct the bench's measurements for system component deviation from ideal.

The inputs to EEPROM 580 are the data bus D1 signal on line 574, the SK (serial data clock) signal on line 576 and the CS (chip select) signal on line 578. The CS and SK signals control the EEPROM's output. The D1 signal is the data input to the EEPROM. These three signals are output from quad. flip flop 572. The data inputs to quad. flip flop 572 are optical bench data bus signals DØ-D2 on lines 567, 568, and 570, respectively. The DØ-D2 signals are three of the four outputs of line driver 560 whose inputs are the 4 bit parallel PREDØ-PRED3 signals on lines 561, 562, 564, and 566. These signals are from the analog input circuitry.

Quad. flip flop 572 is clocked by the output of decoder 598 on line 600. The inputs to decoder 598 are the BUS STROBE signal on line 592, the A1 signal on line 594, and the A2 signal on line 596. These signals are output from line driver 584. The inputs to line driver 584 are the PRESTB signal on line 586, the PREA1 signal on line 588, and the PREA2 signal on line 590. These signals are received from the analog input circuitry. Decoder 598 is enabled by the BUS STROBE signal and the output depends on the logic states of the A1 and A2 signals. When properly instructed, the EEPROM outputs the characterization coefficients to multiplexer 558.

The second input to multiplexer 558 is the OB TEMP (optical bench temperature) signal on line 556. The bench temperature is sensed by temperature sensing and control circuit 554. The sensed temperature (in volts) on line 555 is input to differential receiver 557. The second input to differential receiver 557 on line 553 is tied to ground. The output of differential receiver 557 is input to multiplexer 558. Unlike many prior art optical benches which actively control optical bench temperature for accurate readings, the optical bench of the present inventions does not control the optical bench temperature.

The third input to multiplexer 558 is the signal repressententive of the pressure in gas pathway 298 sensed by pressure sensor 374. The sensed signal is amplified by amplifier 551 and the amplified pressure signal on line 552 is input to multiplexer 558.

Pressure sensor 374 is an absolute pressure measuring type pressure sensor. The pressure sensor is commercially available from IC Sensors, Inc., Sunnyvale, Calif.

The pressure is continuously monitored during system operation. Rapid pressure changes may indicate various problems in the optical bench. The pressure within the optical bench must be considered in calculating gas partial pressures for display, as more fully discussed.

The pressure sensor also measures barometric pressure at system start up. This value is stored in memory for later use. The stored value for barometric pressure is updated during every zero gas reading.

The fourth input to multiplexer 558 is the output of voltage reference 614. The input to voltage reference 614 is a +10 v signal. Its output is the +5V REF signal on line 615 which is input to multiplexer 558.

The DØ-D3 signals of the optical bench data bus output from line driver 560 are input to quad. flip flop 606. This flip flop is clocked by the output of decoder 598 on line 602. When clocked, quad. flip flop 606 provides a parallel 3-bit signal on lines 608, 610, and 612 which is input to the control inputs to multiplexer 558. Based on the logic states of this 3-bit signal, a multiplexed signal is output from multiplexer 558 on line 559. The multiplexed signal on line 559 is processed by buffer amplifier 616 and output therefrom as the AMUX OUTPUT signal on 618. The AMUX OUTPUT signal is then sent to the analog input circuitry for further processing. Also output from multiplexer 558 and sent to the analog input circuitry is the AMUX RTN signal on line 620. This signal is tied to ground.

The DØ-D3 signals on line 566, 568, 570, and 572 are input to quad. flip flip 585. This flip flop is clocked by the output of decoder 598 on line 604. The outputs of quad. flip flop 585 are the BACKFLUSH VALVE DRIVE signal on line 628, the ZERO VALVE INITIAL signal on line 636, and the ZERO VALVE HOLD signal on line 632. These signals control powering the backflush and zero valves.

FIGS. 5B shows the circuits for powering backflush valve 382 and zero valve 376 shown in FIG. 4A. The BACKFLUSH VALVE DRIVE signal is input to the base of transistor 624. The BACKFLUSH VALVE DRIVE signal voltage determines whether the BACKFLUSH− signal on line 422 is grounded to establish a voltage difference between the BACKFLUSH+ signal on line 420 and the BACKFLUSH− signal on line 422. Diode 626 protects transistor 624 when it is turned off.

The circuit for powering zero valve 376 is for powering the zero valve initially, which requires a greater voltage, and for holding the valve in the changed position after initially powering it, which requires less voltage. The ZERO VALVE INITIAL signal on line 636 is input to the base of transistor 634. The ZERO VALVE INITIAL signal voltage determines whether the ZERO− signal on line 380 is grounded to establish a voltage difference between the ZERO+ signal on line 378 and the ZERO−signal on line 380. Diode 638 protects the transistor when it is turned off.

After initially powering zero voltage 376, the zero voltage is held in position by the following: The ZERO VALVE HOLD signal on line 632 is input to the base of transistor 630. The ZERO VALVE HOLD signal voltage determines whether or not the ZERO−signal on line 380 is grounded to establish a voltage difference between the ZERO+signal on line 378 and the ZERO−signal on line 380. There is a voltage drop across resistor 631 thereby reducing the voltage difference between the ZERO+line and the ZERO−line from what it would be normally without the resistor. Similarly, diode 638 protects the transistor when it is turned off.

FIGS. 7A-7D are schematic diagrams of analog input circuitry 122 (FIG. 1). The inputs to this circuitry are primarily the analog outputs from optical bench 111 and signals from analog processing circuitry 124.

Referring to FIG. 7A, the temperature of the analog circuitry is determined by REF-02, 690. The output of REF-02 is amplified by amplifier 694 and output therefrom as the $V_T$ (Box temperature) signal on line 696. Also output from REF-02 is the $V_{OFF}$ signal on line 692. This signal is used for insuring that the outputs associated with the gated gas and reference signals are at least zero. REF-02 is commercially available from Precision Monolithics, Inc., Santa Clara, Calif.

The generation of the gating signals and demodulation signals for use in obtaining useful information from the detected gas and reference signals, will be discussed. The TIMING TRACK signal on line 538 is the first input to differential receiver 640. The second input is the GAS RTN signal on line 668. This signal is tied to ground. The output of differential receiver 640 is input to pulse shaping circuit 642 which processes the incoming signal so that clean square waves are produced at its output. The output of pulse shaping circuit 640 on line 644 is input to the clock inputs of 4-bit counters 646 and 660, flip flops 672 and 676, and input to the clock input to octal flip flop 658.

The POSITION TRACK signal on line 532 is input to differential receiver 666. The second input is the GAS RTN signal on line 668. The output of differential receiver 666 is input to pulse shaping circuit 669, which like pulse shaping circuit 642, processes the incoming signal so that clean square waves are produced at its output. The output of pulse shaping circuit 669 is input to the data input of flip flop 672.

The negative-true Q bar output of flip flop 672 on line 674 is input to the data input of flip flop 676 and is also input as the first input to NAND gate 678. The negative-true Q bar output of flip flop 676 is the second input to NAND gate 678. The output of NAND gate 678 on line 680 is input to the "clear" inputs of counters 646 and 660. (The "bar" designation after a signal or input name indicates the inverted state of the signal or input without the bar designation, as is known by those skilled in the art).

Flip flops 672 and 676 are clocked by the processed TIMING TRACK signal. Accordingly, this serves to synchronize the POSITION TRACK signal with the TIMING TRACK signal.

The two flip flops and NAND gate cause clearing of the counters during the period from one TIMING TRACK signal after the beginning of the position track pulse to one TIMING TRACK signal after the end of a position track pulse. Therefore, the counters will count from the end of the position track pulse to the beginning of the next. Since the carry-over output of counter 646 is input to the enable inputs to counter 660, there is a continuous count until the counters are cleared.

Outputs of counter 646 on lines 648, 650, 652 and 654, and the outputs of counter 660 on lines 662 and 664, are input to PROM 656. PROM 656 is programmed for the waveform patterns for the GAS GATING, REF GATING, and DEMOD SYNC signals. Therefore, based on the logic values of the signals output from the counters, PROM 656 provides outputs to octal flip flop 658 that will produce the programmed waveform patterns for these signals. Accordingly, when octal flip flop 658 is clocked by the processed TIMING TRACK signal, its outputs are the GAS GATING signal on line 684, whose representative waveform is shown at 500 in FIG. 6C; the REF GATING signal on line 686, whose representative waveform is shown at 488 in FIG. 6C; and the DEMOD SYNC signal on line 688, whose representative waveform is shown at 476 in FIG. 6C.

The FLOW PRS signal on line 391 is input to the differential receiver 702. The second input to the differential receiver is the FLOW PRS RTN signal on line 393. These signals are from flow sensor 356 in pump module 112. The output of differential receiver 702 is the FLOW PRS SIG signal on line 704.

The circuit in FIG. 7A comprising high pass filters 708, peak detector 710, comparator 715, level buffer 716, and flip flop 718 is for detecting if the patient module has impacted something with such severity that the apparatus may need to perform a zero gas reading to continue to make accurate measurements.

The BUFFERED $CO_2$ signal on line 706 is input to high pass filters 708. The output of the high pass filters is input to peak detector 710. The peak detector provides outputs on lines 712 and 714 which are input to comparator 715. The output of comparator 715 is processed by the level buffer 716 and input to the clock input of flip flop 718. The Q output of flip flop 718 is the IMPACT signal on line 722.

When the system is turned on, the IMPACT RESET bar signal on line 720 has a logic "0" value to reset the flip flop 718. Accordingly, the Q output of the flip flop, which is the IMPACT signal, has a logic "0" value. The signal input to the data input of flip flop 718 is the +5v signal which, therefore, places a logic "1" value at the data input.

In operation, the BUFFERED $CO_2$ signal is first passed through the high pass filters. In the peak detector, the signal is divided down and the outputs of the peak detector that are input to the comparator are the basic signal and the divided down signal. The output of the comparator is a relatively steady state signal which is input to the clock input to the flip flop after level buffering.

When the apparatus suffers an impact of sufficient severity, there is a rapid change in the high frequency component. This will cause the comparator to provide an output which will clock flip flop 718. When the flip flop is clocked, the logic "1" value at its data input is output from the Q output as the IMPACT signal indicting that the apparatus has impacted something with sufficient severity that the apparatus may need to do a zero gas reading. When the IMPACT signal has a logic "1" value, it ultimately will cause an alarm to indicate this condition.

Figure 7B:
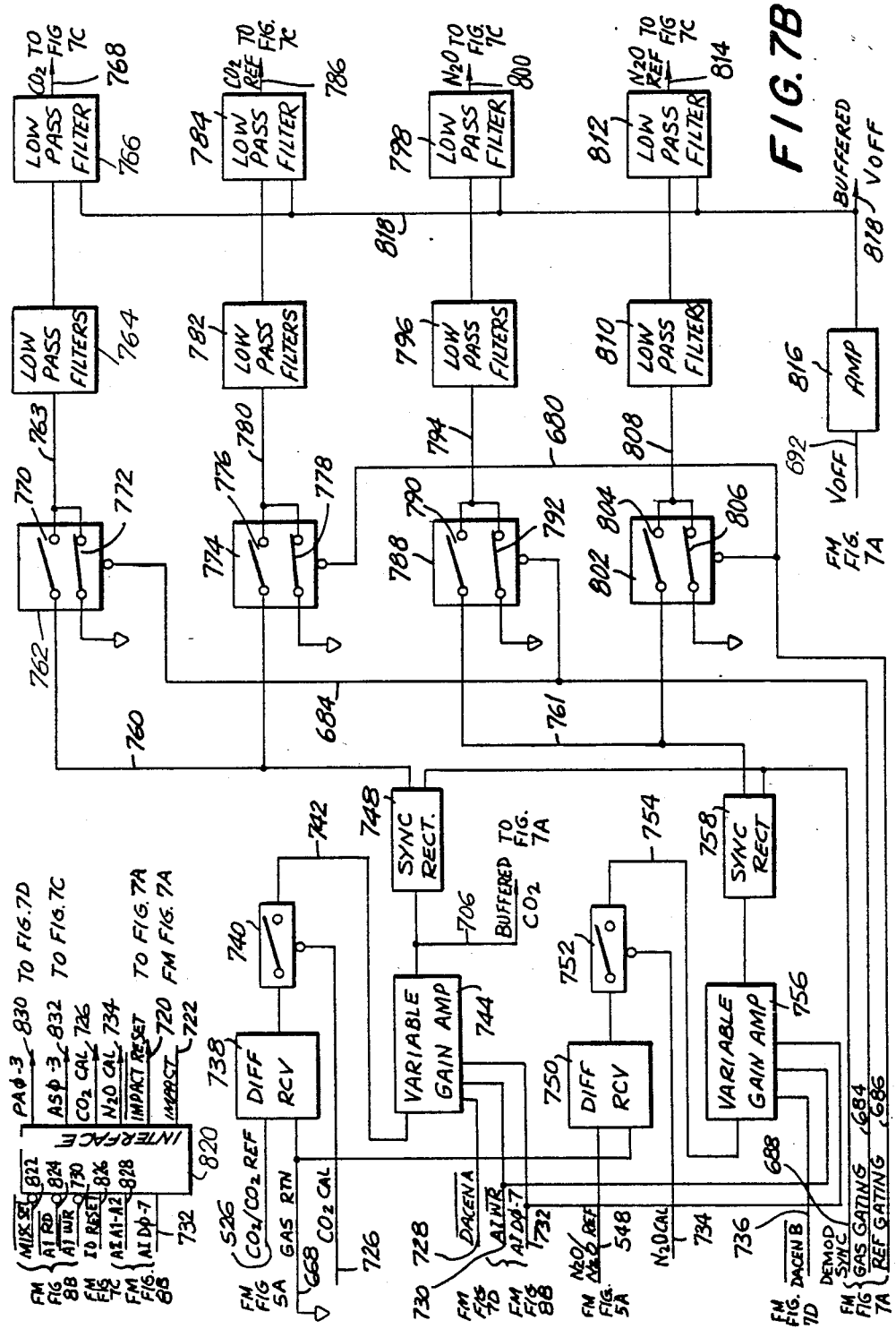
Figure 7C:
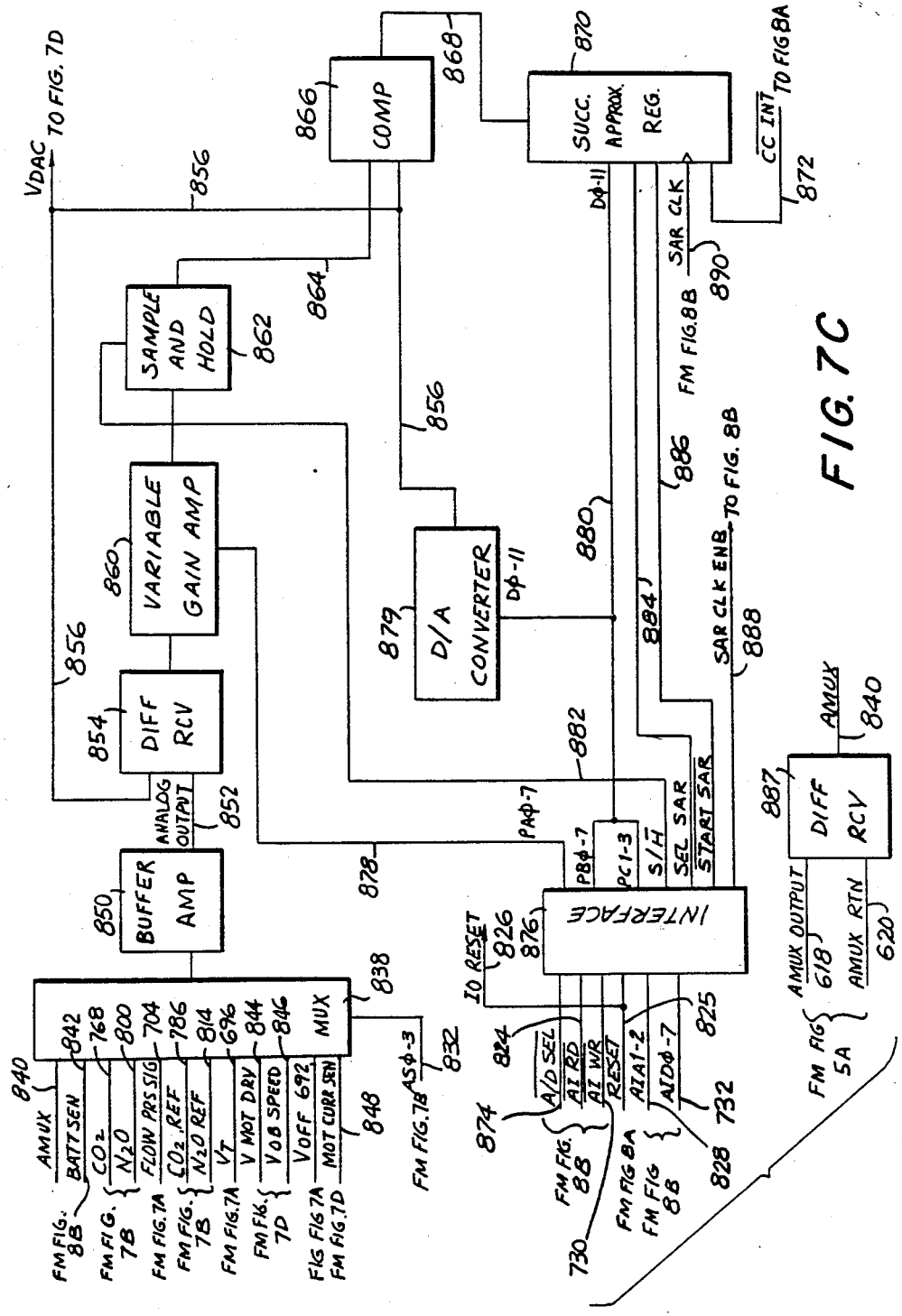

In the circuit in FIG. 7B, the $CO_2/CO_2$ REF signal on line 526 and the $N_2O/N_2O$ REF signal on line 548 are similarly demodulated, have the dark period signals removed therefrom each, and have each signal separated into the gas signal and the reference signal before input to multiplexer 838 (FIG. 7C). Accordingly, the $CO_2/CO_2$ REF channel path will be described and the signal names and reference numbers for the $N_2O/N_2O$ REF channel path will follow in parentheses.

The $CO_2/CO_2$ REF ($N_2O/N_2O$ REF) signal on line 526 (548) is input to differential receiver 738 (750). The second input to differential receiver 738 (750) is the GAS RTN signal on line 668. The GAS RTN signal is tied to ground. The output of differential receiver 738 (750) is input to electronic switch 740 (752). The control input to electronic switch 740 (752) is the $CO_2$ CAL ($N_2O$ CAL) signal on line 726 (734). The $CO_2$ CAL ($N_2O$ CAL) signal will have the proper logic state to open the switch when it is desired to determine the system's offset voltage, as will be described subsequently; otherwise the switch is closed.

The output of electronic switch 740 (752) is input to variable gain amplifier 744 (756). The control inputs to variable gain amplifier 744 (756) are the DACEN A bar (DACEN B bar) signal on line 728 (736), the AIWR bar signal on line 730, and the parallel 8-bit data bus signals AID∅-7 on line 732. The DACEN A bar (DACEN B bar) signal is input to the CE bar input, the AIWR bar signal is input to the WR bar input, and the AID∅-7 is input to the parallel 8-bit input of the amplifier. Accordingly, when the AID∅-7 signals are written into the amplifier, it will have a gain from 0 to 64 based on these values.

The output of variable gain amplifier 744 (756) is input to synchronous rectifier 748 (758). Line 706 connects to the output of variable gain amplifier 744. Line 706 contains the BUFFERED $CO_2$ signal that is input to the impact circuit in FIG. 7A.

Synchronous rectifier 748 (758) demodulates the $CO_2/CO_2$ REF ($N_2O$ REF) signal by removing the dark period signal from the gas and reference signals. The demodulating signal input to synchronous rectifier 748 (758) is the DEMOD SYNC signal on line 688. The DEMOD SYNC signal waveform is shown at 476 of FIG. 6C. As can be seen in FIG. 6C, the DEMOD SYNC signal has a $+1$ value during the reference and gas periods, and a $-1$ value during the dark period. Accordingly, the dark period signal is inverted while reference and gas period signals values are not. This results in the demodulated signal shown at 480 in FIG. 6C, where the inverted dark period signal is shown at 482, and the non-inverted reference and gas signals are shown at 484 and 486, respectively.

The demodulated $CO_2/CO_2$ REF ($N_2O/N_2O$ REF) signal output from synchronous rectifier 748 (758) on line 760 (761) is input to double switches 762 and 774 (788 and 802). As is shown for each, the switches are oppositely disposed: in double switch 762 (788), switch 770 (790) is open and switch 772 (792) is closed; and in double switch 774 (802), switch 776 (804) is open and switch 778 (806) is closed. When the value input to the control inputs of double switches 762 and 774 (780 and 802) changes, then switches pairs will be change their respective pen or closed conditions.

The control input to double switch 762 (788) is the GAS GATING signal on line 684 and the control input to double switch 774 (802) is the REF GATING signal on line 686. The GAS GATING signal controls the disposition of switches 770 (790) and 772 (792) according to the waveform shown at 500 in FIG. 6C, and the REF GATING signal controls the disposition of switches 776 (804) and 778 (806) according to the waveform shown at 488 in FIG. 6C.

The signal output from double switch 762 (788) is input to low pass filters 764 (796). The signal is output from the low pass filters and input to low pass filter 766 (798). The second input to low pass filter 766 (798) is the BUFFERED $V_{OFF}$ signal on line 818. The BUFFERED $V_{OFF}$ signal is input to low pass filters 766 (798) to insure that output is never less than zero.

The signal output from double switch 774 (802) is input to low pass filters 782 (810). The signal is output from the low pass filters and input to low pass filter 784 (812). The second input to low pass filter 784 (812) is the BUFFERED $V_{OFF}$ signal on line 818. This signal insures that the output of low pass filter 784 (812) is never less than zero.

After gating, the $CO_2$($N_2O$) signal has a waveform substantially as shown at 506 of FIG. 6C, with the pulse at 508 being attributed to the dark period and the pulse at 510 being attributed to the partial pressure of $CO_2$ in the gas pathway. Similarly, after gating the $CO_2$ REF ($N_2O$ REF) signal has a waveform substantially as shown at 494 in FIG. 6C, with the pulse at 496 being attributed to the dark period and the pulse at 498 being attributed to the reference optical path. After filtering, the waveform outputs for $CO_2$ on line 768 and $N_2O$ on line 800 are changing waveforms corresponding to the detected value for each gas. The $CO_2$ reference signal on line 786 and $N_2O$ reference signal on line 814 are the current values for each reference optical path.

The inputs and outputs to interface 820 will now be discussed. The inputs to interface 820 are the MISC SEL bar signal on line 822, the AIRD bar signal on line 824, the AIWR bar signal on line 730, the IORESET signal on line 826, the analog input circuitry address bus signals AIA1-2 on line 828, and the analog input circuitry data bus signals AID∅-7 on line 732.

The MISC SEL bar signal is input to the chip select input of interface 820. The AIRD bar and AIWR bar signals are input to the RD and WR inputs respectively to interface 820. The IORESET signal is input to the reset input to interface 820. The AIA1-2 signal and the AID∅-7 signal are input respectively to address bus inputs and the data bus inputs.

The outputs of interface 820 are the 4-bit parallel PA∅-3 signal on line 830, the parallel 4-bit parallel AS∅-3 signal on line 832, the $CO_2$ CAL signal on line 726, the $N_2O$ CAL signal on line 734 and the IMPACT RESET bar signal on line 720, and the IMPACT signal is input on line 722.

Figure 7D:
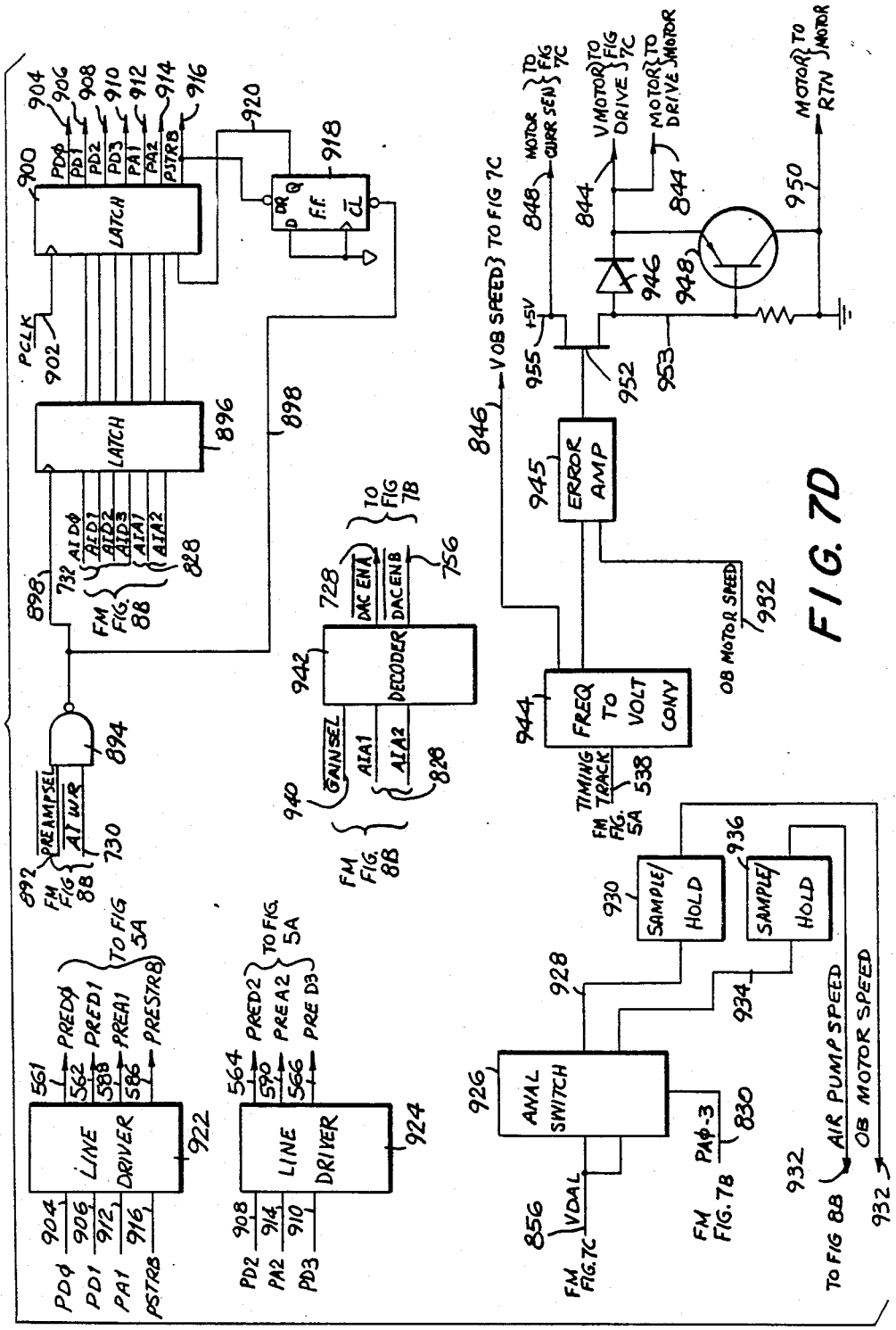

The PA∅-3 signal on line 830 is input to the control inputs to analog switch 926 (FIG. 7D). The AS∅-3 signal on line 832 is input to the control inputs to multiplexer 838 (FIG. 7C). The $CO_2$ CAL and $N_2O$ CAL signals are input to electronic switches 740 and 752, respectively, for use in determining the offset voltages for the $CO_2$ and $N_2O$ gas channels and the $CO_2$ REF and $N_2O$ REF channels (FIG. 7B). The IMPACT RESET bar and IMPACT signals are for use in the impact detection circuit (FIG. 7A).

Referring to FIG. 7C, placement of the certain analog signals on the analog input circuitry data bus will be described.

The inputs to multiplexier 838 are the AMUX signal on line 840, the BATT SEN signal on line 842 (from power supply circuitry 158, FIG. 1), the $CO_2$ signal on line 768, the $N_2O$ signal on line 800, the FLOW PRS SIG signal on line 704, the $CO_2$ REF signal on line 786, the $N_2O$ REF signal on line 814, the $V_T$ signal on line 696, the V MOT DRV signal on line 844, the $V_{OB\text{-}SPEED}$ signal on line 846, the $V_{OFF}$ signal on line 692, and the MOT CURR SEN signal on line 848. (Certain of these signals have been described while others have not; those that have not will be described subsequently).

The AMUX OUTPUT signal on line 618 and the AMUX RTN signal on line 620, both of which are output from multiplexer 558 (FIG. 5A), are input to differential receiver 887. The output of differential receiver 887 on line 840 is the AMUX signal which is input to multiplexier 838.

The parallel 4-bit signal AS∅-3 on line 832 from interface 820 is input to the control inputs of multiplexer 838. Based on the logic states these control signals, multiplexer 838 provides an output to buffer amplifier 850. The multiplexed analog output signal includes the analog values for the detected partial pressures of $CO_2$, $CO_2$ REF, $N_2O$, and $N_2O$ REF; the flow rate of the gas through the optical bench; the pressure and temperature in the optical bench; the temperature of the apparatus containing the analog input circuitry; the speed of the chopper motor; the chopper motor drive voltage; the voltage for maintaining a positive amplifier output values for selected amplifiers; the sensed battery voltage; the sensed motor current; the +5 v reference; and the characterization information.

The signals input to interface 876 are the A/D SEL bar signal on line 874, the AIRD bar signal on line 824, the AIWR bar signal on line 730, the RESET signal on line 825, the parallel 2-bit address signal AIA1-2 on line 828, and the parallel 8-bit signal AID∅-7 on line 732. The outputs of interface 876 will be discussed subsequently in discussing the circuit. Line 826 is connected to line 825 containing the RESET signal. Line 826 is redesignated the IORESET signal for use in the analog input circuitry.

The ANALOG OUTPUT signal on line 852 is input to differential receiver 854. The second input to differential receiver 854 is the system offset signal VDAC on line 856 which is an output of digital to analog (D/A) converter 879.

The offset signal for each of the four gas or reference channels is generated by opening switches 740 or 752 at the appropriate time (FIG. 7B). The voltage output by D/A coverter 879 when these switches are open is that gas or reference channel's voltage offset. This channel offset is subtracted from the measured value for each gas.

The voltage difference output from differential receiver 854 is input to variable gain amplifier 860. The gain of the amplifier is controlled by the parallel 8-bit signal PA∅-PA7 output from interface 876. These signals are from analog input circuitry data bus 732.

The output of variable gain amplifier 860 is input to sample and hold circuit 862. The sample and hold circuit control signal is the S/H (H bar) signal output from interface 876 on line 882. The control signal will hold the sample and hold output signal long enough for conversion of the current data in successive approximation register 870; placement of that data on data bus 880; and input of the present sample and hold signal into the successive approximation register for conversion.

The output of the sample and hold circuit is input to comparator 866. The second input to comparator 866 is the VDAC signal on line 856. The output of comparator 866 is input to successive approximation register 870. The START SAR bar signal on line 886 is input to successive approximation register 870 to start the analog to digital conversion process. The SELSAR signal 884 is input to the output enable input of successive approximation register 870. The logic value of this signal controls placement of the converted data on data bus 880.

Another output of successive approximation register 870 is the CC INT bar signal on line 872 which will be discussed in connection with FIG. 8A.

The SARCLK ENB signal output from interface 876 on line 888 is for generating the SARCLK signal on line 890 as will be discussed in connection with FIG. 8B. This is the first input to NAND gate 1110 for this purpose. The other input to that gate is the CLK 400 signal output from microprocessor 960 on line 970. The states of these signals control the output of NAND gate 1110. The output of NAND gate 1110 after inversion, the SARCLK signal, is used to turn the internal successive approximation register clock on and off.

FIG. 7D shows the remaining circuits of the analog input circuitry.

The PREAMP SEL bar signal on line 892 is input to NAND gate 894. The other input to this gate is the AIWR bar signal on line 730. The output of NAND gate 894 on line 898 clocks 8-bit latch 896. The inputs to 8-bit latch 896 are the AID∅-3 signals from the analog input circuitry data bus on line 732 and AIA1-2 signals from the analog input circuitry address bus on line 828. The output of 8-bit latch 896 is input to 8-bit latch 900.

The signal that clocks latch 900 is the PCLK signal on line 902. The generation of the PCLK signal will be described when discussing FIG. 8C. Also input to 8-bit latch 900 is the Q output of flip flop 918. Flip flop 918 is preset by the PSTRB on signal on line 916 and cleared by the output of NAND gate 894 on line 898.

The outputs of 8-bit latch 900 are the PD∅ signal on line 904, the PD1 signal on line 906, the PD2 signal on line 908, the PD3 signal on line 910, the PA1 signal on line 912, the PA2 signal on line 914, and the PSTRB signal on line 916.

The parallel 4-bit input to line driver from 8-bit latch 900 comprises the PD∅ signal, the PD1 signal, the PA1 signal, and the PSTRB signal. The parallel 4-bit output of this driver is the PRED∅ signal on line 561, the PRED1 signal on line 562, the PREA1 signal on line 588, and the PRESTRB signal on line 586.

The parallel 3-bit input to line driver 924 comprises the PD2 signal, the PA2 signal, and the PD3 signal. The parallel 3-bit output of this driver is the PRED2 signal on line 564, the PREA2 signal on line 590 and the PRED3 signal on 566.

PD∅-PD3/PRED∅-PRED3 are the data lines to the optical bench 4-bit data bus. PA1 and PA2/PREA1 and PREA2 are lines to the parallel 2-bit optical bench address bus. PSTRB/PRESTRB is the data line to the optical bench address bus and data bus strobe.

The VDAC signal on line 856 from D/A converter 879 is representative of the 12-bit converted data bus information. The VDAC signal is input to analog switch 926. The output signal from analog switch 926 on line 928 is processed by sample and hold circuit 930. The output of this circuit on line 932 is the OB MOTOR SPEED signal.

The output signal of analog switch 926 on line 934 is processed by sample and hold circuit 936. The output of this circuit is the AIR PUMP SPEED signal on line 938. The parallel 4-bit signal PA∅-3 on line 830 output from interface 820 is input to the control inputs of analog switch 926.

The TIMING TRACK signal on line 538 output from the detector circuitry is input to frequency to voltage converter 944. The frequency to voltage converter output voltage, $V_{OBSPEED}$, is input to the analog processing circuitry and to error amplifier 945. The $V_{OBSPEED}$ signal is a voltage signal proportional to the chopper motor speed.

The second input to error amplifier 945 is the OB MOTOR SPEED signal on line 932 from analog switch 926. This signal is the voltage set point for the chopper motor speed. The difference in the signals is input to the base of transistor 952. The base of transistor 948 is tied to leg 953 of transistor 952. When transistor 952 is in the "on" condition, this, under the proper conditions, will cause a voltage difference between the MOTOR DRIVE line 844 and the MOTOR RTN line 950, thereby providing the proper power to drive the chopper motor. When transistor 952 turns off, voltage is returned on line 844 which turns on transistor 948. This causes a braking action to help slow down the motor.

The MOT CURR SEN signal on line 848 is tied to leg 955 on the source side of transistor 952. The V MOT DRV signal is also designated 844 since it contains the same signal as the MOTOR DRIVE signal. Diode 946 blocks returned current on line 844 allowing transistor 948 to be turned on for braking.

The inputs to decoder 942 are the GAIN SEL bar signal on line 940 and the parallel 2-bit signal AIA1-2 from address bus 828. The GAIN SEL bar signal is input to the output enable input and the 2-bit address signal is input to the two control inputs of decoder 942. The logic values of the 2-bit address bus signal determine selection of the output. The outputs of decoder 942 are the DACEN A bar signal on line 728 and the DACEN B bar signal on line 736. These signals are the output enable signals for the variable gain amplifiers associated with processing the $CO_2/CO_2$ REF signal and $N_2O/N_2O$ REF signal in FIG. 7B.

Figure 8B:
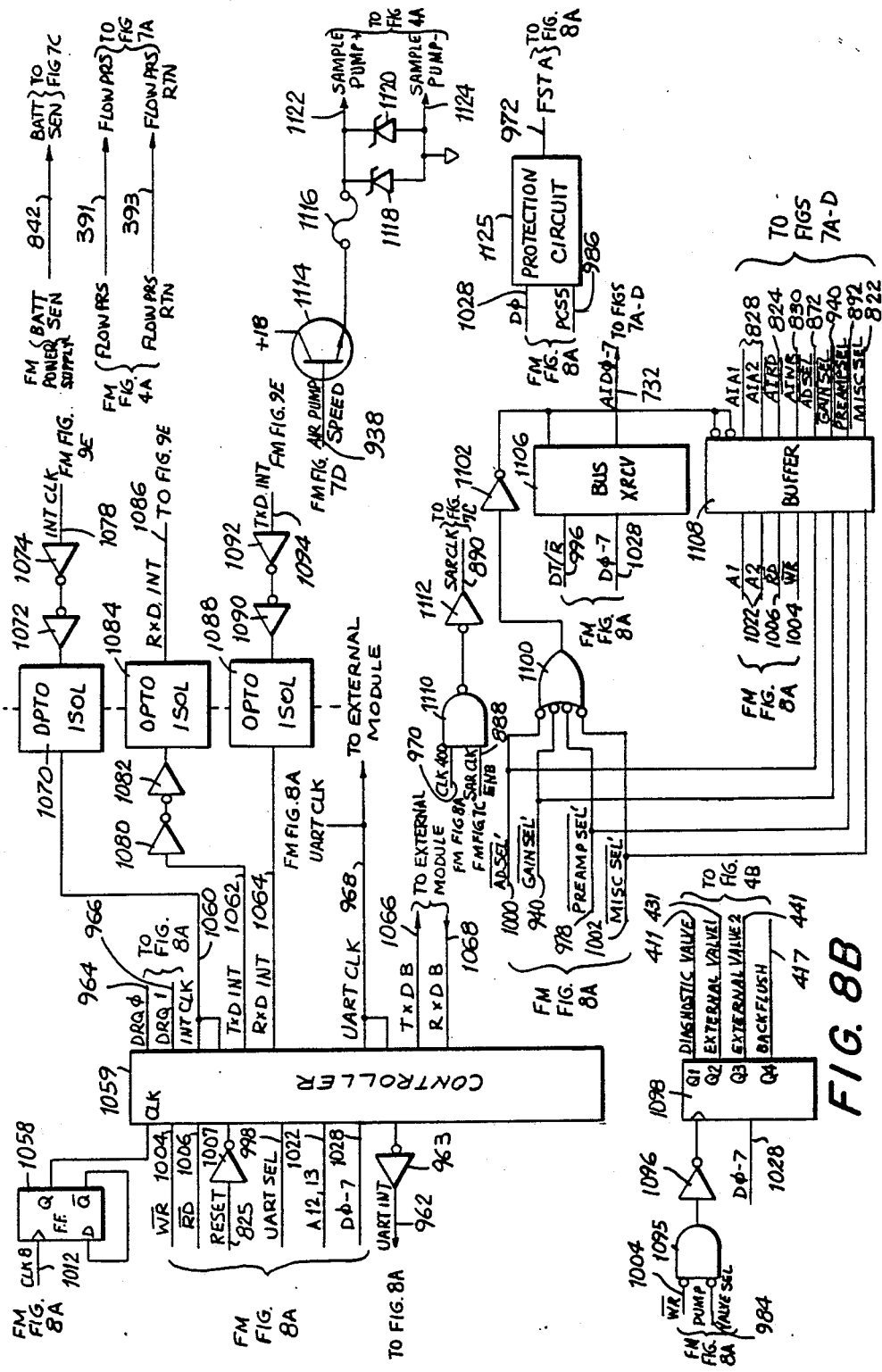

FIGS. 8A, 8B and 8C show analog processing circuitry 124 (FIG. 1). First the circuits of the analog processing circuitry will be described, then their calculating functions will be described.

Referring to FIG. 8A, one component of analog processing circuitry 124 is microprocessor 960. Microprocessor 960 is a model 80186 CPU, commercially available from Intel Corp., Santa Clara, Calif.

The signals input to microprocessor 960 are from the circuitry in FIGS. 8B and 8C, and the analog input circuitry. These are the UART INT signal on line 962, the CC INT bar signal on line 872, the DRQØ signal on line 964, the DRQ1 signal on line 966 and the FST A signal on line 972.

The UART INT signal is an interrupt signal from controller 1059 to indicate the transmission or receipt of data. The CC INT signal is an interrupt signal from successive approximation register 870 to indicate completion of the conversion of an analog signal input and that the converted signals can be put on data bus 880 (FIG. 7C). The DRQØ and DRQ1 signals are direct memory access request inputs indicating that a character is ready to be transmitted from memory or that a character has been received and must be transferred to memory. The FST A signal is the fail safe timer signal to indicate whether or not that the microprocessor has drifted off into an improper loop and is no longer performing its required functions.

The output signals of microprocessor 960 are the PATT SEL signal on line 974, the UCS bar signal on line 976, the PREAMP SEL' bar signal on line 978 the GAIN SEL' bar signal on line 980, the PATIENT SIDE OFF signal on line 982, the PUMP/VALVE SEL signal on line 984, the PCS5 signal on line 986, the ALE signal on line 988, the RESET signal on line 825, the UART CLK signal on line 968, the CLK 400 signal on line 970, the DT/R (R bar) signal on line 996, the DEN bar signal on line 997, the UART SEL signal on line 998, the A/D SEL' bar signal on line 1000, the MISC SEL' bar signal on line 1002, the CLK8 signal on line 1012, the WR bar signal on 1004, the RD bar signal on line 1006, the LCS bar signal on line 1008, and the BHE bar signal on line 1010.

The PATT SEL signal is for generating the PCLK signal on line 902. The PCLK signal clocks latch 900 (FIG. 7D) which contains values to be the placed on the optical bench data bus.

The UCS bar signal on line 976 enables decoder 1040.

The PREAMP SEL' bar signal, the GAIN SEL' bar signal, the A/D SEL' bar signal, the MISC SEL' signal, WR bar signal, and the RD bar signal are used for generating the PREAMP SEL signal on line 892, the GAIN SEL signal on line 940, the A/D SEL bar signal on line 872, the MISC SEL bar signal on line 822, the AIWR bar signal on line 830 and the AIRD bar signal on line 824, respectively, for use by the analog input circuitry shown in FIGS. 7A-7D.

The PREAMP SEL bar signal, the GAIN SEL bar signal, the A/D SEL bar signal, and the MISC SEL bar signal are chip selection inputs for components of the analog input circuitry. The AIWR bar and AIRD bar signals that act as conventional write and read signals.

The CLK 400 signal is used in generating the SAR CLK signal on line 890 and the PCLK signal on line 902 (FIG. 8C).

The DT/R (R bar) signal controls the direction of data flow through bus transceivers 1024, 1025, and 1106.

The DEN bar signal is the output enable signal for bus transceiver 1024 and 1025.

The PUMP/VALVE SEL signal is one of the signals controlling the selection among powering the diagnostic value, the backflush valve, the external valve 1, and/or the external valve 2.

The PCS5 signal is one of the signals used to generate the FST A signal on line 972 for determining if the microprocessor has entered an improper loop.

The LCS bar signal enables decoders 1032 and 1036.

The BHE bar signal is one of the control inputs to decoder 1036.

The UART SEL signal is input to the chip select input of controller 1059.

The ALE signal is for clocking address latches 1014, 1016, and 1018.

The CLK8 signal is the 8 MHZ clock signal for clocking various circuit components of the processor circuitry.

The WR bar signal is the write timing signal indicating that the processor is writing data into memory or into an input/output device.

The RD bar signal is a read timing signal indicating that the processor is reading data.

Memory in FIG. 8A consists of four read only memories (ROMs) 1046, 1048, 1054, and 1056; and two random access memories (RAMs) 1050 and 1052. This memory is conventionally connected to address bus 1022 and data bus 1028.

FIG. 8A shows three address latches, 1014, 1016, and 1018. These latches are clocked by the ALE (address latch enable) signal input to their respective clock inputs. Hence, when the ALE signal has the proper logic state, the three latches are clocked simultaneously.

Latch 1014 receives a parallel 4-bit input from address outputs A16/S3–A19/S6 on line 990. The clocking of latch 1014 will place these values on address bus 1022.

The parallel 8-bit information signal AD8–15, output from microprocessor 960 on line 992, is input to latch 1016. The AD8–15 signal can contain either address or data information. When it is handling address information and those values are input to latch 1016, when that latch is clocked, the latched address values are placed on address bus 1022.

Similarly, the parallel 8-bit signal, AD0–7, output from microprocessor 960 on line 994, is input to latch 1018. The AD0–7 signal may contain address or data information. When it contains address information and the values are input to latch 1018, when that latch is clocked, the latched values are placed on address bus 1022.

The AD0–15 signals also connect to data bus 1028 via bus 1020 and bus transceivers 1024 and 1025. Bus transceiver 1024 controls transfers between the AD0–7 signals on bus 1020 and the data bus. Bus transceiver 1025 controls transfers between the AD8–15 signals on bus 1020 and the data bus. Bus transceivers 1024 and 1025 are enabled by the DEN bar signal on line 997. The direction of the data transfer is controlled by the DT/R (R bar) signal on line 996.

Decoders 1032 and 1036 are used to enable RAMs 1050 and 1052, respectively. The LCS bar signal on line 1008 enables both decoders. The first control signal input to decoder 1032 is the A0 signal from the address bus. The second control input is tied to ground. These signals are decoded to provide an input to the chip enable input of RAM 1050. Whether reading or writing is the proper action is determined by the logic states of the RD bar and WR bar signals input to RAM 1050.

The first control signal input to decoder 1036 is the the BHE bar signal on line 1010. The second control input is tied to ground. These signals are decoded to provide an input to the chip enable input of RAM 1052. Similarly, whether reading or writing is accomplished depends on the logic states of the RD bar and WR bar signals input to RAM 1052.

Third decoder 1040 enables ROMs 1046, 1048, 1054, and 1056. The UCS bar signal output from microprocessor 960 on line 976 enables decoder 1040. The control inputs to decoder 1040 are the A17, A18 and A19 signals from address bus 1022. When the control inputs are decoded, decoder 1040 provides outputs to enable the ROMs. Whether an enabled ROM can be read depends on the logic state of the RD bar signal input to the OE bar input of each ROM.

Referring to FIG. 8B, controller 1059 will be discussed. The Q output of flip flop 1058 clocks controller 1059. The CLK8 signal on line 1012 clocks flip flop 1058. The Q bar output and data input of this flip flop are tied. Hence, the Q output will provide a positive-going edge to clock controller 1059 every two CLK8 pulses.

The RESET signal on line 825 output from microprocessor 960 is input to to inverter 1007. Inverter 1007 changes the logic state of the RESET signal; accordingly, the RESET bar signal is input to the RESET bar input of controller 1059.

The WR bar signal on line 1004 and the RD bar signal on line 1006 are input to controller 1059. These signals control whether data is transmitted from or received by controller 1059.

The UART SEL signal on line 998 is input to controller 1059 for chip selection and enabling reading from and writing into memory.

The parallel 2-bit address bus signal, A12 and A13, from address bus 1022 is input to controller 1059. These are the address bus bits that control data flow. The parallel 8-bit data bus signal, D0–7, on line 1028 is input to controller 1059. These are the data bus bits which are either read from or written onto.

The DRQ0 signal on line 964 and the DRQ1 signal on line 966 are input to microprocessor 960 for notifying the microprocessor that data is ready to be transmitted from memory or that data is ready to be sent to memory.

The other signals that are output from or input to controller 1059 are primarily associated with communicating with the display section or an external device.

The INT CLK signal on line 1060 is the internal baud rate clock for synchronous serial communications between the analog and display processors.

The TxD INT signal on line 1062 is the line on which data is transmitted from the analog processor to the display processor.

The RxD INT signal on line 1064 is the line on which data is received from the display processor.

The information in the TxD INT signal on line 1062, the RxD INT signal on line 1064, and the INT CLK signal on line 1060 is communicated between analog processing circuitry 124 and display processing circuitry 128 using these signals because the analog and the display sections are electrically isolated.

The TxD INT signal is input to inverters 1080 and 1082 and then opto-isolator 1084. The TxD INT signal on the display side of opto-isolator 1084 is renamed the RXD INT signal on line 1086. A portion of data contained in the TxD INT signal is ultimately displayed on the CRT.

The RxD INT signal on line 1064 contains data received from the display processing circuitry. The signal starts as the TxD INT signal on line 1094 on the display side. The signal is input to inverters 1092 and 1090, and then opto-isolator 1088. At the output of opto-isolator 1088, the signal is renamed the RxD INT signal on line 1064.

The INT CLK signal on line 1060 is used to synchronously control transfer of data between the analog and display processing circuitry. The INT CLK signal on line 1078 on the display side is input to inverters 1074 and 1072, and then input to optoisolator 1070. The signal is output from the optoisolator on line 1060 for input to controller 1059.

The UART CLK signal on line 968 is input to controller 1059 and along with TxDB signal on line 1066 and the RxDB signal on line 1068 are for communications with external module 430 (FIG. 4A).

The UART CLK signal on line 968 is the baud rate clock for serial communications with the external module. The TxDB bar is for transmitting data to the external module. The RxDB bar signal is for receiving data from the external module.

The UART INT signal on line 962 is the UART INT bar signal output from controller 1059 after inversion by inverter 963. This signal is an interrupt signal to microprocessor 960 to indicate that data is ready to be sent or received.

The BATT SEN signal on line 842, and the FLOW PRS signal on line 391 and FLOW PRS RTN signal on line 393, cross the analog processing circuitry enroute to the analog input circuitry where they are processed.

The AIR PUMP SPEED signal on line 938 from analog switch 926 (FIG. 7D) is input to the base of transistor 1114. This signal controls the SAMPLE PUMP+ voltage on line 1122. The SAMPLE PUMP− signal on line 1124 is tied to ground. The power delivered by the circuit is limited by fuse 1116 in line 1122 and by zener diodes 1118 and 1120. The voltage across these lines controls the speed of sample pump 358. (FIG. 4A).

The D0 signal from data bus 1028 and the PCS5 signal from microprocessor 960 are input to the protection circuit 1125 according to a preset rate and duty cycle. The protection circuit, according to the clock rate of the PCS5 signal, evaluates the D0 signal. If D0 has values indicative of improper operation or the PCS5 signal is absent, it indicates that the microprocessor is in an improper loop and not carrying out its required functions, the FST A signal on line 972 will change logic states. This will cause the activation of the appropriate alarms to indicate this condition.

The SAR CLK signal on line 890 (FIG. 8A) which turns the internal clock of successive approximation register 870 on and off is generated by the CLK 400 signal and the SAR CLK ENBL signal. The CLK 400 signal on line 970 and the SAR CLK ENBL signal on line 888 are input to NAND gate 1110. The logic states of these signals control the output of NAND gate 1110. The output of NAND gate 1110 is inverted by inverter 1112 whose output is the SAR CLK signal on line 890.

The analog processing circuitry generates the control signals for powering certain components of the pump module. These are the diagnostic valve, the external valve 1, the external valve 2, and the backflush pump. The WR bar signal on line 1004 and the PUMP-/VALVE SEL signal on line 984 are input to negative-true AND gate 1095. The output of negative-true AND gate 1095 is inverted by inverter 1096 and input to the clock input of 8-bit flip flop 1098 of which only 4-bits are output lines. The data input to flip flop 1098 are the D0-7 signals from the data bus. When the flip flop is clocked, the data bus logic values determine which valves will be powered. Accordingly, the outputs of flip flop 1098 which are destined for the pump module are the DIAGNOSTIC VALVE signal on lines 411, the EXTERNAL VALVE 1 signal on line 431, the EXTERNAL VALVE 2 signal on line 441, and the BACKFLUSH signal on line 417.

The analog processing circuitry generates "select" signals, and the RD bar and WR bar signals for use by the analog input circuitry. The analog processing circuitry provides the 2-bit address bus signal for use by the analog input circuitry and bi-directionally communicates with analog input circuitry data bus.

The ADSEL' bar signal on line 1000, the GAIN SEL' bar signal on line 980, the PREAMP SEL' bar signal on line 978, and the MISC SEL' bar signal on line 1002 are input to OR gate 1100 and to octal buffer 1108. The other four inputs to octal buffer 1108 are the A1 and A2 signals from address bus 1022, the RD bar signal on line 1006, and the WR bar signal on line 1004.

The data bus signals D0-7 on line 1028 are input to bus transceiver 1106. The DT/R (R bar) signal controls the direction of data flow through the transceiver. The output of OR gate 1100 is inverted by inverter 1102 and input to the output enable inputs to bus transceiver 1106 and octal buffer 1108.

When at least one of the four "select" signals has the proper logic state, the bus transceiver and the octal buffer are output enabled; accordingly, data, control signals, and select signals are communicated between the analog input and analog processing circuitry. On the analog input side, these signals are the AID0-7 data bus signal on line 732, the AIA1-2 address has signal on line 828, the AIRD bar signal on line 824, the AIWR bar signal on line 830, the ADSEL bar signal on line 872, the GAIN SEL bar signal on line 940, the PREAMP SEL bar signal on line 892, and the MISC SEL signal on line 822.

FIG. 8C shows the circuit for generating the PCLK signal used to clock latch 900 for placing information on the optical bench data bus. The PATT SEL signal on line 974 is input to inverter 1130. The output of this inverter is the first input to NAND gate 1132. The WR bar signal on line 1004 is input to inverter 1134. The output of this inverter is the second input to NAND gate 1132. The output of NAND gate 1132 is input to the clock input to 8-bit flip flop 1136. The data bus signal D0-7 is input to the data inputs of the flip flop. The output of the flip flop on line 1138 is a parallel 4-bit signal to the address inputs of EPROM 1142.

The other input to EPROM 1142 is the parallel 8-bit output from 8-bit counter 1140 which is input to the data inputs. 8-bit counter 1140 is clocked by the CLK 400 signal output from microprocessor 960.

8-bit counter 1140 comprises two 4-bit counters. The terminal count of one 4-bit counter is tied to the clock input of the other 4-bit counter. Thus, the second 4-bit counter is clocked every sixteen clocks.

The parallel 8-bit output of EPROM 1142 is input to 8-bit flip flop 1144. 8-bit flip flop 1144 is clocked by the same signal that clocks the first 4-bit counter of 8-bit counter 1140. The PCLK signal output on line 902 clocks latch 900 (FIG. 7D).

The primary function of microprocessor 960 of analog processing circuitry 124 is calculating the partial pressures of the gases of interest. In calculating these, the microprocessor corrects for collision broadening, temperature, pressure in the gas pathway, cross-correction, barometric pressure, and characterization.

Characterization allows for the interchangeability of optical benches without the need for calibration. Characterization coefficients of an optical bench are based on the fact that a manufacturer constructs each optical bench of a particular type with the same components. However, corresponding components in two different benches have different responses. The result is that two different benches making partial pressure measurements can derive two different values even though both are operating properly.

Accordingly, each bench as its own specific characterization coefficients. These coefficients are stored in EEPROM 580 (FIG. 5A). Hence, the application of each bench's characterization coefficients to raw measurements of a known gas standard bring about the same result. This result is consistent with industry standards and made without any calibration to the bench's components.

Specific characterization coefficients for each gas channel are stored in EEPROM 580. The other values stored in the EEPROM 580 are the temperature transducer voltage at the reference temperature, the collision broadening coefficients, the cross-correction coefficients, and the span factor and offset for correcting pressure measurements.

The calculation of the partial pressure and gas concentration of $CO_2$ and $N_2O$ will now be discussed.

The $CO_2$ and $N_2O$ scale factors are measured and stored every time a zero gas measurement is calculated. Scale factors are determined by the following expression:

$$\text{Scale Factor } [X] = V[X_{gas}]/V[X_{ref}] \quad (1)$$

where,
 $X = CO_2$ or $N_2O$.
 $V[X_{gas}]$ = the measured gas channel output of the detector with zero gas.
 $V[X_{ref}]$ = the measured reference channel output of the detector with zero gas.
 Scale Factor $[X]$ = is a real number value.

At predetermined intervals, the system calculates updates for temperature related values used in calculating the partial pressure of each gas. These values are calculated according to the following three expressions:

$$\Delta T = V[Tmp] - RefTmpVolts \quad (2)$$

where,
 $V[Tmp]$ = the current measured voltage from the temperature sensor.
 $RefTmpVolts$ = The voltage for the reference operating temperature of the optical bench stored in EEPROM 580.

$$tcB[X] = B_o[X] + ((B_1[X])(\Delta T)) + ((B_2[X])(\Delta T^2)) \quad (3)$$

where
 $X = CO_2$ or $N_2O$.
 $B_o[X], B_1[X], B_2[X]$ = the B characterization coefficients for each gas stored in EEPROM 580.
 $tcB[X]$ = the B temperature correction for each gas.

$$tcC[N_2O] = C_o[N_2O] + ((C_1[N_2O])(\Delta T)) + ((C_2[N_2O])(\Delta T^2)) \quad (4)$$

where
 $C_o[N_2O], C_1[N_2O], C_2[N_2O]$ = the C characterization coefficients for $N_2O$ stored in EEPROM 580.
 $tcC[N_2O]$ = the C temperature correction for $N_2O$.

The C temperature correction is only calculated for $N_2O$. The C temperature correction for $CO_2$ has negligible effect on the final partial pressure of $CO_2$, so it is not used.

At predetermined intervals, collision broadening calculations are performed. These calculations are carried out according to the following three expressions:

$$\text{If } PP[N_2O] > 76 \text{ mmHg, then } CB[N_2/O_2] = \emptyset \quad (5)$$

where
 $PP[N_2O]$ = the average $PP[N_2O]$ over the updated time interval.
 $CB[N_2O_2]$ = the collision broadening factor for $N_2$ and $O_2$.

$$\text{Else, } CB[N_2O_2] = ((cbL)(1 - (O_2\%/100))) \quad (6)$$

where
 $CB[N_2/O_2]$ = the collision broadening factor for $N_2$ and $O_2$.
 $cbL$ = the collision broadening coefficient stored in EEPROM 580.
 $\%O_2$ = the measured $\%O_2$ from a peripheral device, or a manually set percentage, or 50% as a default value in the programming.

$$CB[N_2O] = ((cbM)(PP[N_2O]''))/SampleCellPrs \quad (7)$$

where
 $CB[N_2O]$ = the collision broadening factor for $N_2O$.
 $cbM$ = the collision broadening coefficient for $N_2O$ stored in EEPROM 580.
 $PP[N_2O]''$ = the current $N_2O$ calculation (mmHg).
 $SampleCellPrs$ = the pressure measured in the sample cell (optical bench) when the gas voltages are measured.

$$CB[CO_2] = ((cbN)(PP[CO_2]''))/SampleCellPrs \quad (8)$$

where
 $CB[CO_2]$ = the collision broadening factor for $CO_2$.
 $cbN$ = the collision broadening coefficient for $CO_2$ stored in EEPROM 580.
 $PP[CO_2'']$ = the current $CO_2$ calculation (mmHg).
 $SampleCellPrs$ = the pressure measured in the sample cell (optical bench) when the gas voltages are measured.

The absorption of light by the $CO_2$ and $N_2O$ gas is continuously calculated according to the expression:

$$R[X] = -\ln(V_{gas}[X]_{inst}/((V_{ref}[X]_{inst}) \quad (9)$$
$$(\text{Scale Factor }[X]))$$

where,
 $X = CO_2$ or $N_2O$.
 $V_{gas}[X]_{inst}$ = the instantaneous demodulated gas voltage for $CO_2$ or $N_2O$.
 $V_{ref}[X]_{inst}$ = the instantaneous demodulated reference voltage for $CO_2$ or $N_2O$.
 Scale Factor $[X]$ = the current scale factor value for $CO_2$ and $N_2O$.

Having made the above calculation, microprocessor 960 calculates the partial pressure of $CO_2$ and $N_2O$. In the expressions that follow, a partial pressure shown as $PP[X]$ is a final partial pressure corrected for cross-correction and collision broadening; a partial pressure shown as $PP[X]'$ is a partial pressure corrected for collision broadening only; and a partial pressure shown as $PP[X]''$ is corrected for neither.

The partial pressure of $CO_2$ and $N_2O$ are calculated according to expressions (10)–(22). The uncorrected $CO_2$ partial pressure is calculated according to the expression:

$$PP[CO_2]'' = ((tcB[CO_2])(R[CO_2])) + \quad (10)$$
$$((C_o[CO_2])(R[CO_2]^2)) +$$
$$((D[CO_2])(R[CO_2]^3))$$

where,
 $tcB[CO_2]$ = the B temperature correction for $CO_2$.

$R[CO_2]$ = $CO_2$ light absorption.
$C_o[CO_2]$ = the C characterization coefficient for $CO_2$ stored in EEPROM 580.
$D[CO_2]$ = the D characterization coefficient for $CO_2$ stored in EEPROM 580.

The uncorrected $N_2O$ partial pressure is calculated according to the expression:

$$PP[N_2O]'' = ((tcB[N_2O])(R[N_2O])) + \qquad (11)$$
$$((tcC[N_2O])(R[N_2O]^2)) +$$
$$((D[N_2O])(R[N_2O]^3))$$

where,
$tcB[N_2O]$ = the B temperature correction for $N_2O$.
$R[N_2O]$ = $N_2O$ light absorption.
$tcC[N_2O]$ = the C temperature correction for $N_2O$.
$D[N_2O]$ = the D characterization coefficient for $N_2O$ stored in EEPROM 580.

The uncorrected $CO_2$ partial pressure is now corrected for collision broadening by the expression:

$$PP[CO_2]' = ((PP[CO_2]'')(1+CB[N_2O])(1+CB[N_2/O_2]))/((1-CB[N_2O])(CB[CO_2])) \qquad (12)$$

where
$CB[N_2O]$ = the collision broadening factor for $N_2O$.
$CB[CO_2]$ = the collision broadening factor for $CO_2$.
$CB[N_2/O_2]$ = the collision broadening factor for $N_2$ and $O_2$.

The final $CO_2$ partial pressure, corrected for cross-correction, is calculated by the expression:

$$PP[CO_2] = PP[CO_2]' - ((PP[N_2O]'')(CCrsCorr[N_2O])) \qquad (13)$$

where,
$CCrsCorr[N_2O]$ = the cross-correction for $N_2O$ in the $CO_2$ channel stored in EEPROM 580.

The uncorrected $N_2O$ partial pressure is now corrected for collision broadening by the expression:

$$PP[N_2O]' = ((PP[N_2O]'')(1+CB[CO_2]))/((1-CB[N_2O])(CB[CO_2])) \qquad (14)$$

where
$CB[CO_2]$ = the collision broadening factor for $CO_2$.
$CB[N_2O]$ = the collision broadening factor for $N_2O$.

The final $N_2O$ partial pressure, corrected for cross-correction, is calculated by the expression:

$$PP[N_2O] = PP[N_2O]' - ((PP[CO_2])(NCrsCorr[CO_2])) \qquad (15)$$

where,
$NCrsCorr[CO_2]$ = the cross-correction for $CO_2$ in the $N_2O$ channel stored in EEPROM 580.

Once the final partial pressures for $CO_2$ and $N_2O$ are calculated, each is corrected to barometric pressure. The barometric pressure value that is normally used in correcting the final partial pressure of $CO_2$ and $N_2O$ is calculated by the following expression:

$$\text{Barometric Prs}_N = ((V[Prs]_{NP})(PrsSpn)) + PrsOffset \qquad (16)$$

where,
$V[Prs]_{NP}$ = the voltage from pressure transducer 374 at system start-up or an update with the sample pump off that is stored in memory.

PrsSpn = the pressure span factor to characterize pressure transducer 374 that is stored in EEPROM 580.
PrsOffset = the offset for pressure transducer 374 that is stored in EEPROM 580.

However, in certain situations, for example, when the optical bench is used in an open military field hospital in a high humidity area, the barometric pressure calculated according to expression 16 must be further corrected to be accurate. Under such circumstances, the barometric pressure is calculated by the following two expressions:

$$H_2O\ VaporPrs = ((RelHum)(SatPrs)(\text{Barometric Prs}_N 30\ \text{SampleCellPrs}_{aver}))/1520 \qquad (17)$$

where,
RelHum = the relative humidity which is normally the default value of 45%. This can also be the measured value of relative humidity which is manually input by the operator
SatPrs = the vapor pressure of water at standard pressure which is normally the default value of 11.837 mmHg. The vapor pressure can also be a determined value of the vapor pressure of water at standard pressure which is manually input by the operator.
Barometric $Prs_N$ = last measured barometric pressure stored in memory.
SamplCCellPrs$_{aver}$ = the average pressure measured in the sample cell (optical bench) when the barometric pressure measurements were taken.

The further corrected barometric pressure is calculated by the following expression:

$$\text{Barometric Prs}_S = \text{Barometric Prs}_N - H_2O\ VaporPrs \qquad (18)$$

where,
Barometric $Prs_N$ = last measured barometric pressure stored in memory.
$H_2O$ VaporPrs = the vapor pressure of water calculated according to expression 17.

The final partial pressure of a gas of interest is corrected for (normal) barometric pressure according to the following expression:

$$PPmmHg[X] = \frac{(PP[X])}{(SampleCellPrs)}(\text{Barometric Prs}_N) \qquad (19)$$

where,
$X = CO_2$ or $N_2O$.
SampleCellPrs = the pressure measured in the sample cell (optical bench) when the gas voltages are measured.
Barometric $Prs_N$ = the last measured barometric pressure stored in memory.

The % concentration of $CO_2$ and $N_2O$ can be chosen for display rather than the PPmmHg[X] calculated according to expression 19. The % concentration is calculated according to the expression:

$$\%\ Conc[X] = \frac{((PPmmHG[X])(100))}{(\text{Barometric Prs}_N)} \qquad (20)$$

where,
$X = CO_2$ or $N_2O$.
Barometric $Prs_N$ = the last barometric pressure stored in memory.

PPmmHg[X] = the final partial pressure of $CO_2$ or $N_2O$ in mmHg corrected for barometric pressure.

For the purpose of calculating the final partial pressure of $CO_2$ or use in generating the scrolling waveform on the screen display (FIG. 17), the detected $CO_2$ gas signals are corrected only for $N_2O$ collision broadening. However, this collision broading is different from the collision broadening factor discussed previously in, for example, expression 12. For the scrolling waveform, collision broading is determined by the following expression:

$$CB[N_2O]_{wave} = (cbM)(Conc[N_2O]_{aver}) \quad (21)$$

where, cbM = the collision broadening coefficient for $N_2O$ stored in EEPROM 580.

$Conc[N_2O]_{aver}$ = the average end-tidal $N_2O$ from the last breath stored in memory.

The final partial pressure of $CO_2$ for use in generating the scrolling $CO_2$ copnogram is calculated according to the following expression:

$$PP[CO_2] = (PP[CO_2]'')(1 + CB[N_2O]_{wave}) \quad (22)$$

where, $PP[CO_2]''$ = the uncorrected partial pressure of $CO_2$ according to expression 10.

$CB[N_2O]_{wave}$ = the collision broadening factor for generating the scrolling $CO_2$ waveform according to expression 21.

As stated, the above calculations are made by microprocessor 960. Once these calculations are made, they are transmitted to the display section for display.

The measured values for optical bench pressure is also corrected by microprocessor 960 and sent to the display section. Further, the measured temperature (in volts) is sent to the display section. These values are used for diagnostic purposes only.

The pressure within the optical bench pathway can vary between +12.2 psia and +9.7 psia. When the sample respiratory gas stream or zero gas stream is drawn through optical bench 111 by sample pump 358 the pressure is within this range. The expression for calculating pressure within optical bench 111 is:

$$Press = ((V[Prs])(PrsSpn)) + PrsOffset \quad (23)$$

where,

V(Prs) = the instantaneous voltage from pressure transducer 374.

PrsSpn = the pressure span factor to characterize the pressure transducer that is stored in EEPROM 580.

PrsOffset = the offset for the pressure transducer that is stored in EEPROM 580.

FIGS. 9A–E show the circuits contained on motherboard 137 (FIG. 1). The circuitry on motherboard 137 communicates between the analog processor circuitry 124 and display processor circuitry 128, between two or more elements in the display section circuitry and between the display processor 128 and the knob board 144.

Referring to FIG. 9A, the signals input to speaker driver circuit 1354 are the $V_{VOL}$ signal on line 1350 and the $V_{BEEP}$ signal on line 1352. The $V_{BEEP}$ signal is the principal signal driving speaker driver circuit 1354. The $V_{VOL}$ signal adjusts the SPK+ voltage on line 1356. The SPK− output on line 1358 connects to ground.

The SPK+ and SPK− lines connect to an external speaker.

The video amplifier circuit 1364 is for driving the CRT cathode. The signals input to the video amplifier circuit are the VIDEO OUT signal on line 1360 and the $V_{CONTR}$ signal on line 1362. The VIDEO OUT signal on line 1366 is the signal for driving the display screen. The $V_{CONTR}$ signal on line 1362 controls the voltage supplied to the cathode for the purpose of screen contrast. The output of this circuit to the CRT cathode is on line 1366.

The H.DRIVE (horizontal drive) signal on line 1371 from CRT controller 1998 of pixel circuitry 130 is input to horizontal drive circuit 1372. Following conventional processing by this circuit, the signal is input to horizontal output circuit 1376. The outputs of the horizontal output circuit are to the CRT anode on line 1380, to CRT grids 1, 2, and 4 on lines 1382, 1384 and 1388, respectively, and the HORIZ+ and HORIZ− signals on lines 1340 and 1342 to the horizontal yoke.

The V.SYNC (vertical sync) signal on line 1344 is input to vertical output circuit 1347. The $V_{DEFL}$ (deflection voltage) signal on line 1345 is input to voltage regulator 1349. The output of the voltage regulator is input to the control voltage inputs to the vertical output circuit. Following conventional processing by this circuit, the output signals are the VERT− and VERT+ signals on lines 1346 and 1348, respectively. These signals are input to the vertical yoke.

The apparatus cooling fan supply voltage is supplied from the CRT mother board. The FAN+ signal on line 1361 is connected to a +12 v supply voltage. The FAN− signal on line 1363 is tied to ground. Accordingly, a 12 v supply voltage is across the fan terminals to power it.

Figures 9B, 9D:
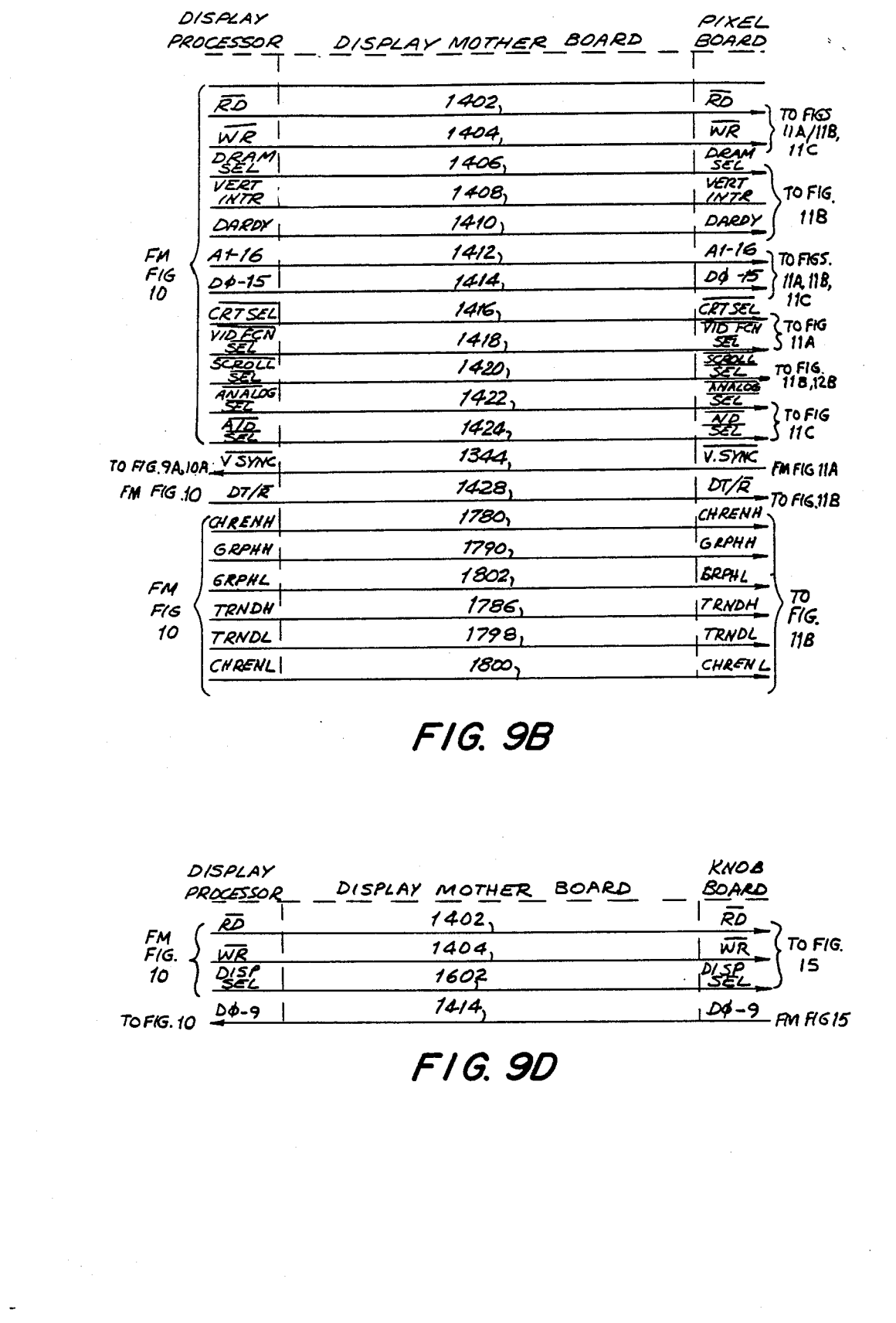
Figure 9C:
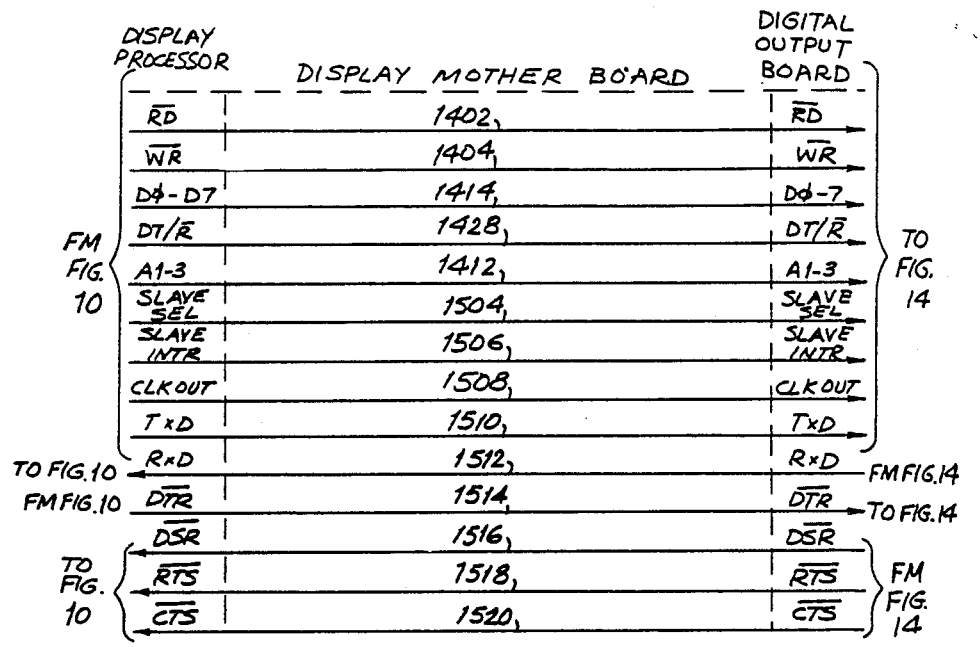
Figure 9E:
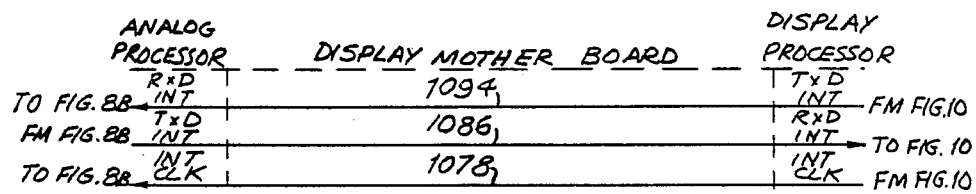

FIGS. 9B–9E show signals which transit the motherboard without being processed by its circuitry. FIG. 9B shows signals communicated between display processing circuitry 128 and pixel circuitry 130. FIG. 9C shows signals communicated between display processing circuitry 128 and digital output board 140. FIG. 9D shows signals communicated between the display processing circuitry and knob board 144. FIG. 9E shows signals communicated between analog processing circuitry 124 and display processing circuitry 128.

FIGS. 10A and 10B are schematic diagrams of display processing circuitry 128. The principal functions of the display processing circuitry are processing the incoming data from analog processing circuitry 124, transmittal of the data back to the analog processing circuitry, and control of pixel circuitry 130.

The partial pressure of $CO_2$ and $N_2O$, the pressure within the optical bench, the gas flow rate through the optical bench and other information for display are received as the RxD INT signal on line 1086 by controller 1776. Data sent to the analog processing circuitry is sent via the TxD INT signal on line 1094 from controller 1776.

When the control signals input to controller 1776 have the proper states, data is transmitted to or received from the 8-bit data bus shown as D0–7 on line 1414.

The INT CLK signal on line 1078 synchronizes the transmission of data between the analog and the display processing circuitry.

The DRQ0 and DRQ1 signals output from the controller on lines 1730 and 1732, respectively, the 2 address bus signals A12 and A13 input to the controller, the COMM INTR signal output on line 1706, the COMM SEL signal input on line 1778, and the RD bar and WR bar signals on lines 1402 and 1404, respectively, all operate conventionally in a manner known by those skilled in the art. The TxD signal on line 1510, the RxD signal on line 1512, the DTR bar signal on line 1514, the DSR bar signal on line 1516, the RTS bar signal on line 1518 and the CTS bar signal on line 1520 all connect to the digital output board 140. These signals are for communications with and control of an external device.

The EXT CLK signal on line 1734 is a clock signal for controlling serial communications between the controller and an external device.

Microprocessor 1702 is a model 80186 CPU, commercially available from INTEL Corporation, Santa Clara, Calif. The signals input to and output from microprocessor 1702 will now be discussed.

When microprocessor 1702 is powered on, the RESET OUT signal on line 1704 is asserted. The RESET OUT signal on line 1704 is input to inverter 1707. The output of the inverter is the RESET bar signal on line 1705. This signal is input to the RESET bar input of controller 1776.

The VERT INTR signal on line 1408, the V.SYNC bar signal on line 1344, and the SLAVE INTR signal on line 1506 are all interrupt signals. The VERT INTR signal is the interrupt signal to microprocessor 1702 to indicate when the end of the scrolled window is reached. The V.SYNC bar signal on line 1344 indicates the end of a display field on the CRT. The SLAVE INTR signal on line 1506 is the interrupt signal from an external device.

The COMM INTR signal on line 1706 is the signal input into the microprocessor from the controller through inverter 345 to indicate that data is being transferred from or received by the controller.

The DARDY signal on line 1410 is the asynchronous ready signal.

The UCS bar signal output on line 1710 enables decoder 1746. The signals output from this decoder based on the logic values of the address bus bits A17 and A18 enable ROMs 1760, 1762, 1764 and 1766.

The D. SIDE OFF signal on line 1712 is output to the battery control circuit to indicate shut down of the display side of the system.

The DISP SEL signal on line 1602 is output to the knob board for placing the button and knob status on the data bus and for the display and activation of the system's audible and visual alarms.

The VID FCN SEL signal on line 1418, the CRT SEL signal on line 1416, the A/D SEL signal on line 1424, the SCROLL SEL signal on line 1420, and the ANALOG SEL signal on line 1422 are output to the motherboard for input to, and control of, pixel circuitry 130.

The CRT SEL signal on line 1416 is input to CRT controller 1998 (FIG. 11A) for chip selection. The VID FCN SEL signal is input to decoder 2032 (FIG. 11A) to select a proper video display function for the CRT screen. The A/D SEL signal on line 1424 is used to put ECG information or battery comparison information on the data bus for transfer to memory (FIG. 11C). The ANALOG SEL signal on line 1422 is used to control selection among various analog output ports.

The FST B signal on line 1709 is input to microprocessor protection circuit 1717. This changes logic states when the microprocessor is not performing its required functions, e.g., the microprocessor is improperly looping. This circuit is similar to protection circuit 1125 that protects microprocessor 960 (FIG. 8B).

The other signals associated with microprocessor 1702 yet to be described are signals for one of the buses or signals associated with accessing memory to read or write data.

The signals A16/S3–A19/S6, a parallel 4-bit output on line 1713, are the high order address bits. These bits are input to latch 1740. When this latch is clocked by the ALE (address latch enable) signal on line 1718, the address information is placed on the address bus since the OE bar input is tied to ground.

The DEN bar (data enable) signal on line 1714 is the output enable signal for bus transceivers 1752 and 1754. The DT/R (R bar) (data transmit/receive) signal on line 1428 determines the direction of data flow through bus transceivers 1752 and 1754. Together, these two signals control the data transmitted to and received from memory on address/data busses 1720, 1722 and 1723.

When address/data busses 1722 and 1720 are used for address rather than data transfer, address bits ∅–7 are input into latch 1744 and address bits 8–15 are input to latch 1742. When these latches are loaded and then clocked by the ALE signal on line 1718, the latched values are placed on the address bus.

RAM 1768 is enabled by the output of decoder 1794. This decoder is enabled by the output of decoder 1784. Decoder 1784 is enabled by the output of OR gate 1780, address bit A19 and the BHE bar (bus high enable) on line 1724.

RAM 1770 is enabled by the output of decoder 1804. This decoder is enabled by the output of decoder 1796. The signals that enable decoder 1796 are the output of OR gate 1780, and the A∅ and A19 signals on line 1412 from the address bus.

The inputs to OR gate 1780 are the MCS∅–MCS3 bar signals output from microprocessor 1702 on line 1726. As stated, the output of OR gate 1780 output enables decoders 1784 and 1796. The states of the outputs from these decoders are controlled by high-order address bits A17 and A18 on line 1412.

The other outputs of decoder 1784 are the TRNDH (trend high) signal on line 1786, the CHRENH (character/enhancement plane high) signal on line 1788 and the GRPHH (graphic plane high) signal on line 1790. These signals are also input to OR gate 1792. The word high in these signal names indicates the high-order address bits, 8–15, for a particular memory circuit in pixel circuitry 130.

The other outputs of decoder 1796, are the GRPHL (graphic plane low) signal on line 1802, the CHRENL (character/enhancement plane low) signal on line 1800 and the TRNDL (trend low) signal on line 1798. These signals are also input to OR gate 1792. The word low in these signal names indicates the low-order address bits, ∅–7, for a particular memory circuit in pixel circuitry 130.

The output of OR gate 1792 is the DRAM SEL (dynamic RAM select) signal on line 1406. The DRAM SEL signal is used in conjunction with other signals to select and write from a particular DRAM to the pixel memory circuits.

Decoder 1804 has three other outputs. These are the FST SEL signal on line 1711, and the previously discussed COMM SEL signal on line 1778 and SLAVE SEL signal on line 1504. These signals are output from the decoder when it is not being used to enable RAM 1770 and the respective cirucit is activated.

The FST SEL (fail safe timer select) signal is input to the protection circuit 1717. The second input to this circuit is the D∅ signal from the data bus. At a clock rate determined by the FST SEL signal the D∅ signal is checked. This is done to determine if microprocessor 1702 is not performing its required functions. The FST B signal on line 1709 is output from the protection circuit and input to microprocessor 1702.

The BHE bar (bus high enable) signal on line 1724 also assists in enabling RAM 1768 when the high order bits D8-15 are written onto or read.

The CLK OUT signal on line 1508 is the main clock signal for operating the display processor circuitry. The CLK OUT signal, through flip flop 1781, clocks controller 1776. However, because the data input and the Q bar output are tied, the controller is clocked every two CLK OUT pulses.

ROMs 1760, 1762, 1764 and 1766 and RAMs 1768 and 1770 are connected to data bus 1414 and address bus 1412 conventionally.

Figure 11B:
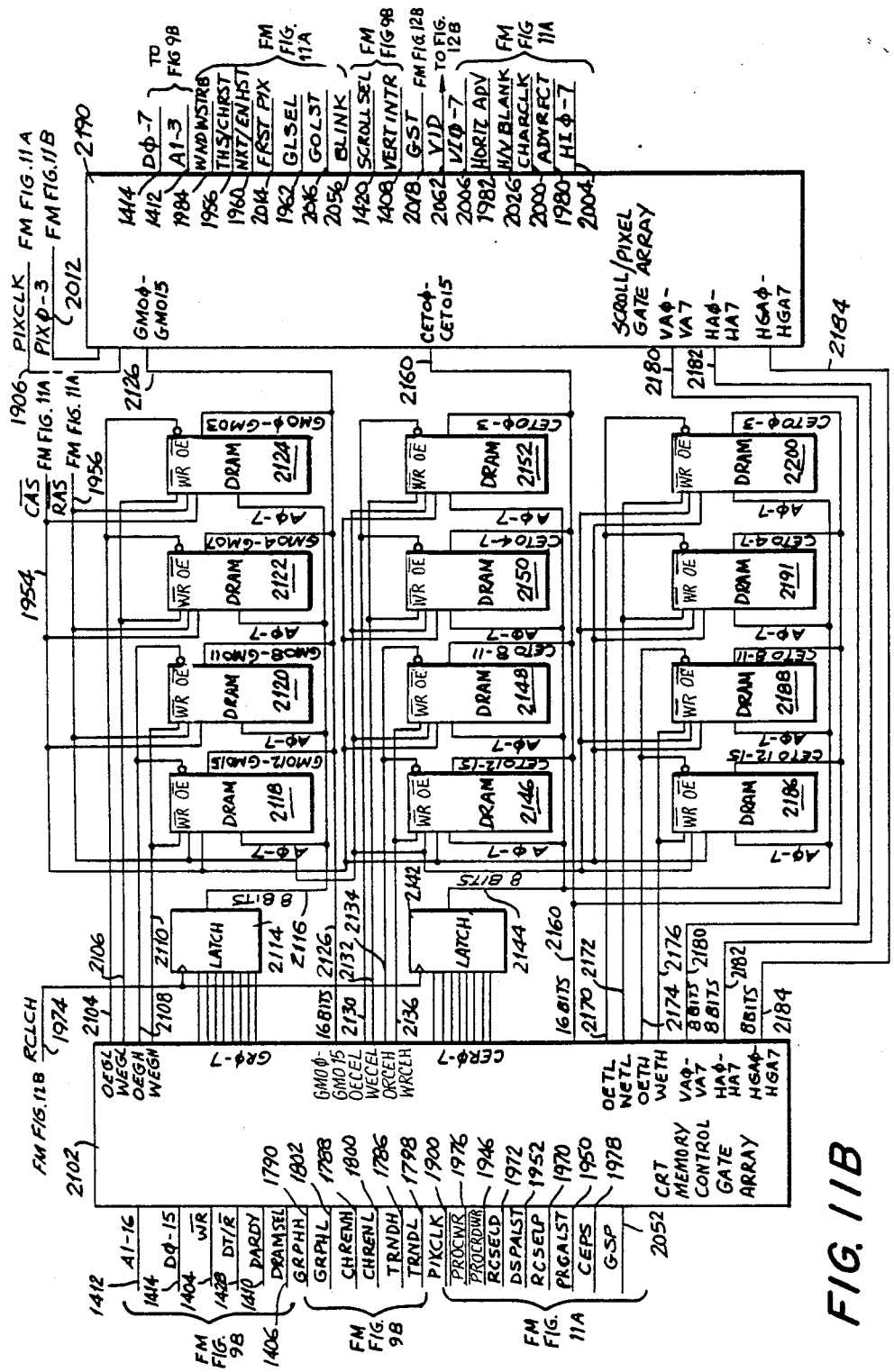

FIGS. 11A, 11B, and 11C show pixel circuitry 130. FIG. 11A shows the circuitry that generates a majority of the signals used by the circuitry shown in FIG. 11B.

The graphic plane refers to the scrolled information on the display screen. The character and enhancement planes refer to the fixed characters on the display screen.

Referring to FIG. 11A, the output of 24 MHz oscillator 1902, after being inverted by inverter 1904, is the PIX CLK signal on line 1906. This is the clock signal for clocking most of the pixel circuitry.

The PIX CLK signal clocks 4-bit counter 1908. The output signals from the 4-bit counter are input to PROMs 1910 and 1912, and latch 1926. The Q output of flip flop 2020 is also input to PROMs 1910 and 1912. PROMs 1910 and 1912 are enabled by a pull-up signal inverted by inverter 1940. The parallel 8-bit output of PROM 1910 is input to latch 1938. This latch is clocked by the PIX CLK signal. The following signals are output from this latch when clocked:

PROCRDWR bar (line 1946)—processor read/write. This provides a time window in which the processor can read from or write into memory.

PRCALST (line 1950)—processor address-latch strobe. It strobes the processor address latches.

DSPALST (line 1952)—display processor address-latch strobe. It strobes the display address latches.

CAS bar (line 1954)—column address latch strobe. It strobes the column address latches.

RAS bar (line 1956)—row address latch strobe. It strobes the row-address latches.

THS/CHRST (line 1958)—this/character strobe. It strobes different latches with data from the series of memories for the graphic and character planes.

NXT/ENHST (line 1960)—next/enhancement strobe. It strobes to latch the next graphic plane and enhancement plane data.

GLSEL (line 1962)—a graphic latch select. It selects which graphic data latch is used for a 16-pixel area of the display screen.

The 8-bit output of EPROM 1912 is input to latch 1964. This latch is clocked by the PIX CLK signal on the same clock pulse that latch 1938 is clocked. The 8-bit output of latch 1964 is input to latch 1968. This latch is clocked a half-clock pulse after latch 1964 because inverter 1936 is disposed in the clock line to latch 1968. The following signals are output by latch 1968:

RCSELP (line 1970)—row/column select for the processor memory.

RCSELD (line 1972)—row/column select for the display memory.

RCLCH (line 1974)—row/column select latch clock.

PROCWR bar (line 1976)—processor write. This signal is for writing data into the processor memory.

CEPS (line 1978)—character/enhancement plane select. This signal selects the proper character/enhancement plane.

ADVRFCT (line 1980)—the advanced refresh count. This signal is used by the DRAMs.

HORIZ ADV (line 1982)—horizontal advance. This signal runs the graphic plane address counter.

WNDWSTRB (line 1984)—window strobe. This signal strobes the current graphic display addresses.

The inputs to CRT controller 1998 will now be discussed.

The RD bar and WR bar signals on lines 1402 and 1404, respectively, are input to OR gate 1986. The output of this gate is inverted by inverter 1988. The output of the inverter is input to the data strobe input to the CRT controller 1998. Once configured, CRT controller 1998 outputs the horizontal address bits HI∅-7 on line 2004 and the vertical address bits VI∅-7 on line 2006. The contents of these signals are determined by the parallel 8 bit data bus signals D∅-7 on line 1414 and parallel 4 bit address A1-A4 on line 1412.

The CRT SEL signal on line 1416 is input to controller 1998 after inversion by inverter 1992. This signal selects the controller for access.

The CHAR CLK (character clock) signal on line 2000 is generated by the terminal count of 4 bit counter 1908. The CHAR CLK signal is used for clocking at a rate of 1/16th of the pixel rate. After being inverted, the CHAR CLK signal is input to the character clock input of controller 1998. It is also input to a data input of latch 1926 and the clock inputs of flip flops 2020 and 2024.

The data input to flip flop 2020 is the BLANK signal from controller 1998 on line 2002. This signal indicates the non-active portion of the horizontal and vertical scans. As stated, the Q output of flip flop 2020 is input to PROMs 1910 and 1912. The Q bar output of flip flip 2020 is input to the data input of flip flop 2024. The Q output of flip flop 2024 is the H/V BLANK bar signal on line 2026. This signal indicates the blank portions of the horizontal and vertical scans.

There are two other outputs from CRT controller 1998. The first is the V.SYNC bar signal on line 1344 (after being inverted by inverter 2010). The second is the H.SYNC signal on line 1370. The H.SYNC signal output on line 1320 is input to protection circuit 1373. This circuit prevents the H.SYNC signal from over driving the horizontal drive circuit. The output of the protection circuit is the H.DRIVE signal on line 1371. These signals are input to the CRT driver (FIG. 7A) for driving the screen display.

The H/V BLANK bar signal is also a data input to latch 2028. This latch is clocked by the PIX CLK signal. The output of the latch is delayed 3 clock pulses by a series of tied inputs and outputs of the latch. The output of this latch is input to OR gate 2046.

The other data input to latch 2028 is the GST signal on line 2018. When the latch is clocked by the PIX CLK signal the GOLST signal on line 2016 is output from the latch based on the logic value of the GST signal. The GOLST signal is the graphic plane output latch strobe signal. This strobes the current graphic plane output word.

The other input to OR gate 2046 is the Q bar output of flip flop 2042. This flip flop is clocked by the output of decoder 2032 on line 2040. This decoder selects the display video function.

The enabling input to decoder 2032 is the VID FCN SEL signal on line 1418. Depending on the state of address bits A1-3, one of the four functions is selected.

If line 2034 is selected, flip flop 2050 is clocked. The Q output of flip flop 2050 is the GPS (graphic plane select) signal on line 2052.

If line 2036 is selected, flip flop 2054 is clocked. The Q output of flip flop 2054 is the BLINK (display blink) signal on line 2056.

If line 2038 is selected, it will clock flip flop 2058. The Q bar output of flip flop 2058 is input to the SEL A/B (A bar) input of multiplexer 2068. The signals input to the data inputs of multiplexer 2068 are the VID signal on line 2062 (input to the A0 input) and its complement (input to the B0 input). The state of the selection input determines whether the A0 or B0 inputs is selected for output as the VIDEO OUT signal on line 1360.

If line 2040 is selected, flip flop 2042 is clocked. The Q bar output of flip flop 2042 is the second input to OR gate 2046.

The output of OR gate 2046 is the signal that enables multiplexer 2068 for output of the VIDEO OUT signal on line 1360.

The signal input to the data inputs of flip flops 2050, 2054, 2058 and 2042 is the D0 signal from the data bus.

The inputs to latch 1926 are the 4-bit output of 4-bit counter 1908 and the CHAR CLK signal on line 2000. This latch is clocked by the inverted PIX CLK signal. When clocked, the outputs of the latch are the pixel address PIX0-3 signals on line 2012 and the FRST PX signal on line 2014. The FRST PX signal represents the first pixel position for a word on the screen.

FIG. 11B shows CRT memory control gate array 2102, scroll/pixel gate array 2190 and a series of DRAMs and latches used by both gate arrays. Many of the signals input to and output from both gate arrays have been described. Those signals will not be redescribed here.

Again referring to FIG. 11B, DRAMs 2118, 2120, 2122 and 2124 are used for the graphic plane. DRAMs 2146, 2148, 2150, 2152, 2186, 2188, 2191, and 2200 are shared memory by the character and enhancement planes, and by the trend section.

The parallel 8 bit GR0-7 (graphic plane address( signal is input to latch 2114. When clocked, the latch places the latch address values on address bus 2116. The parallel 8 bit CER0-7 (character/enhancement plane address) signal is input to latch 2142. When this latch is clocked, it places the latched address values on address bus 2144. Both latches are clocked by the RCLCH signal on line 1974.

The parallel 16 bit GM00-15 signal on line 2126 is the 16 bit data bus that connects conventionally to the graphic plane DRAMs. The parallel 16-bit CET00-15 signal on line 2160 is the 16-bit data bus that connects conventionally to the character/enhancement/trend DRAMs. The CAS bar (column address strobe) signal on line 1954 and RAS bar (row address strobe) signal on line 1956 connected to each of the DRAMs and strobe them conventionally.

The high order data bits, D8-15, for the graphic plane DRAMs and the character/enhancement/trend DRAMs have separate output enable (OE bar) and write enable (WR bar) controls. This is also true for the low order bits, D0-7, for the graphic plane DRAMs and the character/enhancement/trend DRAMs. The following are the separate write enable and output enable signals for the DRAMs.

OEGL (line 2104)—output enable graphic plane low (low means bits GMO0-7).

WEGL (line 2106)—write enable graphic plane low.

OEGH (line 2108)—output enable graphic plane high (high means bits GMO8-15).

WEGH (line 2110)—write enable graphic plane high.

OECEL (line 2130)—output enable character/enhancement plane low (low means bits CET00-7).

WECEL (line 2132)—write enable character/enhancement plane low.

OECEH (line 2134)—output enable character/enhancement plane high (high means bits CET08-15).

WECEH (line 2136)—write enable character/enhancement plane high.

OETL (line 2170)—output enable trend low (low means bits CET00-7).

WETL (line 2172)—write enable trend low.

OETH (line 2174)—output enable trend high (high means bits CET08-15).

WETH (line 2176)—write enable trend high.

The additional lines between CRT memory gate array 202 and scroll/pixel gate array 2190 are the parallel 8 bit horizontal address bus HA0-7 on line 2182; the parallel 8 bit vertical address bus VA0-7 on line 2180; and the parallel 8 bit horizontal graphic address bus HGA0-7 on line 2184. The function of these address buses are known by one skilled in the art without further explanation.

FIG. 11C is a schematic diagram of the analog output section of pixel circuitry 130.

The inputs to decoder 2302 are the WR bar signal on line 1404, the ANALOG SEL signal on line 1422 and the control inputs address bits A4-6 on line 1412.

The WR bar and ANALOG SEL signals enable the decoder. The address bits A4-6 select the output of the decoder.

The output of decoder 2302 on line 2306 is input to the WR bar input of analog switch 2316. This signal causes the analog inputs to the switch to be output. This output depends on the states of the control inputs. The control inputs are the A1-3 signals from the address bus. The switch is enabled by the D0 signal on line 1414.

The decoder output on line 2308 is input to the WR bar input of analog switch 2780. Similarly, the analog inputs to the switch are output according to the states of the control inputs, the A1-3 signals from the address bus. The switch is enabled by the D0 signal on line 1414.

The decoder output on line 2304 is input to the WR bar and CS bar inputs of D/A convertor 2310. Data bits D0-11 from line 1414 are the data inputs to the converter. D/A converter 2310 converts the data bus inputs to analog signals which are output from the converter on line 2311. The output of D/A convertor 2310 on line 2311 is amplified by amplifier 2312 and input to the data inputs of analog switches 2316 and 2780.

When analog switch 2316 is enabled by the D0 signal and the WR bar input has the proper logic state, the latched values are output to the selected analog output lines. This energizes at least one of analog output ports 1-7, shown generally at 2322, after the signal has been processed by the appropriate sample and hold circuit, shown generally at 2320. The eighth analog output port is an I/O port for ECG signals.

Analog switch 2780 operates in the same manner as analog switch 2316, if line 2308 is selected by decoder 2302. Analog switch 2780 can select among four output lines; however, only three are actual output lines. The fourth, which is associated with ECG signals, is connected to the eighth analog output port. This port is for bi-directional communication of ECG information.

The first output of analog switch 2780 is associated with the $V_{BEEP}$ signal on line 1352, the second is associated with the $V_{VOL}$ signal on line 1350, and the third is associated with the $V_{CONTR}$ signal on line 1362. Each of the three outputs is processed by the appropriate sample and hold circuit shown generally at 2390.

When the ECG TRIG OUT signal is output from analog switch 2780, it is input to sample and hold circuit shown generally at 2390. The ECG TRIG OUT signal is output from the sample and hold circuit on line 2400 and input to the ECG SYNC IN/OUT port for transmission to the external ECG device.

The amplified output of D/A convertor 2310 is also input to comparator 2412. The other input to the comparator is the $V_{BATT}$ signal from the battery. The comparator determines if the proper battery voltage is present. The output of the comparator 2412 is input to line driver 2408.

The other input to driver 2408 is the output of comparator 2404. The inputs to this comparator are ECG TRIG IN signal received from an external device and the ECG TRIG IN signal after processing by peak detector 2401. When the ECG SYNC IN/OUT port is used as an input port, the ECG TRIG IN signal is on line 2400. This signal is input to peak detector 2401 and follower 2403. The output of follower 2403, on line 2405, is the same as the input signal plus a delay. The peak detector detects the peak of the ECG TRIG IN signal and divides the peak signal in half. This signal is output from the peak detector on line 2407 and input to comparator 2404.

Comparator 2404 compares these two valves so that the R-wave in the ECG TRIG IN signal can be detected. The output of comparator is input to the data input to line driver 2408.

When the line driver is enabled by the A/D SEL signal on line 1424, the signals input to the line driver are placed on the D0 and D7 bits of the data bus on line 1414.

Figure 12A:
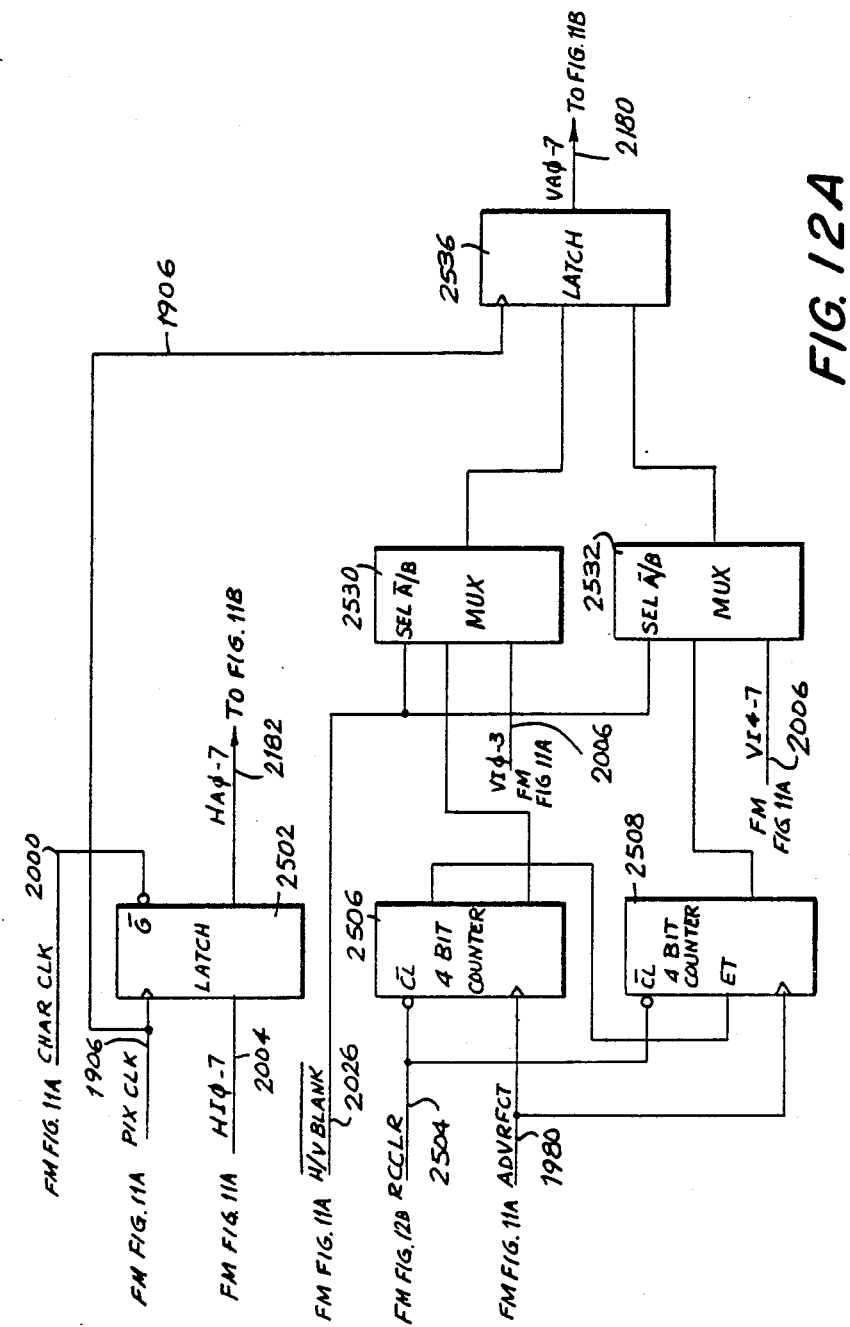
FIGS. 12A-12C comprise a schematic diagram of the scroll/pixel gate array of the pixel circuitry shown in FIG. 11B.
Figure 12B:
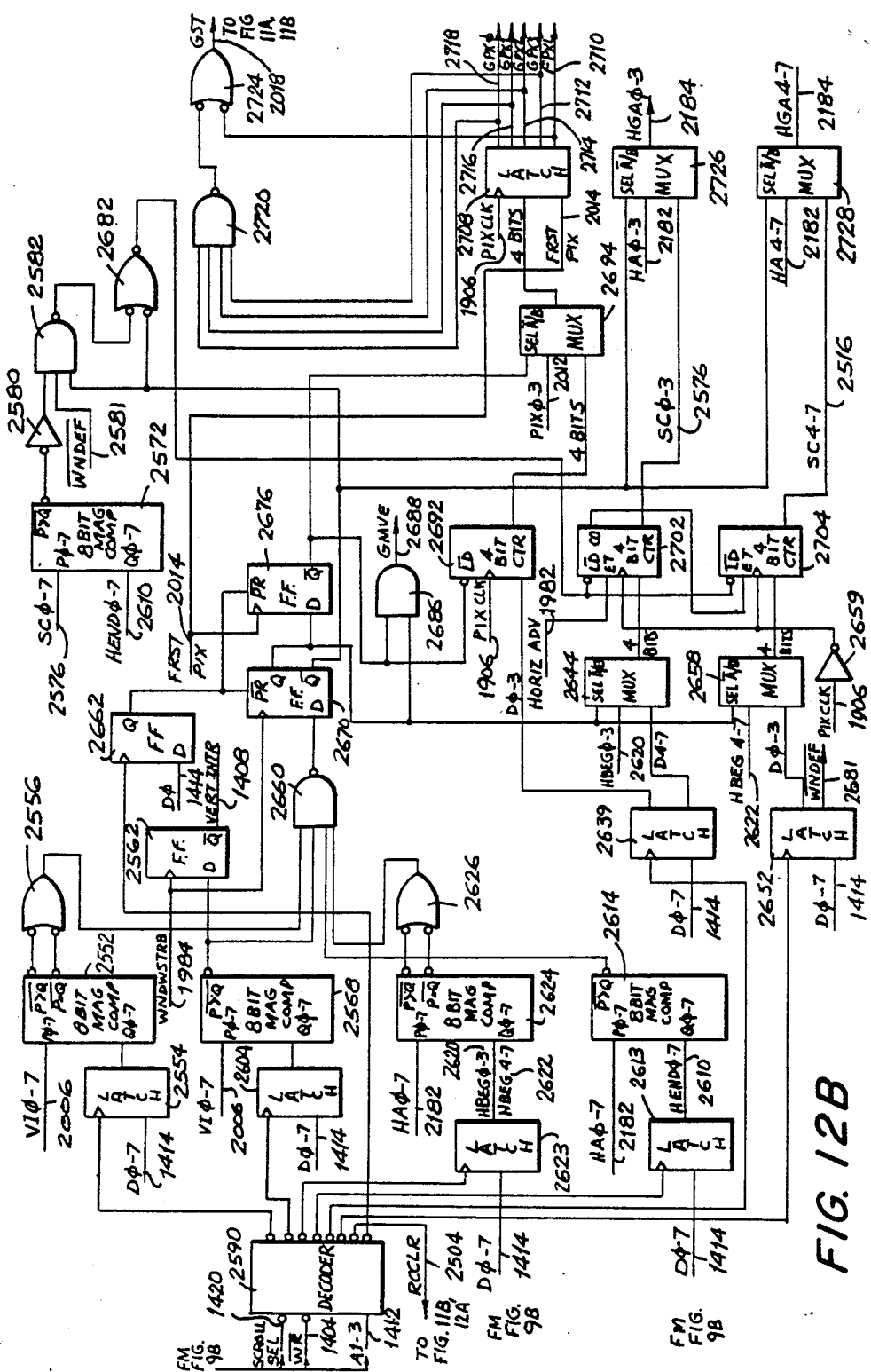
Figure 12C:
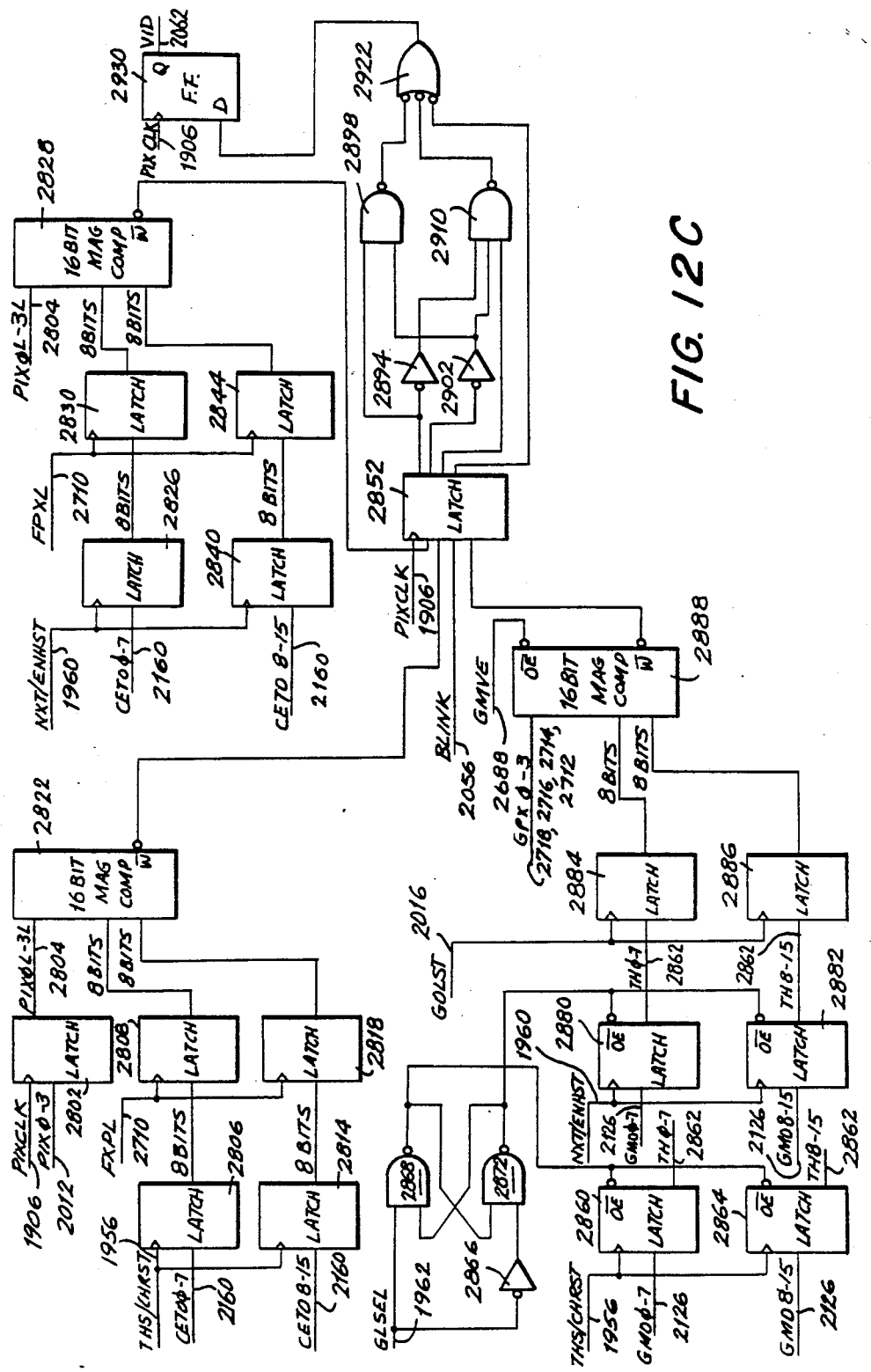

FIGS. 12A, 12B and 12C show scroll/pixel gate array 2190 shown in FIG. 11B.

Referring to FIG. 12A, generation of the horizontal and the vertical address bits is now described.

The parallel 8-bit signal HI0-7 on line 2004 is input to the data inputs of latch 2502. The latch is enabled by the CHAR CLK signal on line 2000. The latch is clocked by the PIX CLK signal on line 1906. When the latch is enabled and clocked, the output is the parallel 8-bit signal HA0-7 (horizontal address bits) on line 2182.

The ADVRFCT signal on line 1980 is input to the clock inputs of 4-bit counters 2506 and 2508. 4-bit counter 2506 will count out, then its terminal count will start 4-bit counter 2508.

The 4-bit output of counter 2506 is input to multiplexer 2530. Also input to this multiplexer are the parallel 4-bit vertical addresses VI0-3 on line 2006. Similarly, the 4-bit output of counter 2508 and the parallel 4-bit vertical addresses VI4-7 on line 2006 are input to multiplexer 2530.

The selection of the 4-bit counter input or the VI0-3 input as the output of multiplexer 2530 is determined by the state of the H/V BLANK bar signal on line 2026. In like manner, whether the 4-bit counter input or the VI4-7 input is selected as output of multiplexer 2532 is determined by the state of the H/V BLANK bar signal.

The RCCLR signal on line 2504 is input to counters 2506 and 2508. This signal clears the counters.

The outputs of multiplexers 2530 and 2532 are input to latch 2536. When this latch is clocked by the PIX CLK signal, the latched values are output as the VA0-7 (vertical address bits) signals on line 2180.

Referring to FIG. 12B, the generation of the HGA-0-7, the GST, and the VERT INTR signals will be described.

The SCROLL SEL signal on line 1420 and the WR bar signal on line 1404 are the enabling inputs to decoder 2590. Address bits A1-3 input on line 1412 control the output from decoder 2590.

One output of decoder 2590 is the RCCLR signal on 2504. This is used in FIG. 12A to clear counters 2506 and 2508.

The first input to NAND gate 2660 is the output of the OR gate 2556. The inputs to this gate are the outputs of 8-bit magnitude comparator 2552.

The first input to comparator 2552 is the parallel 8-bit signal VI0-7 on line 2006. This signal is input to the P data inputs of 8-bit magnitude comparator 2552. The parallel 8-bit signal D0-7 from the data bus on line 1414 is input to latch 2554. This latch is clocked by an output of decoder 2590. When clocked, the D0-7 signal are input to the Q data inputs of 8-bit magnitude comparator 2552.

The output of the comparator is based on satisfying the conditions P>Q bar or P=Q bar. These outputs are input to OR gate 2556. The output of this OR gate is input to NAND gate 2660.

The second input to NAND gate 2660 is the output of 8-bit magnitude comparator 2568. The output of this comparator is determined as follows:

The parallel 8-bit signal D0-7 from the data bus is input to latch 2604. The second output of decoder 2590 clocks latch 2604. When clocked, the 8-bit output of latch 2604 is input to the Q data inputs of 8-bit magnitude comparator 2568.

The parallel 8-bit signal VI0-7 on line 2006 is input to the P data inputs of comparator 2568. The output of this comparator is conditioned on satisfaction of P>Q bar. When this condition is satisfied, the signal output from the comparator changes state and is input to NAND gate 2660.

The third input to NAND gate 2660 is the output of 8-bit magnitude comparator 2614. The output of this comparator is determined as follows:

The parallel 8-bit signal HA0-7 on line 2182 is input to the P data inputs of 8-bit magnitude comparator 2614. The parallel 8-bit signal D0-7 from the data bus is input to latch 2613. The latch is clocked by the fourth output of decoder 2590. When clocked, the parallel 8-bit output of latch 2613 is input to the Q data inputs of comparator 2614. The 8-bit output of latch 2613 on line 2610 is also termed HEND0-7 (horizontal end of the graphic plane window address).

The output of 8-bit magnitude comparator 2614 is determined by satisfaction of the condition P>Q bar.

When this condition is satisfied, the state of the output changes. The output of comparator 2614 is input to NAND gate 2660.

The fourth input to NAND gate 2660 is the output of OR gate 2626. The inputs to the gate are the outputs of 8-bit magnitude comparator 2624. The states of the comparator's outputs are determined as follows:

The parallel 8-bit signal HA0-7 on line 2182 is input to the P data inputs of comparator 2624. The parallel 8-bit signal D0-7 from the data bus is input to latch 2623. This latch is clocked by a third output of decoder 2590. When the latch is clocked, the parallel 8-bit output is input to the Q data inputs of comparator 2624. The outputs of comparator 2624 are conditioned on satisfying P>Q bar or P=Q bar. Satisfaction of these conditions changes the logic states of the outputs. The comparator's outputs are input to OR gate 2626. The output of OR gate 2626 is the fourth input to NAND gate 2660.

The output of latch 2623 is also termed HBEG0-7 (horizontal beginning of the graphic plane window address). The parallel 4-bit signal HBEG0-3 is on line 2620 and the parallel 4-bit signal HBEG4-7 is on line 2622.

The output of 8-bit magnitude comparator 2568 is also input to the data input of flip flop 2562. This flip flop is clocked by the WNDWSTRB signal of line 1984.

The Q bar output of flip flop 2562 is the VERT INTR signal on line 1408. The VERT INTR signal is input to display processor 1702 (FIG. 10).

The output of NAND gate 2660 is input to flip flop 2670. This flip flop is clocked by the WNDWSTRB signal on line 1984. The preset input to flip flop 2670 is controlled by the Q output of flip flop 2662. The data input to flip flop 2662 is the D0 signal on line 1414. The clock input is the SSEL-7 output from decoder 2590.

The Q output of flip flop 2670 is input to the selection inputs of multiplexers 2644 and 2658. The Q bar output is input to the selection inputs of multiplexers 2726 and 2728. The Q bar output is also input to NAND gate 2582.

The Q output of flip flop 2670 is input to the data input of flip flop 2676 and to AND gate 2686. Flip flop 2676 is clocked by the FRST PX signal on line 2014. The preset input to the flip flop is connected to the Q output of flip flop 2662.

When flip flop 2676 is clocked, its Q bar output is input to AND gate 2686. This signal also enables 4-bit counter 2692 and is input to the selection input of multiplexer 2694.

Having described each input to AND gate 2686, the output of this gate is the GMVE (graphic memory video enable) signal on line 2688. This signal causes blanking of the memory at the end of the graphic plane window.

The inputs to 4-bit counter 2692 will now be described.

The parallel 8-bit signal D0-7 on line 1414 is input to latch 2639. This latch is clocked by an output of decoder 2590. When clocked, the first 4-bits are input to 4-bit counter 2692. The remaining 4-bits are input to multiplexer 2644.

The PIX CLK signal on line 1906 is input to the clock input of 4-bit counter 2692. The parallel 4-bit output of counter 2692 is input to multiplexer 2694. The other input to multiplexer 2694 is the parallel 4-bit signal PIX0-3 on line 2012. Based on the control input to this multiplexer, either the parallel 4-bit PIX0-3 signal or the parallel 4-bit output of 4-bit counter 2692 is selected for output to latch 2708. The last input to latch 2708 is the FRST PX signal on line 2014.

When latch 2708 is clocked by the PIX CLK signal on line 1906, the output is the GPX0 signal on line 2718, the GPX1 signal on line 2716, the GPX2 signal on line 2714 and the GPX3 signal on line 2712. These signals are the graphic plane pixel select lines.

The final output of latch 2708 is the FPXL signal on line 2710. This signal is for latching the first pixel word.

The GPX0-3 signals are input to NAND gate 2720. The output of NAND gate 2720 is input to OR gate 2724. The second input to that gate is the FPXL signal on line 2710. The output of OR gate 2724 is the GST (graphic plane strobe) signal on line 2018.

4-bits of the output of latch 2639 are input to multiplexer 2644. The other parallel 4-bit signal input to multiplexer 2644 is the HBEG0-3 signal on line 2620. The output selection input to multiplexer 2644 is the Q output of flip flop 2670.

The output of multiplexer 2644 is input to 4-bit counter 2702. This counter is enabled by the output of NOR gate 2682. The inputs to the NOR gate are as follows:

A first input is the Q bar output of flip flop 2670.

With respect to the second input, the parallel 8-bit signal SC0-7 on line 2576 is input to the P data inputs of 8-bit magnitude comparator 2572. The parallel 8-bit signal HEND0-7 is input to the Q data inputs of the comparator. The output of the comparator is conditioned on the satisfaction of P>Q bar. The satisfaction of this condition changes the signal's logic state.

The output of 8-bit magnitude comparator 2572 is input to inverter 2580. The inverter's output is input to NAND gate 2582. The second input to this gate is the WNDEF bar signal on line 2581. The WNDEF bar signal determines if the current window available for scrolling is scrolled or not.

The third input to NAND gate 2582 is the Q bar output of the flip flop 2670. The output of NAND gate 2582 is the second input to NOR gate 2682.

Once enabled by the output of NOR gate 2682, 4 bit counter 2702 is clocked by the PIX CLK signal on line 1906. This signal is inverted by inverter 2659. As such, counter 2702 is clocked one half clock pulse after other components clocked by the PIX CLK signal.

The parallel 4-bit output of 4 bit counter 2702 is input to multiplexer 2726. The output is also the parallel 4-bit signal SC0-3 on line 2576. These are used as the graphic plane count bits for the scrolled areas.

The other input to multiplexer 2726 is the parallel 4 bit signal HA0-3 on line 2182. Based on the state of the Q bar output of flip flop 2670, one of the 4-bit inputs is output as the HGA0-3 signal. These are 4 bits of the 8-bits of the horizontal graphic plane address.

The parallel 8-bit signal D0-7 on line 1414 is input to latch 2652. The latch is clocked by an output of decoder 2590. When clocked, the first 4-bits are input to multiplexer 2658. The other 4-bit input to multiplexer 2658 is the parallel 4-bit signal HBEG4-7 on line 2622. According to the state of the Q output of flip flop 2670, one of the 4-bit inputs is selected and output from the multiplexer.

The output of multiplexer 2658 is input to 4 bit counter 2704. The terminal count of 4 bit counter 2702 starts counter 2704. The output of NOR gate 2682 enables 4-bit counter 2704.

The HORIZ ADV signal is input to the enable trickle input of counter 2702 for controlling the count.

The output of 4-bit counter 2704 is input to multiplexer 2728. This output is also the 4 bit SC4-7 signal (on line 2576). These are the remaining horizontal graphic plane count bits for the scroll areas.

The second input to multiplexer 2728 is the parallel 4-bit signal HA4-7 on line 2182. Based on the state of the Q bar output of flip flop 2670, one of the 4-bit inputs is output as the HGA4-7 signal on line 2184.

FIG. 12C shows generation of the VID signal on line 2062. The VID signal controls the information on the display screen.

With respect to the character plane, the parallel 4-bit signal PIX∅-3 on line 2012 is input to latch 2802. This latch is clocked by the PIX CLK signal on line 1906. When clocked, the parallel 4-bit output is input to the control inputs of the 16-bit data selector 2822. The signals output by latch 2802 are also termed the PIX∅ L-3L signals on line 2804.

The data inputs to 16-bit data selector 2822 are the CETO∅-15 signals on line 2160 after being latched twice.

The CETO∅-7 signals on line 2160 are input to latch 2806 and the CET08-15 signals on line 2160 are input to latch 2814. Both latches are clocked by the THS/CHRST signal on line 1956. The output of latch 2806 is input to latch 2808 and the output of latch 2814 is input to latch 2818. Latches 2808 and 2818 are clocked by the FPXL signal on line 2710. When clocked, the outputs of these latches are input to the sixteen data inputs of 16-bit data selector 2822. Based on the states of the PIX∅L-3L signals, an output is selected. The selected output is input to latch 2852.

With respect to the enhancement plane, the CETO-∅-7 signals are input to 16-bit data selector 2848 after first being latched by latches 2826 and 2830. Similarly, the CET08-15 signals input to 16-bit data selector 2848 are first latched by latch 2840 and then by latch 2844.

The first set of latches, 2826 and 2840, are clocked by the NXT/ENHST signal on line 1960. The second set of latches, 2830 and 2844, are clocked by the FPXL signal on line 2710.

The parallel 4-bit signal PIX∅L-3L on line 2804 is input to the control inputs of data selector 2848. The output of 16 bit data selector 2848 is input to latch 2852.

A third input to latch 2852 is the BLINK signal discussed previously.

The fourth input to latch 2852 is associated with the graphic plane.

The control input to 16 bit data selector 2888 is the 4 bit GPX∅-3 signal on lines 2718, 2716, 2714 and 2712.

The graphic plane data is double latched like the character and the enhancement plane data.

The GMO∅-7 signals on line 2126 are latched first by latch 2860 and then by latch 2884 before input to data selector 2888. The GM08-15 signals on line 2126 are latched first by latch 2864 and then by latch 2886 before input to data selector 2888. The TH∅-15 signals (on line 2862), shown at the outputs of latches 2860 and 2864, are signal designations to show the connection of the first set of latches to the input lines the latches 2884 and 2886 when this first set of latch is clocked by the THS/CHRST signal on line 1956.

The second set of latches, 2884 and 2886 are clocked by the GOLST signal on line 2016. When the second set of latches are clocked, their data is input to the 16-data inputs of 16 bit data selector 2888.

In a second instance, the GMO∅-7 signal are latched first by latch 2880 and then latch 2884. The GM08-15 signals are first latched by latch 2882 and then latch 2886.

In this case, the first sets of latches, 2880 and 2882, are clocked by the NXT/CHRST signal on line 1960. The second set of latches, 2884 and 2886, are clocked by the GOLST signal on line 2016.

The two first sets of latches, namely 2860 and 2864, and 2880 and 2882, are output enabled by an asynchronous flip flop consisting of NAND gates 2868 and 2872, and inverter 2866. One output of the flip flop connects to the output enable inputs of latches 2860 and 2864. The other output of the flip flop connects to the output enable inputs of latches 2880 and 2882. The GLSEL is input to the flip flop on line 1962. The state of the GLSEL signal determines which first set of latches is output enabled.

Once the data is input to 16-bit data selector 2888, the output of the data selector is enabled by the GMVE signal on line 2688. When enabled, the selected output is input to latch 2852.

The PIX CLK signal on line 1906 clocks latch 2852. The outputs of latch 2852 are input to a series of logic gates. These gates are inverters 894 and 2902, NAND gates 2898 and 2910, and NOR gate 2922. Processing of the outputs of latch 2852 by these gates is known by one skilled in the art without further explanation.

The output of NOR gate 2922 is input to the data input of flip flop 2930. The PIX CLK signal on line 1906 clocks flip flop 2930. When clocked, the Q output is the VID signal on line 2062.

Figure 13:
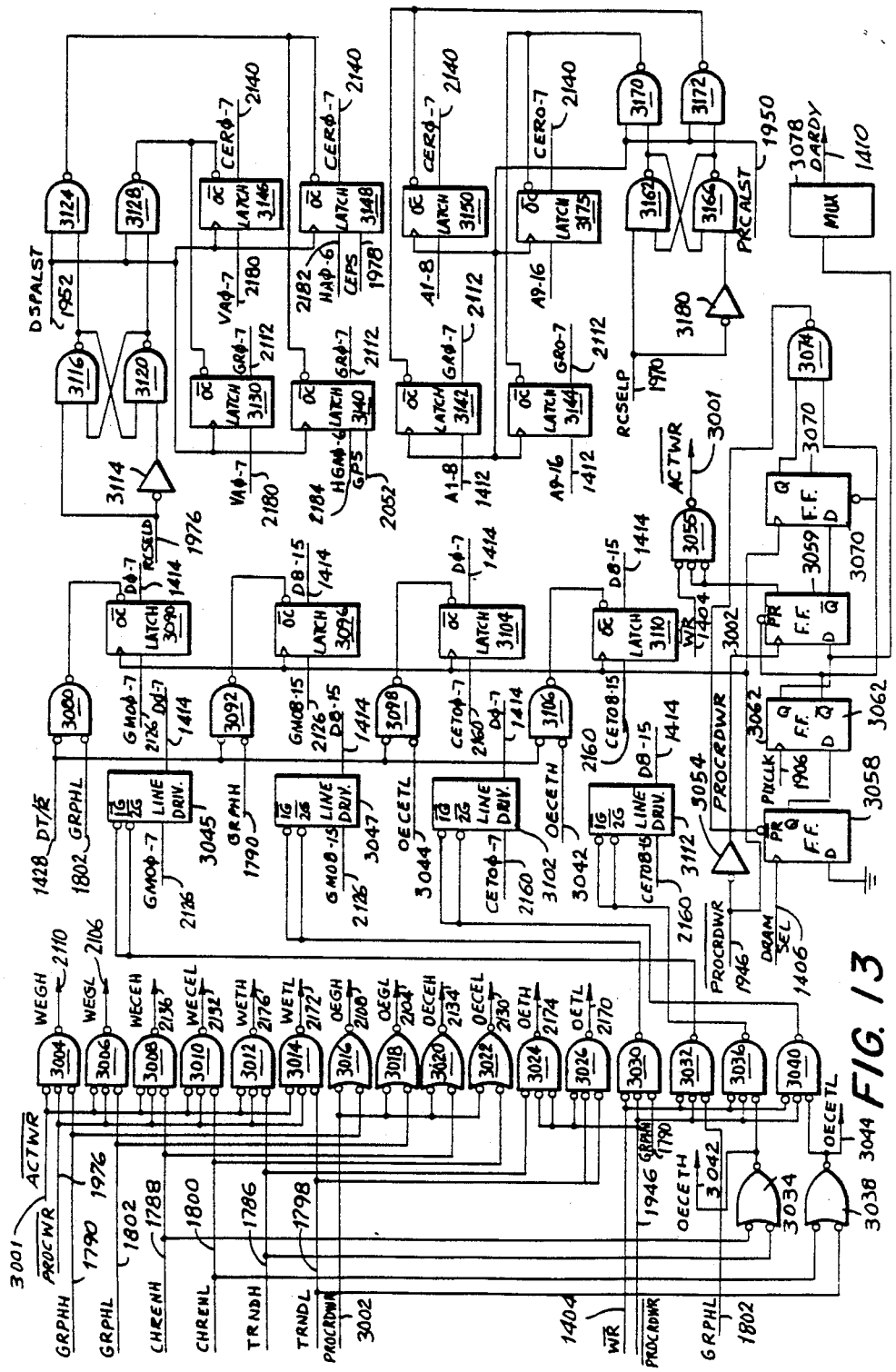
FIG. 13 is a schematic diagram of the CRT memory control gate array of the pixel circuitry shown in FIG. 11B.

FIG. 13 shows the CRT memory control gate array.

The DRAM SEL signal in line 1406 clocks flip flop 3058. The Q output of flip flop 3058 is the data input of flip flop 3062 which is clocked by the PIX CLK signal on line 1906.

The Q output of flip flop 3062 is input to the data input of flip flop 3059. This output is also input to the data input of multiplexer 3078. This multiplexer's output is the DARDY signal on line 1410.

The Q bar output of flip flop 3062 is input to the preset input of flip flop 3059, to NAND gate 3074 and to the clear bar input of flip flop 3070. The clock input to flip flop 3059 is the PROCRDWR signal on line 3002.

The Q output of flip flop 3059 is tied to two inputs of NAND gate 3055. The other input to NAND gate 3055 is the WR bar signal on line 1404. The output of NAND gate 3055 is the ACTWR bar signal on line 3001. The ACTWR bar signal indicates that the microprocessor is actively writing into a DRAM.

The Q bar output of flip flop 3059 is input to the data input of flip flop 3070. The PROCRDWR bar signal on line 1946 clocks flip flop 3070. The Q output of flip flop 300 is the second input to NAND gate 3074. The output of NAND gate 3074 is input to the preset input of the flip flop 3058.

Generation of the high and low output enable and write enable signals for the graphic plane, character/enhancement plane and trend section will be described.

Referring to FIG. 13, the write enable signals for the graphic plane, character/enhancement plane and trend section are determined by the outputs of NAND gates 3004, 3006, 3008, 3010, 3012 and 3014. Two inputs to each gate are the same. These inputs are the ACTWR bar signal on line 3001 and the PROCWR bar signal on line 1976. The third signal input to a particular NAND gate is one of the six signals generated by the display processor for use in determining the selection of the graphic plane high or low, character/enhancement plane high or low, and trend section high or low.

The GRPHH signal on line 1790 is the third input to NAND gate 3004, whose output is the signal WEGH on line 2110. The GRPHL signal on line 1802 is the third input to NAND gate 3006, whose output is the WEGL signal on line 2106. The CHRENH signal on line 1788 is the third input to NAND gate 3008, whose output is the WECEH signal on line 2136. The CHRENL signal on line 1800 is the third input to NAND gate 3010, whose output is the WECEL signal on line 2132. The TRNDH signal on line 1786 is the third input to NAND gate 3012, whose output is the WETH signal on line 2176. The TRNDL signal on line 1798 is the third input to NAND gate 3014, whose output is the WETL signal on line 2172.

The first input to NOR gates 3016, 3018, 3020 and 3022 is the PROCRDWR signal on line 3002. The second input to NOR gate 3016 is the GRPHH signal. The output of NOR gate 3016 is the OEGH signal on line 2108. The second input to NOR gate 3018 is the GRPHL signal. The output of NOR gate 3018 is the OEGL signal on line 2104. The second input to NOR gate 3020 is the CHRENH signal. The output of NOR gate 3020 is the OECEH signal on line 2134. The second input to NOR gate 3022 is the CHRENL signal. The output of NOR gate 3022 is the OECEL signal on line 2130.

The first two inputs to NAND gate 3024 are the PROCRDWR bar signal on line 1946 tied to two inputs. The third input is the TRNDH signal on line 1786. The first input to NAND gate 3026 is the PROCRDWR bar signal on line 1946. The second and third inputs are the TRNDL signal on line 1798 tied to two inputs.

The output of NAND gate 3024 is the OETH signal on line 2174. The output of NAND gate 3026 is the OETL signal on line 2170.

The inputs to NOR gate 3034, are the CHRENH signal on line 1788 and the TRNDH signal on line 1786. The output of NOR gate 3034 is the OECETH signal on line 3042.

The inputs to NOR gate 3038 are the CHRENL signal on line 1800 and the TRNDL signal on line 1798. The output of NOR gate 3038 is the OECETL signal on line 3044.

Bus buffers 3045 and 3047 are for transferring data from the data bus, D∅-15, to the graphic plane memory outputs, GMO∅-15. The low order bits are handled by bus buffer 3045 and the high order bits are handled by bus buffer 3047. In like manner, bus buffers 3102 and 3112 are for transferring data from the data bus, D∅-15, to the character/enhancement/trend memory outputs, CETO∅-15. The low order bits are handled by bus buffer 3102. The high order bits are handled by bus buffer 3112.

The signal enabling bus buffer 3045 is the output of NAND gate 3032. The inputs to NAND gate 3032 are the WR bar signal on line 1404, the PROCRDWR bar signal on line 1946 and the GRPHL signal on line 1802.

The signal enabling bus buffer 3047 is the output of NAND gate 3030. The inputs to this gate are the WR bar signal on line 1404, the PROCRDWR bar signal on line 1946, and the GRPHH signal on line 1790.

The signal enabling bus buffer 3102 is the output of NAND gate 3040. The inputs for the NAND gate 3040 are the WR bar signal on line 1404, the PROCRDWR bar signal on line 1946 and the OECETL signal on line 3044.

The signal enabling bus buffer 3112 is the output of NAND gate 3036. This gate's inputs are the WR bar signal on line 1404, PROCRDWR bar signal on line 1946 and the OECETH signal on line 3042.

Latches 3090 and 3096 are to transfer data from the graphic plane memory outputs to the data bus. Latches 3104 and 3110 are to transfer data from the character/enhancement/trend memory outputs to the data bus. All four latches are clocked by the PROCRDWR bar signal on line 1946. However, each of the four latches are output enabled by a different NAND gate. One input to the four NAND gates is the DT/R (R bar) signal on line 1428. The second signal input to each gate will now be described.

NAND gate 3080 output enables latch 3090. This latch transfers data from the low order bits of the graphic plane memory outputs, GMO∅-7, to the low order bits of the data bus, D∅-7. The second signal input to NAND gate 3090 is the GRPHL signal on line 1802.

NAND gate 3092 output enables latch 3096. The latch transfers data from the high order bits of the graphic plane memory outputs, GM08-15, to the high order bits of the data bus, D8-5. The second signal input to NAND gate 3096 is the GRPHH signal on line 1790.

NAND gate 3098 output enables latch 3104. Latch 3104 transfers data from the low order bits of the character/enhancement/trend memory outputs, CETO∅-7, to the low order bits of the data bus, D∅-7. The second input to NAND gate 3098 is the OECETL signal on line 3044.

NAND gate 3106 output enables latch 3110. Latch 3110 transfers data from the high order bits of the character/enhancement/trend memory outputs, CETO-8-15, to the high order bits of the data bus, D8-15. The second input to NAND gate 3106 is the OECETH signal on line 3042.

Latch 3130 transfers the vertical address information in the VA∅-7 signals to the graphic plane addresses, GR∅-7. Latch 3146 transfers the vertical address information in the VA∅-7 signals to the character/enhancement plane addresses, CER∅-7.

Latch 3140 transfers the horizontal address information in the HGA∅-6 signals and the GPS signal to the graphic plane addresses, GR∅-7. Latch 3148 transfers the horizontal address information in the HA∅-6 signals and the CEPS signal to the character/enhancement plane addresses, CER∅-7.

The signal that clocks latches 3130, 3140, 3146 and 3148 is the DSPALST signal on line 1952.

Enablement of these four latches is determined by an asynchronous flip flop comprising NAND gates 3116 and 3120, and inverter 3114. The output of NAND gate 3116 of the flip flop is input to NAND gate 3124. The output of NAND gate 3120 of the flop flop is input to NAND gate 3128. The second input to NAND gates 3124 and 3128 is the DSPALST signal on line 1952.

The output of NAND gate 3124 is input to the output enable inputs of latches 3140 and 3148 (for the horizontal addresses). The output of NAND gate 3128 is input to the output enable inputs of latches 3130 and 3146 (for the vertical addresses).

The RCSELD signal on line 1972 is input to the flip flop. When the DSPALST signal has the proper state, the state of the RCSELD signal determines whether row or column address information is transferred.

Latch 3142 transfers the row address information in the A1-8 signals to the graphic plane addresses, GR0-7. Latch 3150 transfers the row address information in the A1-8 signals to the character/enhancement plane addresses, CER0-7.

Latch 3144 transfers the column address information in the A9-16 signals to the graphic plane addresses, GR0-7. Latch 3175 transfers the column address information in the A9-16 signals to the character/enhancement plane addresses, CER0-7.

The signal that clocks latches 3142, 3144, 3150 and 3175 is the PRCALST signal on line 1950.

Enablement of the four latches is determined by an asynchronous flip flop comprising NAND gates 3162 and 3166, and inverter 3180. The output of NAND gate 3162 of the flip flop is input to NAND gate 3170. The output of NAND gate 3166 of the flip flop is input to NAND gate 3172. The second input to NAND gates 3170 and 3172 is the PRCALST signal on line 1950.

The output of NAND gate 3170 is input to the output enable inputs of latches 3144 and 3175 (for the column addresses). The output of NAND gate 3172 is input to the output enable inputs of latches 3142 and 3150 (for the row addresses).

The RCSELP signal is input to the flip flop on line 1970. When the PRCALST signal has the proper state, the state of the RCSELP signal determines whether row or column address information is transferred.

FIG. 14 shows the digital output board 140 (FIG. 1). The TxD signal on line 1510, the RxD signal on line 1512, the DTR signal on line 1514, the DSR signal on line 1516, the RTS signal on line 1518 and the CTS signal on line 1520 are for communications between controller 1776 (FIG. 10A) and an external device connected to digital connector 3302.

The optional digital output connector 3304 is also shown in FIG. 14. The RD bar signal on line 1402, the WR bar signal on line 1404, the parallel 8 bit data bus signal D0-7 on line 1414, the DT/R (R bar) signal on line 1428, the parallel 3 bit address bus A1-3 on line 1412, the SLAVE SEL signal on line 1504, the SLAVE INTR signal on line 1506 and the CLK OUT signal on line 1508 are for communications with and control of an external device by the microprocessor 1702 (FIG. 10A).

Referring to FIG. 15, the knob board 144 and five button panel 148 for control of the system of the present invention are shown.

Manual movement of knob 3410 changes the output to flip flops 3416 and 3426. The knob output to flip flop 3416 is processed by Schmitt trigger 3414 before input. The knob output to flip flop 3426 is processed by Schmitt trigger 3424 before input.

Flip flops 3416 and 3426 are clocked by the output of NAND gate 3417. When flip flop 3416 is clocked, the Q output is input to the data input of flip flop 3420. The output of flip flop 3416 is also one of the inputs to exclusive OR gate 3438.

When flip flop 3426 is clocked, the Q bar output is input to the data input of flip flop 3430. The Q bar output is also input to exclusive OR gates 3436 and 3440.

Flip flops 3420 and 3430 ar clocked by the output of NAND gate 3417. When these flip flops are clocked, the Q bar output of flip flop 3430 is the second input to exclusive OR gate 3440 and the Q bar output of flip flop 3420 is the second input to exclusive OR gates 3436 and 3438.

The outputs of exclusive OR gates 3438 and 3440 are input to exclusive OR gate 3446.

The output of exclusive OR gate 3446 is input to buffer 3204. The output of exclusive OR gate 3436 is also input to buffer 3204. Another data input to buffer 3204 is the Q bar output of flip flop 3403. The Q bar output is tied to four inputs of buffer 3204. The D0 signal on line 1414 from the data bus is input to the data input of the flip flop.

Flip flop 3403 is clocked by the output of NAND gate 3415. The inputs to this NAND gate are the WR bar signal on line 1404 and the DISP SEL signal on line 1602.

The output of NAND gate 3417 also enables buffer 3204. The inputs to NAND gate 3417 are the RD bar signal on line 1402 and the DISP SEL signal on line 1602.

When the buffer is enabled, the outputs from exclusive OR gates 3436 and 3446 are placed on the data bus, D8 and D9. The output from flip flop 3403 is input to alarm circuitry 3408 and used to drive selected alarms.

The output of NAND gate 3417 is also the output enable input to buffer 3484. The data inputs to buffer 3484 are the output of alarm switch 3452, the output of ON/STBY switch 3456 through isolation diode 3455, the output of HELP switch 3460 and the outputs of BUTTONS 1-5, shown at 3464, 3468, 3472, 3476 and 3480, respectively. The buttons and switches are the operator interface for system operation and control. When the buffer is enabled, the values of above-described inputs are placed on the data bus for transmission to microprocessor 1702.

Referring to FIG. 1, the system powering the improved gas analyzer system is power supply 158, rectifier 160 and DC-DC converter 162. It is a split system with a first half powering the display section and the second half powering the analog section. Each half of the system has its own battery backup. This system is conventional and known to those skilled in the art.

Figure 16:
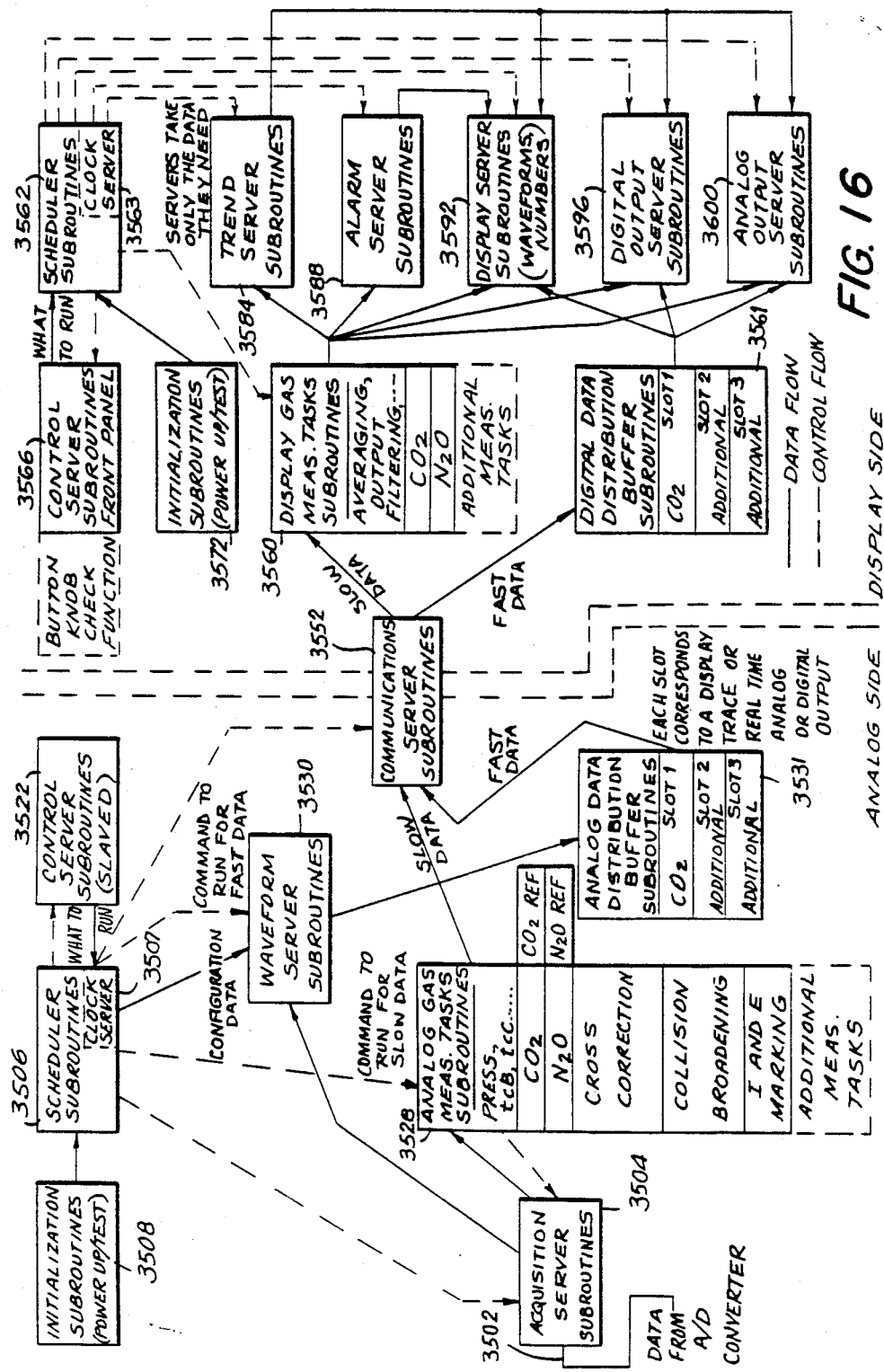
FIG. 16 is a block diagram of the software for controlling the multichannel gas analyzer system of the present invention.

FIG. 16 shows a block diagram of the software modules for the display and analog processors. The software program listing, is divided into seven sections: MAIN, ACQ, AOUT, AMENU, ALARM, COMM, DISPLAY, GAS, HISTORY, MENU, MENU2, POUT, SYS, and WF. The software program listing is available in the Application file and not in the patent. Further, all reference herein to specific sections and pages of a software program listing are to portions of that software program listing. The modules will be described and the areas of the software program that correspond to a particular module will be indicated. An example of a code citation for identifying the location of a specific module is as follows: MAIN pp. 29-40. In FIG. 16, the solid lines indicate data flow and the dashed lines indicate control flow.

The Initialization subroutines for both the display side and analog side power up the system and carry out initial start functions and tests. Analog Initialization subroutines 3508 are found at MAIN pp. 1-14. Display Initialization subroutines 3572 are located at MAIN pp. 5-29.

The master Control Server is display Control Server 3566. Analog Control Server 3522 is slaved to master Control Server 3566. The Control Servers control overall system operations. The subroutines of display Control Server 3566 monitor the buttons, knobs and switches of the control panel and appropriately adjust system operations based on their positions. Both the analog and display Control Servers provide data to their respective Scheduler subroutines 3506 and 3562 on "WHAT TO RUN". Analog Control Server subroutines 3522 are found at AMENU pp. 1-43. Display Control Server subroutines 3566 are found at MENU pp. 1-277, and MENU2 pp. 1-156.

Analog Scheduler 3506 and display Scheduler 3562 manage the processes and events for their respective sides. The Schedulers insure the programmed functions for each side are carried out. Analog Scheduler subroutines 3506 are located in the code at SYS pp. 81-104. Display Scheduler subroutines 3562 are also located at SYS pp. 81-104.

The Scheduler subroutines for both the analog and display side also include Clock Server subroutines. The Clock Server subroutines manage system timing of all events. Analog Clock Server subroutines 3507 are found at SYS pp. 7-18. Display Clock Server subroutines 3563 are also found at SYS pp. 7-18.

Acquisition Server 3504 accesses the raw data from the A/D converter. It provides this data to Analog Measurement Tasks (AMT) subroutines 3528 to produce numerical output values. It also provides this data to Waveform Server subroutines 3530 to produce waveforms. Acquisition Server subroutines 3504 are found at ACQ pp. 1-127.

Waveform Server 3530 is the programming for transforming raw data into waveform data. The Waveform Server subroutines acquire data from Acquisition Server subroutines 3504, process it and transfer the data to Communications Server subroutines 3552 that links the analog and display sides. Waveform Server subroutines 3530 are found at WF pp. 1-26.

Analog Measurement Tasks (AMT) 3528 transform from the raw data to usable information for display and output purposes. AMT subroutines 3528 are found at GAS pp. 1-133.

Display Measurement Tasks (DMT) 3560 carry out data distribution to Trend Server subroutines 3584, Alarm Server subroutines 3588, Display Server subroutines 3592, Digital Output Server subroutines 3596, and Analog Output Server subroutines 3600. The DMT subroutines are found at GAS pp. 134-165.

Analog Data Distribution Buffer (ADDB) 3531 and Display Data Distribution Buffer (DDDB) 3561 serve as common locations for access to fast data. ADDB structures 3531 are found at COMM pp. 1-92. DDDB structures are also found at COMM pp. 1-92.

Communications Server 3552 communicates data between the analog and the display sides. These subroutines are found out at COMM pp. 1-92.

Display Server 3592 links to DMT subroutines 3560 and DDDB structures 3561. The Display Server subroutines receive the data from the DMT subroutines and the DDDB structures, and process the data for numerical and graphical display. The Display Server subroutines can be found at DISPLAY pp. 1-360.

Trend Server 3584 stores historical data from the DMT subroutines and provides it to Display Server subroutines 3592, Digital Output Server subroutines 3596 and Analog Output Server subroutines 3600 when ordered by Control Server subroutines 3562 via Scheduler subroutines 3562. Trend Server subroutines 3584 can be found in the code at HISTORY pp. 1-22.

Alarm Server 3588 links to the DMT subroutines and receives data from those subroutines. For output purposes, the Alarm Server subroutines provide data for both audible and visual alarms to the Display Server subroutines. Alarm Server subroutines 3588 are found at ALARM pp. 1-37.

Digital Output Server 3596 processes the data from DMT subroutines 3560 and DDDB structures 3561 for digital output to external devices. This server's subroutines can be found at COMM pp. 64-81, POUT pp. 1-12, 1A-11A.

Analog Output Server 3600 processes streams of output waveform and value data from the DMT subroutines and DDDB structures 3561 for output to external devices. The subroutines for this server are found AOUT pp. 1-68.

The software operations will now be discussed.

At system start up, Initialization subroutines 3508 and 3572 initialize values for the system and conduct certain tests. In this procedure, data about the system is sent to Scheduler subroutines 3506 and 3562. Initialization subroutines 3508 and 3572 also start the Clock Servers subroutines 3567 and 3563, respectively.

The initialized Analog Scheduler subroutines 3506 are directed what processes to run by the analog Control Server subroutines 3522. Analog Control Server subroutines 3522 determine the system configuration at system start-up and pass this information to the display Control Server subroutines 3566. The display Control Server runs a subroutine for a buttons and knobs check. As the result of the buttons and knobs check, analog Control Server subroutines 3522 determine the AMT subroutines to run and send data to the Analog Scheduler subroutines as to the AMT subroutines to run.

Analog Scheduler subroutines 3506 and AMT subroutines 3528, based on the data from analog Control Server subroutines 3522, provide control information to Acquisition Server subroutines 3504. The Acquisition Server subroutines, when commanded, access the A/D converter data on line 3502. Acquisition Server subroutine 3504 buffers the data until the Analog Scheduler subroutines direct that the data be sent to AMT subroutines 3528 and Waveform Server subroutines 3530. AMT subroutines 3528 and Waveform Server subroutines 3530 transform the data according to their respective programming.

The Analog Scheduler subroutines acknowledge that data is being sent to AMT subroutines 3528 and Waveform Server subroutines 3530. The Analog Scheduler subroutines command the AMT subroutines to run for slow data and command Waveform Server subroutines 3530 to run for fast data.

AMT subroutines 3528 calculate the common equations used by all of the gases; e.g., the flow rate, pressure in the optical bench and temperature in the optical bench. These subroutines also calculate the partial pressure for each gas. Further, these subroutines calculate the position for superimposing the "I" and "E" on the capnogram to indicate the transition points between inspiration/expiration and expiration/inspiration.

The AMT subroutines can have other subroutines which can be commanded to run other types of measurement calculations, e.g., $SaO_2$ measurement tasks (oxygen saturation).

Analog Scheduler subroutines 3506 continuously direct Waveform Server subroutines 3530 to run for fast data. Waveform Server subroutines 3530 send the transformed fast data to ADDB structures 3531. Analog Scheduler subroutines 3506 command Communications Server subroutines 3552 to acquire the fast data in the ADDB structures and transmit it to DDDB structures 3561.

Analog Clock Server subroutines 3507 provide for the timed operation of the AMT subroutines and Waveform Server operations by providing timed suspensions of processes and timed calls to subroutines.

Analog Scheduler subroutines 3506, based on the subroutines of Clock Server subroutines 3507, instruct Communications Server subroutines 3552 to buffer data from Waveform Server subroutines 3530 and AMT subroutines 3528. Communications Server subroutines 3552 buffer data, and when time-out is reached, transfer the data to DMT subroutines 3560 and DDDB structures 3561 on the display side.

Now referring to the display side:

DMT subroutines 3560 receive data from the Communications Server subroutines as commanded by Display Scheduler subroutines 3562 and display Control Server subroutines 3566. The DMT subroutines carry out their required measurement tasks on the slow data.

The data output by DMT subroutines 3560 is input to the five output type servers. Scheduler subroutines 3562 command Trend Server subroutines 3584, Alarm Server subroutines 3588, Display Server subroutines 3592, Digital Output Server subroutines 3596, and Analog Output Server subroutines 3600 to receive specific data according to their programming.

Once the data is received, the respective server subroutines process the the data for output, or in the case of the Trend Server, process the data for historical purposes.

Display Scheduler subroutines 3562 command Display Server subroutines 3592, Digital Output Server subroutines 3596 and Analog Output Server subroutines 3600 to access the fast data in the DDDB structures 3561. After accessing the data, each processes it according to its programming.

Figure 17:
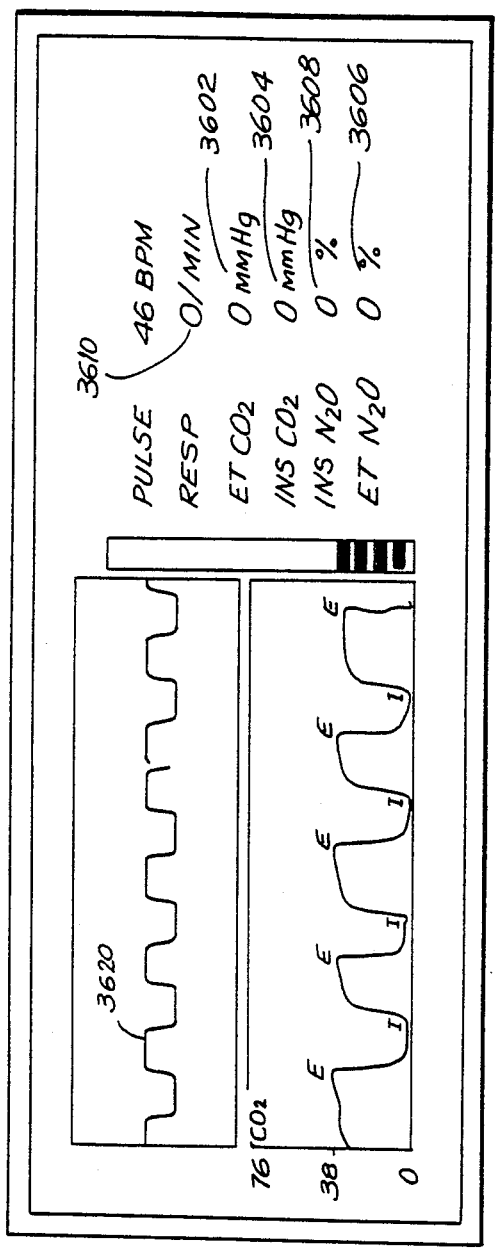
FIG. 17 shows a representative CRT screen display for the multichannel gas analyzer system of the present invention.

FIG. 17 shows a representative screen display of the multichannel gas analyzer system of the invention with respect to gas detection information.

The end-tidal and inspired $CO_2$ in mmHg are shown at 3602 and 3604, respectively; the end-tidal and inspired percent concentration of $N_2O$ are shown at 3606 and 3608, respectively; and the breath rate is shown at 3610.

A $CO_2$ capnogram is shown generally at 3612. Superimposed on the capnogram at the inspiration and expiration transition points are the "I" and "E" markings referred to previously. The positions of the "I" and "E" points are determined by the software based on the measured values for the scrolling $CO_2$ capnogram.

The remainder of the screen display is for other measurements not associated with the respiratory gas stream. Accordingly, the scrolling waveform at 3620 is not a display of gas detection information.

The terms and expressions which are employed here are terms of description and not of limitation. There is no intention, in the use of such terms and expressions, to exclude the equivalents of the features shown and described, or portions thereof, it being recognized that various modifications are possible within the scope of the invention as claimed.

We claim:

1. A gas analyzer system, comprising:
(a) gas sampling means for removing a sample gas stream from a gas source;
(b) an optical bench with means connected to the gas sampling means, the optical bench, further comprising,
 (1) a gas pathway through the optical bench, with the gas pathway having an inlet means for adapting the cross-sectional shape of the sample gas stream being input to the gas pathway to the cross-sectional shape of the gas pathway,
 (2) at least one detection channel assembly disposed along the gas pathway that has an optical path through the gas pathway and reference means for generating reference signals, with the detection channel assembly including an energy source for emitting energy capable of being absorbed at least by a gas of interest in the sample gas stream, filter means for transmitting therethrough energy at wavelengths capable of being absorbed by the gas of interest, detector means capable of generating an output signal in proportion to an amount of energy issuing on the detector means from the filter means, and chopping means for during discrete periods causing energy to issue on the detector means for detecting the absorption by the gas of interest in the sample gas stream,
 (3) timing means for generating cycle timing signals for use in timing detection events and processing of signals generated by the detector means,
 (4) temperature sensing means for measuring the temperature within the optical bench,
 (5) pressure measuring means for measuring the pressure within the gas pathway;
 (6) storage means for storing information for characterizing components of the optical bench, and
 (7) circuitry for processing signals generated by the detector means relative to signals generated by the reference means, the timing means, the temperature sensing means, and the pressure sensing means, and for processing signals from the storage means that are representative of the information for characterizing the optical bench components; and
(c) fluid flow control means including at least a first pump means for drawing the sample gas stream through the gas pathway at a predetermined rate and flow sensing means for measuring flow rate of the sample gas stream through the gas pathway,
(d) analog signal processing circuitry, further comprising,
 (1) analog input circuits for receiving signals output from the optical bench, processing these signals and converting them from analog to digital signals,
 (2) signal processing circuits for receiving the digital outputs from the analog input circuits and correcting the signals indicative of the partial pressure of the gas of interest in the gas pathway for temperature, collision broadening, cross-correction, pressure in the gas pathway, and characterization of the optical bench components, and
 (3) output circuit for providing at least the corrected signals for the partial pressure of the gas of interest in the gas pathway to display processing circuitry; and
(e) display processing circuitry for receiving the digital signals output from the analog signal processing circuitry, processing the signals, and generating signals for controlling the display of information on a display means, for output from the system, and for activation of alarm means when appropriate.

2. The system as recited in claim 1, wherein when the detector means is a lead selenide detector.

3. The system as recited in claim 1, wherein the filter means passes energy having wavelengths in the absorption band of $CO_2$.

4. The system as recited in claim 1, wherein the filter means passes energy having wavelengths in the absorption band of $N_2O$.

5. The system as recited in claim 1, wherein the energy source is an infrared source.

6. The system as recited in claim 1, wherein the pressure sensing means includes an absolute-type pressure sensor.

7. The system as recited in claim 1, wherein the flow sensing means includes a differential-type pressure sensor.

8. The system as recited in claim 1, wherein the flow rate of the sample gas stream through the gas pathway is preferably 50 cc/min.

9. The system as recited in claim 1, wherein the system has a response time of not greater than 100 milliseconds.

10. The system as recited in claim 1, wherein the microprocessor determines the partial pressure of the gas of interest for display according to the expression:

$$PPmmHg\ [X] = \frac{((PP[X])\ (Barometric\ Prs_N))}{SampleCellPrs}$$

where,

X = the gas of interest.

PP[X] = The final partial pressure of the gas of interest corrected for the pressure in the gas pathway, barometric pressure, cross-correction, collision broadening, temperature, and characterization.

Barometric $Prs_N$ = the last measured barometric pressure stored in a memory.

SampleCellPrs = the pressure measured in the sample cell (optical bench) when the gas voltages are measured.

11. The system as recited in claim 1, wherein the optical bench operates over a range of temperatures.

12. The system as recited in claim 1, wherein the inlet means shapes the sample gas stream from a circular cross-section to a rectangular cross-section.

13. The system as recited in claim 12, wherein the flow shaper further includes a filter disposed across the sample gas stream which assists in flow shaping.

14. The system as recited in claim 1, wherein the system further includes a shield means for shielding against background energy ingressing the optical path.

15. The system as recited in claim 14, wherein the shield means further includes a first aperture means disposed adjacent the second window or shielding the optical path against ingress of background energy, a second aperture means spaced way from the first aperture means for shielding the optical path against ingress of background energy, and the chopping means disposed between the first and second apertures means.

16. The system as recited in claim 1, wherein the reference means includes a reference cell containing a fixed amount of gas.

17. The system as recited in claim 16, wherein the detector channel assembly further includes a first window mounted as a portion of a sidewall of each the gas pathway and the reference cell, the energy source mounted behind the first window to provide energy through the first window into the gas pathway and the reference cell and a second window mounted as a portion of the opposing sidewall of each the gas pathway and the reference cell from the first window for passing energy out of the gas pathway and the reference cell.

18. The system as recited in claim 16, wherein the reference cell is disposed adjacent to the gas pathway in the optical path of the detection channel assembly.

19. The system as recited in claim 1, wherein the fluid flow control means further includes a first valve means for controlling the choice of fluid flows through the gas pathway.

20. The system as recited in claim 19, wherein the fluid flow control means further includes a second valve means for backflushing the gas sampling means.

21. The system as recited in claim 20, wherein the flow control means further includes third and fourth valve means capable of redirecting the fluid flow through an external device for measurement of predetermined constituents of a fluid flow, and a fifth valve means which in conjunction with the first valve means, the first pump means and the flow sensing means is used for determining the fluidtight integrity of the gas pathway.

22. An optical bench, comprising:
(a) a gas pathway through the optical bench, with the gas pathway having an inlet means for adapting the cross-sectional shape of a sample gas stream being input to the gas pathway to the cross-sectional shape of the gas pathway,
(b) at least one detection channel assembly disposed along the gas pathway that has an optical path through the gas pathway and reference means for generating reference signals, with the detection channel assembly including an energy source for emitting energy capable of being absorbed at least by a gas of interest in the sample gas stream, filter means for transmitting therethrough energy at wavelengths capable of being absorbed by the gas of interest, detector means capable of generating an output signal in proportion to an amount of energy issuing on the detector means from the filter means, and chopping means for during discrete periods causing energy to issue on the detector means for detecting the absorption by the gas of interest in the sample gas stream;
(c) timing means for generating cycle timing signals for use in timing detection events and processing of signals generated by the detector means;
(d) temperature sensing means for measuring the temperature within the optical bench,
(e) pressure measuring means for measuring the pressure within the gas pathway;
(f) storage means for storing information for characterizing components of the optical bench; and
(g) circuitry for processing signals generated by the detector means relative to signals generated by the reference means, the timing means, the temperature sensing means, and the pressure sensing means, and for processing signals from the storage means that are representative of the information for characterizing the components of the optical bench.

23. The optical bench as recited in claim 22, wherein the detector means is a lead selenide detector.

24. The optical bench as recited in claim 22, wherein the filter means passes energy having wavelengths in the absorption band of $CO_2$.

25. The optical bench as recited in claim 22, wherein the filter means passes energy having wavelengths in the absorption band of $N_2O$.

26. The optical bench as recited in claim 22, wherein the energy source is an infrared source.

27. The optical bench as recited in claim 22, wherein the inlet means shapes the sample gas stream from a circular cross-section to a rectangular cross-section.

28. The optical bench as recited in claim 27, wherein the flow shaper further includes a filter disposed across the sample gas stream which assists in flow shaping.

29. The optical bench recited in claim 22, wherein the optical bench further includes a shield means for shielding against background energy ingressing the optical path.

30. The system as recited in claim 29, wherein the shield means further includes a first aperture means disposed adjacent the second window for shielding the optical path against ingress of background energy a second aperture means spaced away from the first aperture means for shielding the optical path against ingress of background energy and the chopping means disposed between the first and second aperture means.

31. The optical bench as recited in claim 22, wherein the reference means includes a reference cell containing a fixed amount of gas.

32. The optical bench as recited in claim 31, wherein the reference cell is disposed adjacent to the gas pathway in the optical path of the detection channel assembly.

33. The optical bench as recited in claim 31, wherein the detector channel assembly includes comprises a first window mounted as a portion of a sidewall of each the gas pathway and the reference cell, the energy source mounted behind the first window to provide energy through the first window into the gas pathway and the reference cell, a second window mounted as a portion of the opposing sidewall of each the gas pathway and the reference cell from the first window for passing energy out of the gas pathway and the reference cell.

34. The optical bench as recited in claim 33, wherein the pressure sensing means includes an absolute-type pressure sensor.

35. The optical bench of recited in claim 33, wherein the optical bench operates over a range of temperatures.

36. A gas analyzer apparatus, comprising:
(a) an optical bench, further comprising,
  (1) a gas pathway through the optical bench, with the gas pathway having an inlet means for adapting the cross-sectional shape of a sample gas stream being input to the gas pathway to the cross-sectional shape of the gas pathway,
  (2) at least gas one detection channel assembly disposed along the gas pathway that has an optical path through the gas pathway and reference means for generating reference signals, with the detection channel assembly including an energy source for emitting energy capable of being absorbed at least by a gas of interest in the sample gas stream, filter means for transmitting therethrough energy at wavelengths capable of being absorbed by the gas of interest, detector means capable of generating an output signal in proportion to an amount of energy issuing on the detector means form the filter means, and chopping means for during discrete periods causing energy to issue on the detector means for detecting the absorption the gas of interest in the sample gas stream,
  (3) timing means for generating cycle timing signals for use in timing detection events and processing of signals generated by the detector means,
  (4) temperature sensing means for measuring the temperature within the optical bench,
  (5) pressure measuring means for measuring the pressure within the gas pathway,
  (6) storage means for storing information for characterizing components of the optical bench, and
  (7) circuitry for processing the signals generated by the detector means relative to signals generated by the reference means, the timing means, the temperature sensing means, and the pressure sensing means, and for processing signals from the storage means that are representative of the information for characterizing the optical bench components;
(b) fluid flow control means including at least first pump means for drawing the sample gas stream through the gas pathway at a predetermined rate and flow sensing means for measuring flow rate of the sample gas stream through the gas pathway;
(c) analog signal processing circuitry further comprising,
  (1) analog input circuits for receiving signals output from the optical bench, processing these signals and converting them from analog to digital signals,
  (2) signal processing circuits for receiving the digital outputs from the analog input circuits and correcting the signals indicative of the partial pressure of the gas of interest in the gas pathway for temperature, collision broadening, cross-correction, pressure in the gas pathway, and characterization of the optical bench components, and
  (3) output circuit for providing at least the corrected signals for the partial pressure of the gas of interest in the gas pathway to display processing circuitry; and
(d) display processing circuitry for receiving the digital signals output from the analog signal processing circuitry, processing the signals, and generating signals for controlling the display of information or a display means, for output from the apparatus, and for activation of alarm means when appropriate.

37. The apparatus as recited in claim 36, wherein when the detector means is a lead selenide detector.

38. The apparatus as recited in claim 36, wherein the filter means passes energy having wavelengths in the absorption band of $CO_2$.

39. The apparatus as recited in clam 36, wherein the filter means passes energy having wavelengths in the absorption band of $N_2O$.

40. The apparatus as recited in claim 36, wherein the energy source is an infrared source.

41. The apparatus as recited in claim 36, wherein the pressure sensing means includes an absolute-type pressure sensor.

42. The apparatus as recited in claim 36, wherein the flow sensing means includes a differential-type pressure sensor.

43. The apparatus as recited in claim 36, wherein the flow rate of the sample gas stream through the gas pathway is preferably 50 cc/min.

44. The apparatus as recited in claim 36, wherein the system has a response time of not greater than 100 milliseconds.

45. The apparatus as recited in claim 36, wherein the microprocessor in the analog signal processing circuitry determines the partial pressure of the gas of interest for display according to the expression:

$$PPmmHg[X] = \frac{((PP[X])(\text{Barometric Prs}_N))}{\text{SampleCellPrs}}$$

where,

X = the gas of interest.

PP[=]the partial pressure of the gas of interest corrected for the pressure in the gas pathway, barometric pressure, cross-correction collision broadening, temperature, and characterization.

Barometric Prs$_N$ = the last measured barometric pressure stored in a memory.

SampleCellPrs = the pressure measured in the sample cell (optical bench) when the gas voltage are measured.

46. The apparatus as recited in claim 36, wherein the optical bench operates over a range of temperatures.

47. The apparatus as recited in claim 36, wherein the inlet means shapes the sample gas stream from a circular cross-section to a rectangular cross-section.

48. The apparatus as recited in claim 47, wherein the flow shaper further includes a filter disposed across the sample gas stream which assists in flow shaping.

49. The apparatus as recited in claim 36, wherein the apparatus further includes a shield means for shielding against background energy ingressing the optical path.

50. The apparatus as recited in claim 49, wherein the shield means further includes a first aperture means disposed adjacent the second window for shielding the optical path against ingress of background energy, a second aperture means spaced away from the first aperture means for shielding the optical path against ingress of background energy, and the chopping means disposed between the first and second aperture means.

51. The apparatus as recited in claim 36, wherein the reference means includes a reference cell containing a fixed amount of gas.

52. The apparatus as recited in claim 51, wherein the detector channel assembly further includes a first window mounted as a portion of a sidewall of each the gas pathway and the reference cell, the energy source mounted behind the first window to provide energy through the first window into the gas pathway and the reference cell and a second window mounted as a portion of the opposing sidewall of each the gas pathway and the reference cell from the first window for passing energy out of the gas pathway and the reference cell.

53. The apparatus as recited in claim 51, wherein the reference cell is disposed adjacent to the gas pathway in the optical path of the detection channel assembly.

54. The apparatus as recited in claim 36, wherein the fluid flow control means further includes a first valve means for controlling the choice of fluid flows through the gas pathway.

55. The apparatus as recited in claim 54, wherein the fluid flow control means further includes a second valve means for controlling the flow of a backflush fluid stream to a gas sampling means.

56. The apparatus as recited in claim 55, wherein the apparatus further includes third and fourth valve means capable of redirecting the fluid flow through an external device for measurement of predetermined constituents of a fluid flow, and a fifth valve means which in conjunction with the first valve means, the first pump means and the flow sensor means, is used for determining the fluid-tight integrity of the gas pathway.

* * * * *

UNITED STATES PATENT AND TRADEMARK OFFICE
CERTIFICATE OF CORRECTION

PATENT NO. : 4,907,166
DATED : September 25, 1987
INVENTOR(S) : James E. Corenman et al.

Page 1 of 2

It is certified that error appears in the above-identified patent and that said Letters Patent is hereby corrected as shown below:

Col. 5, ln. 24  After "the" delete "a"

Col. 5, ln. 25  After "into" insert -- a --

Col. 20, ln. 44  "flip flip" should be -- flip flop --

Col. 22, ln. 42  "0" should be -- $\emptyset$ --

Col. 22, ln. 44  "0" should be -- $\emptyset$ --.

Col. 26, ln. 42  Before "from" insert -- 922 --

Col. 28, ln. 18  Delete "the" (first occurence)

Col. 36, ln. 15  "$Prs_n 30$" should be -- $PrS_N^+$ --

Col. 36, ln. 30  "SamplCCellPrs" should be -- SampleCellPrs --

Col. 36, ln. 66  "$N_{20}$" should be -- $N_2O$ --

Col. 40, ln. 19  "busses" should be -- buses --

Col. 40, ln. 21  "busses" should be -- buses --

Col. 42, ln. 45  "flip flip" should be -- flip flop --

Col. 43, ln. 52  "(" should be -- ) --

Col. 52, ln. 26  "D8-5" should be --D8-15 --.

Col. 53, ln. 63  "ar" should be -- are --

UNITED STATES PATENT AND TRADEMARK OFFICE
CERTIFICATE OF CORRECTION

PATENT NO. : 4,907,166

DATED : September 25, 1987

INVENTOR(S) : James E. Corenman et al.

It is certified that error appears in the above-identified patent and that said Letters Patent is hereby corrected as shown below:

Col. 57, ln. 27  Delete "the" (second occurence)

Col. 61, ln. 50  "gas one" should be -- one gas --

Col. 63, ln. 15  "voltage" should be -- voltages --

Signed and Sealed this

Twenty-second Day of June, 1993

Attest:

MICHAEL K. KIRK

*Attesting Officer*   Acting Commissioner of Patents and Trademarks